(12) United States Patent
Liang et al.

(10) Patent No.: US 12,209,080 B2
(45) Date of Patent: *Jan. 28, 2025

(54) POLYMORPHIC FORMS OF KINASE INHIBITOR COMPOUND, PHARMACEUTICAL COMPOSITION CONTAINING SAME, PREPARATION METHOD THEREFOR AND USE THEREOF

(71) Applicant: EQUINOX SCIENCES, LLC, Wilmington, DE (US)

(72) Inventors: Congxin Liang, Palm Beach Gardens, FL (US); Lihua Xie, Shanghai (CN)

(73) Assignee: EQUINOX SCIENCES, LLC, Wilmington, DE (US)

( * ) Notice: Subject to any disclaimer, the term of this patent is extended or adjusted under 35 U.S.C. 154(b) by 256 days.

This patent is subject to a terminal disclaimer.

(21) Appl. No.: 17/348,482

(22) Filed: Jun. 15, 2021

(65) Prior Publication Data

US 2022/0356173 A1 Nov. 10, 2022

Related U.S. Application Data

(63) Continuation of application No. 16/338,357, filed as application No. PCT/CN2017/104506 on Sep. 29, 2017, now Pat. No. 11,053,224.

(30) Foreign Application Priority Data

Sep. 29, 2016 (CN) .......................... 201610866253.6

(51) Int. Cl.
| | |
|---|---|
| *A61K 31/404* | (2006.01) |
| *A61K 9/20* | (2006.01) |
| *A61K 9/48* | (2006.01) |
| *A61P 35/00* | (2006.01) |
| *C07D 403/14* | (2006.01) |

(52) U.S. Cl.
CPC .......... *C07D 403/14* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/485* (2013.01); *A61K 9/4858* (2013.01); *A61K 9/4866* (2013.01); *A61K 31/404* (2013.01); *A61P 35/00* (2018.01); *C07B 2200/13* (2013.01)

(58) Field of Classification Search
CPC ............. C07D 403/14; C07B 2200/13; A61K 9/2009; A61K 9/2013; A61K 9/2018; A61K 9/2027; A61K 9/2054; A61K 9/485; A61K 9/4858; A61K 9/4866; A61K 31/404; A61P 35/00
See application file for complete search history.

(56) References Cited

U.S. PATENT DOCUMENTS

| 8,524,709 B2 * | 9/2013 | Liang ...................... A61P 35/00 |
| | | 514/318 |
| 11,053,224 B2 * | 7/2021 | Liang ................... A61K 9/2009 |
| 2010/0256392 A1 | 10/2010 | Gavenda et al. |
| 2011/0026367 A1 | 2/2011 | Selic |
| 2011/0105580 A1 | 5/2011 | Krishna et al. |

(Continued)

FOREIGN PATENT DOCUMENTS

| CN | 101553482 A | 10/2009 |
| CN | 102272124 A | 12/2011 |

(Continued)

OTHER PUBLICATIONS

World Health Organization, "Cancer in Children," (Sep. 28, 2018); archived at Wayback Machine. Retrieved on Oct. 1, 2023 from https://web.archive.org/web/20181008184522/https://www.who.int/news-room/fact-sheets/detail/cancer-in-children (Year: 2018).*

(Continued)

*Primary Examiner* — Amanda L. Aguirre
(74) *Attorney, Agent, or Firm* — NKL Law; Allen Xue

(57) ABSTRACT

The invention discloses polymorphic forms of a compound of formula I, pharmaceutical compositions containing same, preparation method therefor and use thereof. The compound of formula I of the present invention is as shown in formula I, of which the crystalline form can be crystalline form 1, crystalline form 2, crystalline form 3, crystalline form 5, crystalline form 6 or crystalline form 7. All the crystalline forms of the compound of formula I in the present invention have good crystalline stability and chemical stability and a decrease in purity of their main ingredient less than 2%. The preparation method of the present invention may be used to produce the various crystalline forms of the compound of formula I with high purity, and suitable for large scale production.

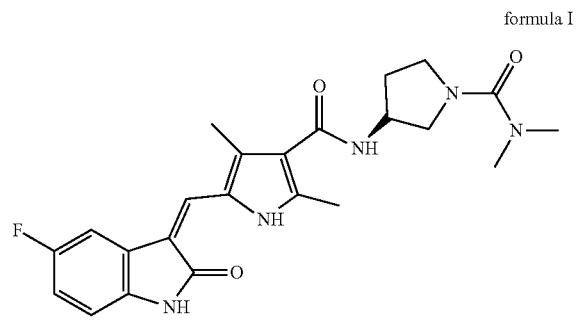

formula I

45 Claims, 31 Drawing Sheets

(56) References Cited

U.S. PATENT DOCUMENTS

2011/0275690 A1　11/2011　Selic
2012/0115866 A1　　5/2012　Li et al.

FOREIGN PATENT DOCUMENTS

WO　　03031438 A1　4/2003
WO　2008033562 A2　3/2008
WO　2010136458 A1　12/2010

OTHER PUBLICATIONS

Mossé, Y. P. "AnaplasticLymphomaKinase as a Cancer Target in Pediatric Malignancies" Clin. Cancer Res. 2016, 22, 546-552 (Year: 2016).*
EPO communication re EP Appl. No. 17855006.7, issued Apr. 7, 2020; pp. 1-10.
Applicant response to EPO communication re EP Appl. No. 17855006.7, filed on Oct. 6, 2020; pp. 1-8.

* cited by examiner

POLYMORPHIC FORMS OF KINASE INHIBITOR COMPOUND, PHARMACEUTICAL COMPOSITION CONTAINING SAME, PREPARATION METHOD THEREFOR AND USE THEREOF

RELATED APPLICATIONS

This application is a continuation of U.S. patent application Ser. No. 16/338,357, filed Mar. 29, 2019, which is a U.S. national stage entry of international application no. PCT/CN2017/104506, filed Sep. 29, 2017, which claims the benefit of priority from Chinese patent application no. 201610866253.6, filed Sep. 29, 2016, disclosures therein are incorporated herewith.

FIELD OF THE INVENTION

The invention belongs to the field of pharmaceutical crystalline form, in particular to polymorphic forms of a kinase inhibitor compound, pharmaceutical compositions containing same, preparation method therefor and use thereof.

BACKGROUND OF THE INVENTION

Sunitinib is a potent multi-target kinase inhibitor that has significant therapeutic effects on cancer, particularly on renal cell carcinoma (RCC) and gastrointestinal stromal tumors (GIST). Nevertheless, the application of sunitinib is limited due to its side effects. Among them, the most common and serious side effects in clinical practice include neutropenia and fatigue toxicity, which greatly limit the use of sunitinib as a single agent or in combination with other therapies. For example, the result of Phase I clinical trial of the composition of sunitinib and everolimus for the treatment of patients with metastatic renal cell carcinoma indicated that, due to the poor tolerance for daily administration, everolimus was necessary to be administered weekly (2011 Genitourinary Cancer Symposium, abst #311). Furthermore, when the treatment of an administration of sunitinib for 4 weeks on 2 weeks off, followed by an administration of everolimus for 5 weeks on 1 week off was adopted, although its tolerance was improved, the curative effect could not meet the desired goal (2014 Genitourinary Cancer Symposium, abst #438).

WO2008033562A2 and CN101553482A disclose a class of sunitinib derivatives obtained by replacing the diethylaminoethyl side chain of sunitinib with a cyclic side chain, such as 5-[5-fluoro-2-oxo-1,2-dihydro-indole-(3Z)-ylidenemethyl]-2,4-dimethyl-1H-pyrrole-3-carboxylic acid ((S)-1-dimethylcarbamoyl-pyrrolidin-3-yl)-amide as shown in formula I (molecular weight is 439.48, molecular formula is $C_{23}H_{26}FN_5O_3$), which could reduce the inhibitory activity of AMPK, thus relieving the side effects of sunitinib, such as fatigue toxicity.

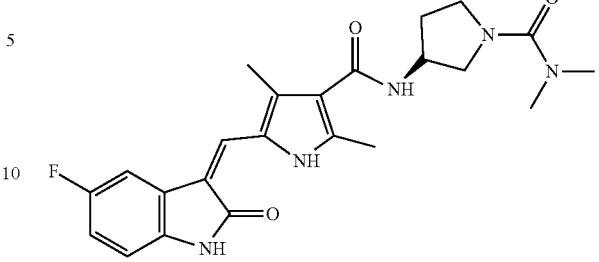

In the above compound, the basic diethyl amino ethyl side chain in the sunitinib structure was replaced by a neutral group of dimethylcarbamoyl-pyrrolidine-3-yl. The basic side chain was advantageous for the solubility of sunitinib, but it also leads to extensive accumulation of the drug in human tissues, thus increasing its toxicity. Although the replacement of the basic side chain with the neutral group could reduce the accumulation of the drug in the tissues to reduce its toxicity, but it would significantly reduce water solubility of the drug, which has become a challenge that must be faced in the drug development. Moreover, the existing preparation methods are still unable to meet the needs of large-scale production. Therefore, there is an urgent need to develop compound forms and preparations thereof with good solubility, stability, bioavailability or drug metabolism, and preparation methods suitable for large-scale production, to obtain good pharmaceutical efficacy.

SUMMARY OF THE INVENTION

To improve the above-mentioned problems in the prior art, the present invention provides a crystalline form of the compound of formula I:

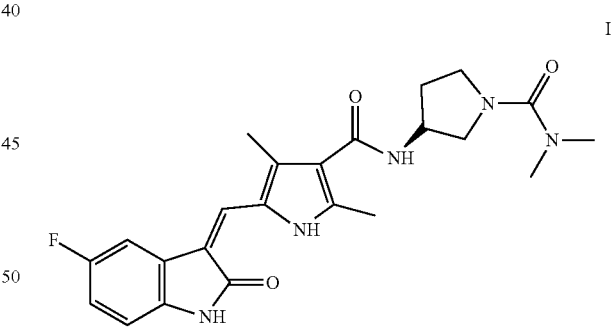

wherein, the crystalline form is selected from the group consisting of the following crystalline form 1, crystalline form 2, crystalline form 3, crystalline form 5, crystalline form 6, crystalline form 7 or a mixture of any two or more thereof;

the X-ray powder diffraction pattern of the crystalline form 1 has characteristic peaks at the diffraction angle 2θ of 4.3±0.2°, 8.6±0.2° and 12.9±0.2°;

the X-ray powder diffraction pattern of the crystalline form 2 has characteristic peaks at the diffraction angle 2θ of 8.8±0.2°, 10.1±0.2°, 23.8±0.2° and 26.7±0.2°;

the X-ray powder diffraction pattern of the crystalline form 3 has characteristic peaks at the diffraction angle 2θ of 7.8±0.2°;

the X-ray powder diffraction pattern of the crystalline form 5 has characteristic peaks at the diffraction angle 2θ of 8.7±0.2°, 17.0±0.2° and 17.4±0.2°;

the X-ray powder diffraction pattern of the crystalline form 6 has characteristic peaks at the diffraction angle 2θ of 7.9±0.2°, 9.0±0.2° and 17.7±0.2°;

the X-ray powder diffraction pattern of the crystalline form 7 has characteristic peaks at the diffraction angle 2θ of 9.5±0.2°, 10.6±0.2° and 16.0±0.2°;

wherein the X-ray powder diffraction patterns were all measured using Kα spectrum of the Cu target.

Preferably, the X-ray powder diffraction pattern of the crystalline form 1 has characteristic peaks at the diffraction angle 2θ of 4.3±0.2°, 8.6±0.2°, 12.9±0.2° and 18.3±0.2°.

Preferably, the X-ray powder diffraction pattern of the crystalline form 1 has characteristic peaks at the diffraction angle 2θ of 4.3±0.2°, 7.6±0.2°, 8.6±0.2°, 12.9±0.2° and 18.3±0.2°.

Preferably, the X-ray powder diffraction pattern of the crystalline form 1 has characteristic peaks at the diffraction angle 2θ of 4.3±0.2°, 7.6±0.2°, 8.6±0.2°, 12.9±0.2°, 17.2±0.2° and 18.3±0.2°.

More preferably, the X-ray powder diffraction pattern of the crystalline form 1 has characteristic peaks at the diffraction angle 2θ of 4.3±0.2°, 7.6±0.2°, 8.6±0.2°, 9.0±0.2°, 12.4±0.2°, 12.9±0.2°, 17.2±0.2° and 18.3±0.2°.

As an example, the X-ray powder diffraction pattern of the crystalline form 1 has characteristic peaks at the diffraction angle 2θ selected from the following angles: 4.3±0.2°, 6.7±0.2°, 7.6±0.2°, 8.6±0.2°, 9.0±0.2°, 12.4±0.2°, 12.9±0.2°, 14.3±0.2°, 15.5±0.2°, 16.7±0.2°, 17.2±0.2°, 18.3±0.2°, 19.6±0.2°, 20.3±0.2°, 21.2±0.2°, 21.5±0.2°, 22.4±0.2°, 23.1±0.2°, 24.2±0.2°, 25.1±0.2°, 25.9±0.2°, 27.0±0.2°, 27.4±0.2°, 28.8±0.2°, 30.8±0.2°, 33.4±0.2°, 39.2±0.2°.

As an example, the X-ray powder diffraction pattern of the crystalline form 1 has characteristic peaks at the diffraction angle 2θ selected from the following angles: 4.3±0.2°, 6.7±0.2°, 7.6±0.2°, 8.6±0.2°, 9.0±0.2°, 10.1±0.2°, 12.4±0.2°, 12.9±0.2°, 14.3±0.2°, 15.5±0.2°, 16.7±0.2°, 17.2±0.2°, 18.3±0.2°, 19.6±0.2°, 20.3±0.2°, 21.2±0.2°, 21.5±0.2°, 22.4±0.2°, 23.1±0.2°, 24.2±0.2°, 25.1±0.2°, 25.9±0.2°, 27.0±0.2°, 27.4±0.2°, 28.8±0.2°, 30.8±0.2°, 32.9±0.2°, 33.4±0.2°, 35.0±0.2°, 37.5±0.2°, 39.2±0.2°.

Most preferably, the data of the X-ray powder diffraction pattern of the crystalline form 1 is as shown in Table 1 below:

TABLE 1

| No. | 2θ (°) | Interplanar spacing (Å) | Relative intensity (%) |
| --- | --- | --- | --- |
| 1 | 4.3 | 20.4593 | 100 |
| 2 | 6.7 | 13.2673 | 5.9 |
| 3 | 7.6 | 11.5948 | 22.9 |
| 4 | 8.6 | 10.2964 | 91.2 |
| 5 | 9.0 | 9.8192 | 12.6 |
| 6 | 10.1 | 8.7556 | 0.8 |
| 7 | 12.4 | 7.1183 | 20.9 |
| 8 | 12.9 | 6.8769 | 81.7 |
| 9 | 14.3 | 6.179 | 6 |
| 10 | 15.5 | 5.7282 | 1.1 |
| 11 | 16.7 | 5.3001 | 1.7 |
| 12 | 17.2 | 5.162 | 25 |
| 13 | 18.3 | 4.8441 | 36.6 |
| 14 | 19.6 | 4.5211 | 7.7 |
| 15 | 20.3 | 4.362 | 6.7 |
| 16 | 21.2 | 4.1794 | 4.3 |
| 17 | 21.5 | 4.1296 | 9 |
| 18 | 22.4 | 3.9651 | 2.9 |

TABLE 1-continued

| No. | 2θ (°) | Interplanar spacing (Å) | Relative intensity (%) |
| --- | --- | --- | --- |
| 19 | 23.1 | 3.8462 | 4.6 |
| 20 | 24.2 | 3.6749 | 3.4 |
| 21 | 25.1 | 3.5448 | 3.7 |
| 22 | 25.9 | 3.4398 | 4.7 |
| 23 | 27.0 | 3.2994 | 2.3 |
| 24 | 27.4 | 3.2523 | 1.2 |
| 25 | 28.8 | 3.0992 | 6.4 |
| 26 | 30.8 | 2.8983 | 5.6 |
| 27 | 32.9 | 2.7229 | 0.6 |
| 28 | 33.4 | 2.6818 | 1.2 |
| 29 | 35.0 | 2.5643 | 0.6 |
| 30 | 37.5 | 2.3947 | 0.8 |
| 31 | 39.2 | 2.2949 | 2.6 |

Non-limitingly, a typical example of the crystalline form 1 has an X-ray powder diffraction pattern substantially as shown in FIG. 1.

Further, the polarized light micrograph (PLM) pattern of the crystalline form 1 is shown in FIG. 2. Wherein crystalline form 1 is a slender rod-like crystal.

The solubility of the crystalline form 1 in a conventional solvent at 25° C. is as follows: the solubility in methanol is 5-12.5 mg/mL; the solubility in ethanol is 1-2.5 mg/mL; the solubility in water is less than 1 mg/mL; the solubility in acetone is 1-2.5 mg/mL; the solubility in ethyl acetate is less than 1 mg/mL; the solubility in methyl tert-butyl ether is less than 1 mg/mL; the solubility in tetrahydrofuran is 1-2.5 mg/mL; the solubility in acetonitrile is less than 1 mg/mL; the solubility in toluene is less than 1 mg/mL; the solubility in n-Heptane is less than 1 mg/mL.

Further, the crystalline form 1 has a thermogravimetric analysis (TGA) pattern substantially as shown in FIG. 3. Wherein, the crystalline form 1 has a weight loss of about 2.6% before 170° C., which is an anhydrous substance with a decomposition temperature of about 320° C.

Further, the crystalline form 1 has a differential scanning calorimetry (DSC) pattern substantially as shown in FIG. 4. Wherein, the crystalline form 1 has an exothermic peak at 150-170° C., confirmed as an exothermic peak of crystal transformation. The crystalline form 1 was transformed to crystalline form 3, and the melting point of the crystalline form 1 is about 260° C.

Further, the crystalline form 1 has a dynamic vapor sorption (DVS) pattern substantially as shown in FIG. 5. Wherein, the weight change of the crystalline form 1 within the range of 0% RH to 80% RH is about 2.8%.

Preferably, the X-ray powder diffraction pattern of the crystalline form 2 has characteristic peaks at the diffraction angle 2θ of 8.8±0.2°, 10.1±0.2°, 17.7±0.2°, 19.9±0.2°, 20.5±0.2°, 23.8±0.2° and 26.7±0.2°.

More preferably, the X-ray powder diffraction pattern of the crystalline form 2 has characteristic peaks at the diffraction angle 2θ of 5.1±0.2°, 8.8±0.2°, 10.1±0.2°, 11.6±0.2°, 14.6±0.2°, 15.2±0.2°, 16.5±0.2°, 17.3±0.2°, 17.7±0.2°, 18.8±0.2°, 19.9±0.2°, 20.5±0.2°, 21.7±0.2°, 23.2±0.2°, 23.8±0.2° and 26.7±0.2°.

As an example, the X-ray powder diffraction pattern of the crystalline form 2 has characteristic peaks at the diffraction angle 2θ selected from the following angles: 5.1±0.2°, 7.8±0.2°, 8.4±0.2°, 8.8±0.2°, 10.1±0.2°, 11.6±0.2°, 14.6±0.2°, 15.2±0.2°, 15.5±0.2°, 16.1±0.2°, 16.5±0.2°, 17.3±0.2°, 17.7±0.2°, 18.8±0.2°, 19.0±0.2°, 19.4±0.2°, 19.9±0.2°, 20.5±0.2°, 21.7±0.2°, 22.1±0.2°, 23.2±0.2°, 23.8±0.2°, 24.7±0.2°, 25.9±0.2°, 26.7±0.2°, 27.5±0.2°, 28.7±0.2°, 29.7±0.2°, 30.3±0.2°, 31.6±0.2°, 32.5±0.2°, 33.1±0.2°, 36.8±0.2° and 38.9±0.2°.

Most preferably, the data of the X-ray powder diffraction pattern of the crystalline form 2 is shown in Table 2 below:

TABLE 2

| No. | 2θ (°) | Interplanar spacing (Å) | Relative intensity (%) |
|---|---|---|---|
| 1 | 5.1 | 17.4405 | 17.6 |
| 2 | 7.8 | 11.2919 | 4.3 |
| 3 | 8.4 | 10.4787 | 7.7 |
| 4 | 8.8 | 10.0847 | 100 |
| 5 | 10.1 | 8.7346 | 67 |
| 6 | 11.6 | 7.6512 | 18.2 |
| 7 | 14.6 | 6.0471 | 12.1 |
| 8 | 15.2 | 5.8318 | 16.3 |
| 9 | 15.5 | 5.6971 | 8.5 |
| 10 | 16.1 | 5.5136 | 6.1 |
| 11 | 16.5 | 5.381 | 51.5 |
| 12 | 17.3 | 5.1331 | 11.9 |
| 13 | 17.7 | 5.017 | 59.6 |
| 14 | 18.8 | 4.7262 | 28.6 |
| 15 | 19.0 | 4.6559 | 7.2 |
| 16 | 19.4 | 4.561 | 2.9 |
| 17 | 19.9 | 4.4572 | 67.7 |
| 18 | 20.5 | 4.3371 | 34.3 |
| 19 | 21.7 | 4.0921 | 19.1 |
| 20 | 22.1 | 4.0156 | 4.4 |
| 21 | 23.2 | 3.8338 | 11.4 |
| 22 | 23.8 | 3.7355 | 90 |
| 23 | 24.7 | 3.602 | 4.8 |
| 24 | 25.9 | 3.4316 | 3.5 |
| 25 | 26.7 | 3.3329 | 71.2 |
| 26 | 27.5 | 3.2427 | 3 |
| 27 | 28.7 | 3.1113 | 6.4 |
| 28 | 29.7 | 3.003 | 2.6 |
| 29 | 30.3 | 2.9506 | 4.3 |
| 30 | 31.6 | 2.832 | 2.5 |
| 31 | 32.5 | 2.7538 | 3.8 |
| 32 | 33.1 | 2.7054 | 3.3 |
| 33 | 36.8 | 2.4426 | 2.9 |
| 34 | 38.9 | 2.3154 | 2.1 |

Non-limitingly, a typical example of the crystalline form 2 has an X-ray powder diffraction pattern substantially as shown in FIG. 7.

Further, the polarized light micrograph (PLM) pattern of the crystalline form 2 is shown in FIG. 8. Wherein the crystalline form 2 is a fine needle crystal.

Further, the crystalline form 2 has a thermogravimetric analysis (TGA) pattern substantially as shown in FIG. 9. Wherein the crystalline form 2 has a weight loss of about 0.3% before 200° C., which is an anhydrous substance with a decomposition temperature of about 320° C.

Further, the crystalline form 2 has a differential scanning calorimetry (DSC) pattern substantially as shown in FIG. 10. Wherein the melting point of the crystalline form 2 is about 258° C.

Further, the crystalline form 2 has a dynamic vapor sorption (DVS) pattern substantially as shown in FIG. 11. Wherein, the weight change of the crystalline form 2 in the range of 0% RH to 80% RH is about 0.05%.

Preferably, the crystalline form 3 has characteristic peaks at diffraction angles 2θ of 7.8±0.2°, 9.3±0.2°, 13.7±0.2°, and 16.0±0.2° in the X-ray powder diffraction pattern.

More preferably, the crystalline form 3 has characteristic peaks at diffraction angles 2θ of 3.9±0.2°, 7.8±0.2°, 9.3±0.2°, 13.7±0.2°, 16.0±0.2°, 18.2±0.2°, and 27.2±0.2° in the X-ray powder diffraction pattern.

As an example, the diffraction angle 2θ of the crystalline form 3 in an X-ray powder diffraction pattern is shown in Table 3.

Most preferably, the data of the X-ray powder diffraction pattern of the crystalline form 3 is shown in Table 3 below:

TABLE 3

| No. | 2θ (°) | Interplanar spacing (Å) | Relative intensity (%) |
|---|---|---|---|
| 1 | 3.9 | 22.4054 | 14.8 |
| 2 | 7.8 | 11.2691 | 100 |
| 3 | 9.3 | 9.4587 | 8.5 |
| 4 | 10.5 | 8.4343 | 4.9 |
| 5 | 11.0 | 8.0222 | 0.5 |
| 6 | 11.7 | 7.5525 | 1 |
| 7 | 12.9 | 6.848 | 1.2 |
| 8 | 13.7 | 6.4673 | 5.2 |
| 9 | 16.0 | 5.5486 | 6.2 |
| 10 | 16.8 | 5.2658 | 1.6 |
| 11 | 17.7 | 5.0055 | 1.1 |
| 12 | 18.2 | 4.8634 | 6 |
| 13 | 19.3 | 4.5898 | 4.4 |
| 14 | 20.2 | 4.3831 | 2.8 |
| 15 | 20.8 | 4.2668 | 2.5 |
| 16 | 22.1 | 4.0183 | 1.4 |
| 17 | 22.9 | 3.8801 | 1.4 |
| 18 | 23.2 | 3.8238 | 1.5 |
| 19 | 23.9 | 3.7229 | 1.2 |
| 20 | 24.7 | 3.6034 | 0.6 |
| 21 | 25.3 | 3.517 | 0.6 |
| 22 | 26.3 | 3.3857 | 1.6 |
| 23 | 27.2 | 3.275 | 5.6 |
| 24 | 27.5 | 3.2382 | 3.7 |
| 25 | 28.7 | 3.1112 | 1.4 |
| 26 | 30.1 | 2.9664 | 0.6 |
| 27 | 31.3 | 2.8511 | 0.4 |
| 28 | 32.2 | 2.7745 | 0.4 |
| 29 | 32.6 | 2.7477 | 0.3 |
| 30 | 33.4 | 2.6816 | 0.4 |
| 31 | 33.9 | 2.6411 | 0.4 |
| 32 | 35.3 | 2.5402 | 1.9 |
| 33 | 38.6 | 2.3315 | 0.3 |
| 34 | 39.2 | 2.2959 | 0.3 |

Non-limitingly, a typical example of the crystalline form 3 has an X-ray powder diffraction pattern substantially as shown in FIG. 12.

Further, the polarized light micrograph (PLM) pattern of the crystalline form 3 is shown in FIG. 13. Wherein the crystalline form 3 is fine particles with partial agglomeration.

Further, crystalline form 3 has a thermogravimetric analysis (TGA) pattern substantially as shown in FIG. 14. Wherein the crystalline form 3 has a weight loss of about 0.2% before 200° C., which is an anhydrous substance with a decomposition temperature of about 320° C.

Further, the crystalline form 3 has a differential scanning calorimetry (DSC) pattern substantially as shown in FIG. 15. Wherein the melting point of the crystalline form 3 is about 261° C.

Further, the crystalline form 3 has a dynamic vapor sorption (DVS) pattern substantially as shown in FIG. 16. Wherein, the weight change of the crystalline form 3 in the range of 0% RH to 80% RH is about 0.08%.

Preferably, the crystalline form 5 has characteristic peaks at diffraction angles 2θ of 8.3±0.2°, 8.7±0.2°, 9.4±0.2°, 17.0±0.2°, 17.4±0.2° and 18.1±0.2° in the X-ray powder diffraction pattern.

More preferably, the crystalline form 5 has characteristic peaks at diffraction angles 2θ of 4.1±0.2°, 8.3±0.2°, 8.7±0.2°, 9.4±0.2°, 10.5±0.2°, 13.4±0.2°, 17.0±0.2°, 17.4±0.2° and 18.1±0.2° in the X-ray powder diffraction pattern.

As an example, the diffraction angle 2θ of the crystalline form 5 in an X-ray powder diffraction pattern is shown in Table 4.

Most preferably, the data of the X-ray powder diffraction pattern of the crystalline form 5 is shown in Table 4 below:

TABLE 4

| No. | 2θ (°) | Interplanar spacing (Å) | Relative intensity (%) |
|---|---|---|---|
| 1 | 3.3 | 26.5323 | 7 |
| 2 | 4.1 | 21.3225 | 12.9 |
| 3 | 8.3 | 10.6951 | 43.5 |
| 4 | 8.7 | 10.1334 | 100 |
| 5 | 9.4 | 9.4158 | 37.5 |
| 6 | 10.5 | 8.4483 | 10.6 |
| 7 | 13.4 | 6.6111 | 11.9 |
| 8 | 15.0 | 5.891 | 8 |
| 9 | 17.0 | 5.2106 | 69.9 |
| 10 | 17.4 | 5.0803 | 59.7 |
| 11 | 18.1 | 4.9074 | 46.9 |
| 12 | 19.9 | 4.4581 | 6.1 |
| 13 | 20.5 | 4.3203 | 8.1 |
| 14 | 21.0 | 4.2203 | 4.8 |
| 15 | 22.4 | 3.9719 | 9.4 |
| 16 | 23.8 | 3.7382 | 6.8 |
| 17 | 26.8 | 3.328 | 6.3 |
| 18 | 27.2 | 3.2755 | 4.4 |
| 19 | 33.0 | 2.7099 | 2.8 |

Non-limitingly, a typical example of the crystalline form 5 has an X-ray powder diffraction pattern substantially as shown in FIG. 17.

Further, the polarized light micrograph (PLM) of the crystalline form 5 is shown in FIG. 18. Wherein crystalline form 5 is fine particles with partial agglomeration.

Further, the crystalline form 5 has a thermogravimetric analysis (TGA) pattern substantially as shown in FIG. 19. Wherein the crystalline form 5 has a weight loss of about 1.2% before 200° C., which is an anhydrous substance with a decomposition temperature of about 319° C.

Further, the crystalline form 5 has a differential scanning calorimetry (DSC) pattern substantially as shown in FIG. 20. Wherein the melting point of the crystalline form 5 is about 258° C. The broad absorption peak before 100° C. is caused by the removal of the surface solvent.

Further, the crystalline form 5 has a dynamic vapor sorption (DVS) pattern substantially as shown in FIG. 21. Wherein, the weight change of the crystalline form 5 in the range of 0% RH to 80% RH is about 2.5%.

Preferably, the crystalline form 6 has characteristic peaks at diffraction angles 2θ of 7.9±0.2°, 9.1±0.2°, 9.6±0.2°, 16.4±0.2°, 17.7±0.2° and 18.0±0.2° in the X-ray powder diffraction pattern.

More preferably, the crystalline form 6 has characteristic peaks at diffraction angles 2θ of 3.9±0.2°, 7.9±0.2°, 9.1±0.2°, 9.6±0.2°, 13.2±0.2°, 16.4±0.2°, 17.7±0.2° and 18.0±0.2° in the X-ray powder diffraction pattern.

As an example, the diffraction angle 2θ of the crystalline form 6 in an X-ray powder diffraction pattern is shown in Table 5 below.

Most preferably, data of the X-ray powder diffraction pattern of the crystalline form 6 is shown in Table 5 below:

TABLE 5

| No. | 2θ (°) | Interplanar spacing (Å) | Relative intensity (%) |
|---|---|---|---|
| 1 | 3.9 | 22.3988 | 22.1 |
| 2 | 7.9 | 11.2115 | 100 |
| 3 | 9.1 | 9.7966 | 29.5 |
| 4 | 9.6 | 9.1847 | 14.4 |
| 5 | 10.6 | 8.3524 | 9.9 |
| 6 | 11.8 | 7.4696 | 1.2 |
| 7 | 13.2 | 6.7002 | 10.5 |

TABLE 5-continued

| No. | 2θ (°) | Interplanar spacing (Å) | Relative intensity (%) |
|---|---|---|---|
| 8 | 14.8 | 5.996 | 3.4 |
| 9 | 16.4 | 5.4065 | 11 |
| 10 | 17.7 | 5.0118 | 24.5 |
| 11 | 18.0 | 4.9178 | 13.6 |
| 12 | 19.8 | 4.471 | 7.3 |
| 13 | 20.2 | 4.3924 | 2.1 |
| 14 | 21.6 | 4.1064 | 1.4 |
| 15 | 22.4 | 3.9617 | 3.6 |
| 16 | 23.8 | 3.7413 | 2.8 |
| 17 | 26.2 | 3.4036 | 1.7 |
| 18 | 26.8 | 3.3234 | 3.1 |
| 19 | 27.7 | 3.2135 | 2 |
| 20 | 30.8 | 2.8968 | 0.9 |
| 21 | 35.0 | 2.5611 | 1.3 |
| 22 | 35.9 | 2.499 | 1.2 |

Non-limitingly, a typical example of the crystalline form 6 has an X-ray powder diffraction pattern substantially as shown in FIG. 22.

Further, the polarized light micrograph (PLM) of the crystalline form 6 is shown in FIG. 23. Wherein crystalline form 6 is fine particles with partial agglomeration.

Further, the crystalline form 6 has a thermogravimetric analysis (TGA) pattern substantially as shown in FIG. 24. Wherein the crystalline form 6 has a weight loss of about 0.7% before 200° C., which is an anhydrous substance with a decomposition temperature of about 320° C.

Further, the crystalline form 6 has a differential scanning calorimetry (DSC) pattern substantially as shown in FIG. 25. Wherein the melting point of the crystalline form 6 is about 259° C.

Further, the crystalline form 6 has a dynamic vapor sorption (DVS) pattern substantially as shown in FIG. 26. Wherein, the weight change of the crystalline form 6 in the range of 0% RH to 80% RH is about 0.26%.

Preferably, the crystalline form 7 has characteristic peaks at diffraction angles 2θ of 9.5±0.2°, 10.6±0.2°, 13.8±0.2°, 14.3±0.2°, 16.0±0.2°, 18.2±0.2° and 25.1±0.2° in the X-ray powder diffraction pattern.

More preferably, the crystalline form 7 has characteristic peaks at diffraction angles 2θ of 4.8±0.2°, 9.5±0.2°, 10.6±0.2°, 13.8±0.2°, 14.3±0.2°, 16.0±0.2°, 18.2±0.2°, 25.1±0.2°, 27.8±0.2° and 28.9±0.2° in the X-ray powder diffraction pattern.

As an example, the diffraction angle 2θ of the crystalline form 7 in an X-ray powder diffraction pattern is shown in Table 6 below.

Most preferably, the data of the X-ray powder diffraction pattern of the crystalline form 7 is shown in Table 6 below:

TABLE 6

| No. | 2θ (°) | Interplanar spacing (Å) | Relative intensity (%) |
|---|---|---|---|
| 1 | 4.8 | 18.4678 | 14.8 |
| 2 | 7.8 | 11.2961 | 3.3 |
| 3 | 8.8 | 10.0852 | 1.1 |
| 4 | 9.5 | 9.2814 | 100 |
| 5 | 10.1 | 8.7146 | 3.4 |
| 6 | 10.6 | 8.3398 | 27.6 |
| 7 | 13.8 | 6.4097 | 20.1 |
| 8 | 14.3 | 6.1966 | 20.2 |
| 9 | 16.0 | 5.5346 | 41.5 |
| 10 | 17.5 | 5.0675 | 1.8 |
| 11 | 18.2 | 4.8803 | 19.4 |
| 12 | 18.6 | 4.7664 | 3.9 |
| 13 | 19.1 | 4.6483 | 1.5 |
| 14 | 19.9 | 4.4538 | 0.8 |

TABLE 6-continued

| No. | 2θ (°) | Interplanar spacing (Å) | Relative intensity (%) |
|---|---|---|---|
| 15 | 21.5 | 4.1297 | 3.2 |
| 16 | 21.8 | 4.0699 | 1.3 |
| 17 | 22.5 | 3.9449 | 0.6 |
| 18 | 23.0 | 3.857 | 1.6 |
| 19 | 23.9 | 3.72 | 1.8 |
| 20 | 24.5 | 3.635 | 2 |
| 21 | 25.1 | 3.5498 | 15.5 |
| 22 | 26.8 | 3.3233 | 1.1 |
| 23 | 27.1 | 3.2922 | 1.8 |
| 24 | 27.8 | 3.2017 | 7.3 |
| 25 | 28.9 | 3.0888 | 5.3 |
| 26 | 30.5 | 2.9293 | 1.1 |
| 27 | 31.2 | 2.8647 | 1.1 |
| 28 | 32.1 | 2.7893 | 1.2 |
| 29 | 32.4 | 2.7588 | 3.2 |
| 30 | 33.1 | 2.7007 | 1.5 |
| 31 | 33.6 | 2.6618 | 1.6 |
| 32 | 38.2 | 2.354 | 0.5 |
| 33 | 38.8 | 2.3164 | 0.7 |

Non-limitingly, a typical example of the crystalline form 7 has an X-ray powder diffraction pattern substantially as shown in FIG. 27.

Further, the polarized light micrograph (PLM) of the crystalline form 7 is shown in FIG. 28. Wherein the crystalline form 7 is fine particles with partial agglomeration.

Further, the crystalline form 7 has a thermogravimetric analysis (TGA) pattern substantially as shown in FIG. 29. Wherein the crystalline form 7 has a weight loss of about 0.5% before 200° C., which is an anhydrous substance with a decomposition temperature of about 320° C.

Further, the crystalline form 7 has a differential scanning calorimetry (DSC) pattern substantially as shown in FIG. 30. Wherein the melting point of the crystalline form 7 is about 259° C.

Further, the crystalline form 7 has a dynamic vapor sorption (DVS) pattern substantially as shown in FIG. 31. Wherein, the weight change of the crystalline form 7 in the range of 0% RH to 80% RH is about 0.27%.

According to the present invention, the crystalline form 1, crystalline form 2, crystalline form 3, crystalline form 5, crystalline form 6 or crystalline form 7 preferably has a purity of more than 50%, for example, 80% or more, 85% or more, 90% or more, 95% or more, such as 99% or more, 99.5% or more, or 99.9% or more.

The present invention also provides a method for preparing said crystalline forms, comprising one or more of the following methods:

(1) preparation method 1 of the crystalline form 1, comprising the following steps: the compound of formula I is mixed with a solvent to obtain a clear solution, and then the solvent is volatilized to obtain the crystalline form 1; the solvent is selected from the group consisting of methanol, a mixture of methanol and acetone or aqueous methanol solution;

preparation method 2 of the crystalline form 1, comprising the following steps: the compound of formula I is mixed with methanol to obtain a clear solution, and a solvent is added to the clear solution under stirring to precipitate a solid to obtain the crystalline form 1; the solvent is selected from the group consisting of acetone, ethyl acetate, methyl tert-butyl ether or acetonitrile;

preparation method 3 of the crystalline form 1, comprising the following steps: the compound of formula I is mixed with methanol to obtain a clear solution, and the clear solution is added to a solvent under stirring to precipitate a solid to obtain the crystalline form 1; the solvent is selected from the group consisting of water or methyl tert-butyl ether;

preparation method 4 of the crystalline form 1, comprising the following steps: the compound of formula I is mixed with a solvent to obtain a clear solution, cooled, and precipitated a crystal by stirring; the solvent is selected from the group consisting of methanol, aqueous methanol solution, a mixture of methanol and ethyl acetate, a mixture of methanol and methyl tert-butyl ether, or a mixture of methanol and acetonitrile.

In the preparation method 1 of the crystalline form 1, the temperature for volatilizing the solvent is preferably 10-40° C. The mass to volume ratio of the compound of formula I to the solvent is preferably 10 mg/(0.5 to 2.2 mL), such as 10 mg/(0.5 to 2 mL), for example, 5 mg/1.0 mL, 10 mg/0.6 mL, or 10 mg/1.2 mL. When the solvent is a mixture of methanol and acetone, the volume ratio of methanol to acetone is preferably 1:(1.5-2.5), for example, 1:2; when the solvent is an aqueous methanol solution, the volume ratio of methanol to water is preferably 6:(0.5-1.5), for example, 6:1.

In the preparation method 2 of the crystalline form 1, the mixing may be performed under a heating condition to facilitate the dissolution of the compound of formula I. The temperature for mixing is preferably 45-55° C., such as 50° C. According to the common knowledge in the art, in order to ensure the obtaining of the clear solution, hot filtration may be carried out after the compound of formula I is sufficiently dissolved. The mass to volume ratio of the compound of formula I to methanol is preferably 20 mg/(1.2 to 1.6 mL), such as 20 mg/1.4 mL. The mass to volume ratio of the compound of formula I to the solvent is preferably 20 mg/(2 to 4 mL), such as 20 mg/3 mL.

In the preparation method 3 of the crystalline form 1, the mixing may be performed under a heating condition to facilitate the dissolution of the compound of the formula I. The temperature for mixing is preferably 45-55° C., such as 50° C. According to the common knowledge in the art, in order to ensure the obtaining of the clear solution, hot filtration may be carried out after the compound of formula I is sufficiently dissolved. The mass to volume ratio of the compound of formula I to methanol is preferably 20 mg/1.2 mL to 20 mg/1.6 mL, such as 20 mg/1.4 mL. The mass to volume ratio of the compound of formula I to the solvent is preferably 20 mg/(2.0 to 15 mL), such as 20 mg/(2.5 to 12.0 mL), such as 20 mg/3.0 mL, 20 mg/5.2 mL and 20 mg/11.2 mL.

In the preparation method 4 of the crystalline form 1, the mixing may be performed under a heating condition to facilitate the dissolution of the compound of the formula I, usually by the means of water bath heating; the temperature for mixing is preferably 45-70° C., such as 50° C. or reflux temperature. According to the common knowledge in the art, in order to ensure the obtaining of the clear solution, hot filtration may be carried out after the compound of formula I is sufficiently dissolved. Preferably, the compound of formula I is mixed with the solvent and heated to reflux to obtain a clear solution.

Preferably, the preparation method 4 comprises the following steps: the compound of formula I is mixed with methanol, heated to reflux to obtain a clear solution, cooled, crystallized under stirring, filtered, washed and dried;

Optionally, the preparation method 4 further comprises a concentration step. For example, part of the solvent can be removed by concentration after the clear solution is obtained;

Preferably, the concentration is carried out under reduced pressure, and the vacuum degree of the reduced pressure condition may be, for example, 200 to 1500 Pa, such as 500 to 1000 Pa;

The concentration temperature may be 20-35° C.;

Preferably, the time for refluxing is less than 4 hours, such as not more than 2 hours;

Preferably, the water content of methanol is not more than 10%, such as not more than 6%, such as not more than 5%, preferably not more than 1%, such as anhydrous methanol.

The target temperature for the cooling may be 1 to 50° C., such as 4 to 50° C., such as 5 to 35° C. or 10 to 20° C.

The temperature of stirring for crystallization may be 1 to 50° C., for example, 4 to 50° C., such as 5 to 35° C. or 10 to 20° C.

The solvent used for washing may be selected from the group consisting of methanol, aqueous methanol solution, a mixture of methanol and ethyl acetate, a mixture of methanol and methyl tert-butyl ether or a mixture of methanol and acetonitrile, preferably methanol, which may be used for preparing the above-mentioned clear solution.

The mass to volume ratio of the compound of formula I to the solvent is preferably 20 mg/(0.5 to 2.2 mL), for example, 20 mg/0.8 mL, 20 mg/1.0 mL, 20 mg/1.2 mL, 20 mg/1.4 mL, 20 mg/1.8 mL, 20 mg/2.2 mL. When the solvent is methanol, its moisture content is preferably ≤10%; when the solvent is an aqueous methanol solution, the volume ratio of methanol to water is preferably 7:(1.5 to 2.5), such as 7:2; When the solvent is a mixture of methanol and ethyl acetate, the volume ratio of methanol to ethyl acetate is preferably 1:(1.5 to 2.5), such as 1:2; when the solvent is a mixture of methanol and methyl tert-butyl ether, the volume ratio of methanol to methyl tert-butyl ether is preferably 4:(6 to 8), such as 4:7; when the solvent is a mixture of methanol and acetonitrile, the volume ratio of methanol to acetonitrile is preferably 1:(0.5 to 1.5), such as 1:1.

(2) Preparation method of the crystalline form 2, comprising the following steps: the compound of formula I is mixed with a solvent and stirred for 2 to 6 days, and the crystal slurry is separated by solid-liquid separation followed by drying to obtain the crystal; the solvent is selected from the group consisting of water, ethyl acetate, toluene, aqueous acetone solution, aqueous acetonitrile solution, a mixture of ethanol and toluene or aqueous methanol solution.

In the preparation method of the crystalline form 2, the compound of formula I may be the crystalline form 1 and/or the crystalline form 6. The temperature for stirring is preferably 4 to 50° C. According to common knowledge in the art, during the stirring, the temperature of the mixture can be adjusted. For example, the mixture can be stirred at 50° C. for 2 hours and then at room temperature for 2 days. The mass to volume ratio of the compound of the formula I to the solvent is preferably (12.5 to 40.0 mg)/mL, for example 10 mg/0.5 mL, 10 mg/0.6 mL, 10 mg/0.8 mL, or 199 mg/5 mL. When the solvent is an aqueous acetone solution, the volume ratio of acetone to water is preferably 2:1; when the solvent is aqueous acetonitrile solution, the volume ratio of acetonitrile to water is preferably 2:1 to 5:1; when the solvent is a mixture of ethanol and toluene, the volume ratio of ethanol to toluene is preferably 1:1; when the solvent is aqueous methanol solution, the volume ratio of methanol to water is preferably 1:1. Conventional methods and conditions in the art may be employed in the solid-liquid separation. For example, filtration or filtration after centrifugation may be generally employed. When only filtration is used for the solid-liquid separation, the filtration usually is suction filtration. Conventional methods and conditions in the art may be employed in drying process. Said drying is preferably vacuum drying, and more preferably vacuum drying at room temperature for 10 to 16 hours.

(3) Preparation method 1 of the crystalline form 3, comprising the following steps: the compound of formula I is mixed with tetrahydrofuran to obtain a clear solution, and the solvent is volatilized to obtain crystalline form 3;

preparation method 2 of the crystalline form 3, comprising the following steps: the compound of formula I is mixed with ethanol to obtain a clear solution, and the solvent is volatilized to obtain crystalline form 3;

preparation method 3 of the crystalline form 3, comprising the following steps: the compound of the formula I is mixed with an aqueous ethanol solution to obtain a clear solution, and the solvent is volatilized at 60° C. to obtain the crystalline form 3;

preparation method 4 of the crystalline form 3, comprising the following steps: the compound of formula I is mixed with a solvent and stirred, and then the crystal slurry is separated by solid-liquid separation followed by drying to obtain the crystalline form 3; the solvent is selected from the group consisting of an ethanol, acetone or aqueous tetrahydrofuran solution;

preparation method 5 of the crystalline form 3, comprising the following steps: The compound of formula I is mixed with a solvent to obtain a clear solution, cooled, crystalized by stirring to obtain the crystalline form 3; the solvent is selected from the group consisting of tetrahydrofuran or a mixture of methanol and tetrahydrofuran;

preparation method 6 of the crystalline form 3, comprising the following steps: the crystalline form 1 is heated to 180-190° C., cooled to room temperature to obtain the crystalline form 3; or, the crystalline form 7 is heated to 258° C. and cooled to room temperature to obtain the crystalline form 3.

In the preparation method 1 of the crystalline form 3, the temperature for volatilizing the solvent is preferably 10-40° C. The mass to volume ratio of the compound of formula I to tetrahydrofuran is preferably 1 mg/(0.5-1.5 mL), such as 1:1 mL.

In the preparation method 2 of the crystalline form 3, the mass to volume ratio of the compound of formula I to tetrahydrofuran is preferably 5 mg/(2-4 mL), such as 5 mg/3 mL.

In the preparation method 3 of the crystalline form 3, the mass to volume ratio of the compound of formula I to tetrahydrofuran is preferably 10 mg/(1.0-1.4 mL), such as 10 mg/1.2 mL. In the aqueous ethanol solution, the volume ratio of ethanol to water is preferably 5:(0.5-1.5), such as 5:1.

In the preparation method 4 of the crystalline form 3, the crystalline form of the compound of formula I is preferably crystalline form 1. The temperature for stirring is preferably 4 to 30° C., and the time of stirring is preferably 20 hours to 6 days. The mass to volume ratio of the compound of formula I to the solvent is preferably 10 mg/(0.4-0.8 mL), for example, 10 mg/0.5 mL, 10 mg/0.8 mL, 200 mg/8 mL, 200 mg/10 mL, or 201 mg/15 mL. When the solvent is an aqueous solution of tetrahydrofuran, the volume ratio of tetrahydrofuran to water is preferably 1:0.5-1.5, such as 1:1. Conventional methods and conditions in the art may be employed in the solid-liquid separation. For example, filtration or filtration after centrifugation may be generally employed. When only filtration is used for the solid-liquid separation, the filtration usually is suction filtration. Conventional methods and conditions in the art may be employed in drying process. Said drying is preferably vacuum drying, and more preferably vacuum drying at room temperature for 10 to 16 hours.

In a specific embodiment of the preparation method 4 of crystalline form 3, 201.0 mg of the compound of formula I is mixed with 15 mL ethanol to form a suspension, and the mixture is stirred at 800 rpm for 20 hours at room temperature followed by suction filtration of the crystal slurry to separate the solid, which is then dried at 60° C. for 1 hour to obtain the crystalline form 3.

In the preparation method 5 of crystalline form 3, the mixing may be performed under a heating condition to facilitate the dissolution of the compound of formula I, usually by the means of water bath heating. The temperature for mixing is preferably 45-55° C., such as 50° C. According to the common knowledge in the art, in order to ensure the obtaining of the clear solution, hot filtration may be carried out after the compound of formula I is sufficiently dissolved. The target temperature for the cooling is preferably 4 to 20° C. The mass to volume ratio of the compound of formula I to acetone is preferably 20 mg/(0.4 to 5 mL). When the solvent is a mixture of methanol and tetrahydrofuran, the volume ratio of methanol to tetrahydrofuran is preferably 1:(0.8-1.2), such as 1:1.

(4) Preparation method 1 of the crystalline form 5, comprising the following steps: the compound of formula I is mixed with acetone to obtain a clear solution, cooled, stirred and crystallized to obtain crystalline form 5;

preparation method 2 of the crystalline form 5, comprising the following steps: the compound of formula I is mixed with a solvent and stirred, and the crystal slurry is separated by solid-liquid separation followed by drying to obtain the crystalline form 5; or, the compound of formula I is mixed with a solvent, added with the crystal seed of crystalline form 5 and stirred, and the crystal slurry is separated by solid-liquid separation followed by drying to obtain the crystalline form 5; the solvent is methyl tert-butyl ether or acetone.

In the preparation method 1 of the crystalline form 5, the mixing may be performed under a heating condition to facilitate the dissolution of the compound of the formula I. Usually, a method of water bath heating may be adopted. The temperature for mixing is preferably 45-55° C., such as 50° C. According to the common knowledge in the art, in order to ensure the obtaining of the clear solution, hot filtration may be carried out after the compound of formula I is sufficiently dissolved. The target temperature for the cooling is preferably 4 to 20° C. The mass to volume ratio of the compound of formula I to acetone is preferably 20 mg/4 to 6 mL, such as 20 mg/5 mL.

In the preparation method 2 of the crystalline form 5, the crystalline form of the compound of formula I is preferably the crystalline form 1. The seed of the crystalline form 5 can be added optionally and can be obtained by any one of the preparation methods of crystalline form 5. The seed crystal of the crystalline form 5 is preferably added in an amount of not more than 2% of the total mass of the crystal slurry. The temperature for stirring is preferably room temperature, and the time for stirring is preferably 1 to 6 days. The mass to volume ratio of the compound of formula I to the solvent is preferably (18-22 mg)/mL, such as (19.9-20 mg)/mL. Conventional methods and conditions in the art may be employed in the solid-liquid separation, and generally filtration or filtration after centrifugation may be employed. When only filtration is used for solid-liquid separation, the filtration usually is suction filtration. Conventional methods and conditions in the art may be employed in the drying process. Said drying is preferably vacuum drying, and more preferably vacuum drying at room temperature for 10 to 16 hours.

(5) Preparation method 1 of the crystalline form 6, comprising the following steps: the compound of formula I is mixed with a mixture of toluene and methanol to obtain a clear solution, and the solvent is volatilized at room temperature to obtain the crystalline form 6;

preparation method 2 of crystalline form 6, comprising the following steps: the compound of the formula I is mixed with methanol to obtain a clear solution, and the clear solution and toluene are mixed under stirring to precipitate a solid to obtain the crystalline form 6;

preparation method 3 of the crystalline form 6, comprising the following steps: the compound of formula I is mixed with toluene and stirred for 16 or more hours, and the crystal slurry is dried to obtain the crystalline form 6; or, after the compound of formula I is mixed with toluene, the seed of the crystalline form 6 was added and stirred, and then the crystal slurry is dried to obtain the crystalline form 6.

In the preparation method 1 of the crystalline form 6, the mass to volume ratio of the compound of formula I to the mixture of toluene and methanol is preferably 10 mg/(0.3 to 0.5 mL), such as 10 mg/0.4 mL. In the mixture of toluene and methanol, the volume ratio of toluene to methanol is preferably 1:(0.7-1.3), such as 1:1. According to the common knowledge in the art, the mixing process can be supplemented with an ultrasonic dispersing operation to obtain a clear solution. Moreover, after the ultrasonic dispersion, filtration may be further performed to ensure that a clear solution is obtained.

In the preparation method 2 of the crystalline form 6, the mixing may be performed under a heating condition to facilitate the dissolution of the compound of formula I, preferably at a temperature of 45-55° C. According to the common knowledge in the art, in order to ensure the obtaining of the clear solution, hot filtration may be carried out after the compound of formula I is sufficiently dissolved. The mass to volume ratio of the compound of formula I to methanol is preferably 20 mg/(1.2 to 1.6 mL), such as 20 mg/1.4 mL. The mass to volume ratio of the compound of formula I to toluene is preferably 20 mg/(2.5 to 12.0 mL), such as 20 mg/(3.0 to 11.2 mL).

In the preparation method 3 of the crystalline form 6, the crystalline form of the compound of formula I is preferably the crystalline form 1. The seed of crystalline form 6 can be added optionally, and can be obtained by any one of the preparation methods of crystalline form 6. The seed crystal of crystalline form 6 is preferably added in an amount of not more than 2% of the total mass of the crystal slurry. The temperature for stirring is preferably room temperature, and the time for stirring is preferably 16 to 24 hours. The mass to volume ratio of the compound of formula I to the solvent is preferably 5-15 mg/mL, such as 10 mg/mL. Conventional methods and conditions in the art may be employed in the drying process Said drying is preferably vacuum drying, and more preferably vacuum drying at 50 to 60° C. for about 1 hour.

(6) Preparation method 1 of the crystalline form 7, comprising the following steps: the compound of formula I is mixed with ethyl acetate, stirred for about 30 minutes at 45-55° C., for example 50° C.; the crystal slurry is dried after solid-liquid separation to obtain the crystalline form 7;

preparation method 2 of the crystalline form 7, comprising the following steps: the compound of the formula I is mixed with a mixture of N, N-dimethylacetamide and toluene, and is dried after solid-liquid separation to obtain the crystalline form 7;

preparation method 3 of the crystalline form 7, comprising the following steps: the crystalline form 1 and/or the crystalline form 5 is mixed with water and stirred, and the crystal slurry is separated by solid-liquid separation followed by drying to obtain the crystalline form 7.

In the preparation method 1 of crystalline form 7, the crystalline form of the compound of formula I is preferably the crystalline form 1. The mass to volume ratio of the compound of formula I to the solvent is preferably (18 to 22 mg)/mL, such as (19.9 to 20 mg)/mL. Conventional methods and conditions in the art may be employed in the solid-liquid separation, and generally filtration or filtration after centrifugation may be employed. When only filtration is used for solid-liquid separation, the filtration usually is suction filtration. Conventional methods and conditions in the art may be employed in the drying process. Said drying is preferably vacuum drying, and more preferably vacuum drying at 60° C. for about 1 hour.

In the preparation method 2 of crystalline form 7, the time for stirring is preferably about 1 hour. In the mixture of N,N-dimethylacetamide and toluene, the volume ratio of N,N-dimethylacetamide to toluene is preferably 1:(8 to 10), such as 1:9. Conventional methods and conditions in the art may be employed in the solid-liquid separation, and generally filtration or filtration after centrifugation may be employed. When only filtration is used for solid-liquid separation, the filtration usually is suction filtration. Conventional methods and conditions in the art may be employed in the drying process.

In the preparation method 3 of crystalline form 7, the temperature for stirring is preferably room temperature, and the time for stirring is preferably about 24 hours.

In the present invention, the volatilization of the solvent can be carried out by conventional methods and conditions in the art, generally by natural volatilization to dryness, usually in an open vessel.

Unless otherwise specified, the preparation method of each of the crystalline forms may also optionally comprise the step of drying the resulting crystalline form. The drying comprises atmospheric drying or vacuum drying. The temperature of vacuum drying may be about 35° C. or more, such as about 40° C. or more, about 45° C. or more, or about 50° C. or more, for example about 40 to 60° C. Vacuum degree of the vacuum drying may be, for example, 200 to 1500 Pa, such as 500 to 1000 Pa.

According to the preparation method of each crystalline form according to the present invention, the compound of formula I as a raw material may be either a pure product or a crude product prepared by a known method or the method of the present invention. When the crude product is selected as the raw material, an appropriate amount of activated carbon may be added when the raw material is mixed with a solvent to improve the purity of the product.

The present invention also provides a pharmaceutical composition, which comprises a therapeutically and/or prophylactically effective amount of the crystalline form of the present invention or a crystalline form prepared by the preparation of the present invention, and at least one pharmaceutically acceptable adjuvant.

Wherein, the crystalline form may be selected from one or more of the group consisting of the crystalline form 1, crystalline form 2, crystalline form 3, crystalline form 5, crystalline form 6, and crystalline form 7.

Pharmaceutically acceptable adjuvants (such as carriers, excipients, etc.) that may be used in the pharmaceutical composition of the present invention include, but are not limited to, ion exchangers, aluminum, aluminium stearate, lecithin, self-emulsifying drug delivery system (SEDDS) such as D-α-tocopheryl polyethylene glycol 1000 succinate, surfactant can be used in a pharmaceutical dosage form such as Tween or other similar polymeric delivery matrices, serum protein such as human serum albumin, buffer substance such as phosphate, glycine, sorbic acid, potassium sorbate, mixture of partial glycerides of saturated fatty acids, water, salts or electrolytes such as protamine sulfate, disodium hydrogen phosphate, potassium hydrogen phosphate, sodium chloride, zinc salt, colloidal silicon, magnesium trisilicate, polyvinylpyrrolidone, cellulose-based substance, polyethylene glycol, sodium carboxymethyl cellulose, polyacrylate, wax, polyethylene-polyoxypropylene block polymer, polyethylene diols and lanolin. Cyclodextrins, such as α-cyclodextrin, β-cyclodextrin, γ-cyclodextrin, or chemically modified derivatives thereof such as hydroxyalkyl cyclodextrin such as 2-hydroxypropyl-β-cyclodextrin, 3-hydroxypropyl-β-cyclodextrin, or other soluble derivatives of cyclodextrin, which may also be advantageously used to enhance the delivery of compounds of the formula described in the present invention.

Moreover, the pharmaceutical composition may further comprise or substantially not comprise other forms of the compound of formula I, such as other crystalline and/or amorphous forms.

According to a preferably embodiment of the pharmaceutical composition of the present invention, the ratio of the total molar amount of the crystalline form 1, crystalline form 2, crystalline form 3, crystalline form 5, crystalline form 6 and crystalline form 7 to the total molar amount of other forms of the compound of formula I may be greater than 50:50, for example, 60:40 or more, 70:30 or more, 80:20 or more, 90:10 or more, 95:5 or more, 99:1 or more, or 100:0. As an exemplary embodiment, in the pharmaceutical composition of the present invention, the ratio of the molar amount of the crystalline form 1 to the total molar of the crystalline form 2, crystalline form 3, crystalline form 5, crystalline form 6, crystalline form 7 and other forms of the compound of formula I may be greater than 50:50, for example, 60:40 or more, 70:30 or more, 80:20 or more, 90:10 or more, 95:5 or more, 99:1 or more, or 100:0. Alternatively, the ratio of the molar amount of the crystalline form 2 to the total molar amount of the crystalline form 1, crystalline form 3, crystalline form 5, crystalline form 6, crystalline form 7, and other forms of the compound of formula I may be greater than 50:50, for example, 80:20 or more, 90:10 or more, 95:5 or more, 99:1 or more, or 100:0.

In the present invention, the pharmaceutical composition may be in solid or liquid state, such as solid oral dosage forms, including tablet, granule, powder, pill, and capsule; liquid oral dosage forms, including liquor, syrup, suspension, dispersion and emulsion; injectable formulations comprising liquor, dispersion, and lyophilized formulation. The formulations can be suitable for rapid release, delayed release or modified release of the active ingredient. It may be a conventional, dispersible, chewable, orally dissolving or rapidly melting formulation. The route for administration comprises oral administration, intravenous subcutaneous injection, injection into tissue, transdermal administration, rectal administration, intranasal administration, and the like.

For example, the pharmaceutical composition is a capsule comprising a therapeutically and/or prophylactically effective amount of the crystalline form according to the present invention, Pearlitol 200 SD, sodium bicarbonate, sodium lauryl sulfate, and croscarmellose sodium.

For example, the pharmaceutical composition is a tablet, and its core comprises a therapeutically and/or prophylactically effective amount of the crystalline form of the present invention, mannitol, microcrystalline cellulose, sodium bicarbonate powder, anhydrous citric acid, croscarmellose sodium, sodium lauryl sulfate, crospovidone, fumed silica, sodium stearyl fumarate, and water which can be optionally present or absent;

Preferably, one or more of the ingredients in the pharmaceutical composition are ground and/or sieved.

According to the present invention, the pharmaceutical composition may further comprise one or more therapeutically or prophylactically active ingredients in addition to the various forms described above for the compound of formula I. When the composition of the present invention comprises such an active ingredient, the above various forms of the compounds of formula I and the additional active ingredients may be provided with a dosage level of about 1% to 100%, more preferably about 5% to 95%, usually administered in a single treatment regimen. The additional active ingredient can be administered as a part of a multi-dose administration regimen separately from the various forms of the compounds of formula I of the present invention. Optionally, the additional active ingredient may be a part of a single dosage form which is mixed with the various forms described above for the compound of formula I of the invention in a single composition The pharmaceutical compositions may be prepared by conventional methods known to those skilled in the art. For example, one or more of the crystalline forms of the present invention may be mixed with one or more pharmaceutically acceptable adjuvants and another component which is optionally present. As an example, a solid formulation may be prepared by process such as direct mixing, granulation, and the like.

The invention also provides a method for treating or preventing a disease or condition, comprising administering an effective amount of the crystalline form or pharmaceutical composition of the invention to a subject.

The invention also provides a method for modulating (e.g., inhibiting, antagonizing, agonizing) kinase activity, comprising contacting the kinase with the crystalline form or pharmaceutical composition described herein.

The present invention also provides the use of the crystalline form or pharmaceutical composition in the preparation of a drug. The drug may be used to modulate the kinase activity of a subject in need thereof. Alternatively, the drug may be used to treat or prevent a disease or condition.

Preferably, the disease or condition may be any one of diseases or conditions mediated by a kinase (such as one or more selected from VEGFR, PDGFR, Flt-3, KIT, RET or CSF1R). The disease or condition may be cancer, which comprises, for example, renal cell carcinoma, gastrointestinal stromal tumor, tumor or proliferative disorder.

The present invention also provides a method for improving the efficacy of sunitinib or a derivative thereof or reducing side effects thereof (such as neutropenia and/or fatigue toxicity), comprising administering an effective amount of the crystalline form or pharmaceutical composition of the invention to the subject in place of sunitinib or a derivative thereof.

The present invention also provides a process for preparing the compound of formula I, comprising the following reaction:

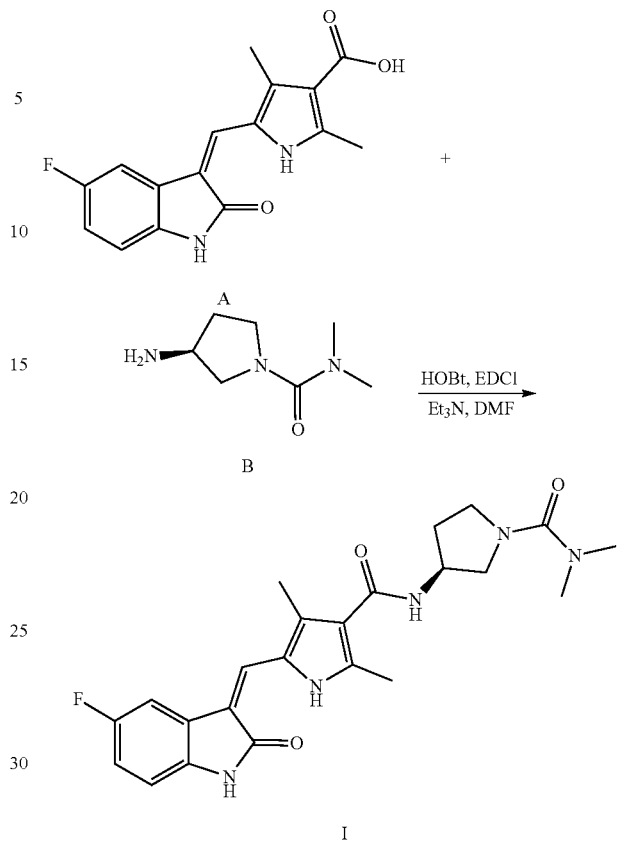

wherein, HOBt represents hydroxybenzotriazole, EDCI represents 1-ethyl-3-(3-dimethylaminopropyl) carbodiimide, $Et_3N$ represents triethylamine, and DMF represents N,N-dimethyl formamide.

The molar ratio of compound A to B may be 1:1-1:3, for example, 1:1-1:1.5, such as 1:1.2;

The molar ratio of compound A to triethylamine may be 1:1-1:10, for example, 1:5;

The molar ratio of compound A and EDCI may be 1:1-1:3, for example, 1:1.2-1:1.8, such as 1:1.5;

Preferably, the reaction is performed in an inert atmosphere (such as nitrogen atmosphere);

Preferably, the reaction temperature may be 5-45° C., such as 20-30° C.;

Preferably, after the reaction is completed, an ether solvent, such as methyl tert-butyl ether, is added to the reaction mixture, stirred, filtered, and the filter cake is washed with methyl tert-butyl ether;

Preferably, the product washed with methyl tert-butyl ether is mixed with methanol or an aqueous solution thereof, such as anhydrous methanol, and heated to reflux;

The time for refluxing is preferably not more than 2 hours, for example 0.5 to 1 hour;

Preferably, after refluxing, the reaction mixture is cooled to 10-20° C., stirred for 1-3 hours and filtered;

Preferably, the filter cake is washed with methanol, such as cold methanol, and dried to give an initial product of the compound of formula I. The drying comprises atmospheric drying or vacuum drying. The temperature for vacuum drying may be about 35° C. or more, such as about 40° C. or more, about 45° C. or more, or about 50° C. or more, for example about 40 to 60° C. The vacuum degree of the vacuum drying may be, for example, 200 to 1500 Pa, such as 500 to 1000 Pa.

Interpretation and Definition of the Terms

The term "subject" refers to animal, such as mammal, including but not limited to primates such as human, cow, sheep, goat, horse, dog, cat, rabbit, rat, mouse, and the like. In an embodiment of the invention, the "subject" refer to human.

The term "about" means that, according to the present invention, the described numerical value may include the range of ±20%, such as ±10%, such as ±5%, ±1%, ±0.5%, or ±0.1% of the specific numerical value, to implement the technical solution of the present invention.

In the present invention, the term "crystalline form" is not only understood as "crystal type" or "crystal structure"; in the technical solution, "crystalline form" can be further understood as "substance having a specific crystal structure" or "crystal having a specific crystal type".

In the present invention, the "crystalline form" is confirmed by the X-ray diffraction pattern characterization as shown herein. Those skilled in the art can understand that the experimental error therein depends on the conditions of the instrument, the preparation process of the sample, and the purity of the sample. In particularly, it is well known to those skilled in the art that X-ray diffraction patterns would generally vary with the different conditions of the instrument. In addition, the experimental error of the peak angle usually is 5% or less, accordingly the error of these angles should also be taken into account and usually an error of ±0.2° is allowed. In addition, due to experimental factors such as sample height, the overall offset of the peak angle can be caused, so that a certain offset usually can be allowed. Thus, it will be understood by those skilled in the art that any crystalline form having the same or similar features as the characteristic peaks in the pattern of the present invention is within the scope of the present invention.

The term "anhydrous" means that the product contains no more than 3.0%, such as no more than 1.5%, such as no more than 1% by weight of water by thermogravimetric analysis (TGA).

In the present invention, "room temperature" is a room temperature in the conventional sense of the art, and is generally 10 to 30° C.

In the present invention, "crystal slurry" means "a supersaturated solution containing the compound of formula I" (i.e., the solution containing an insoluble solid).

"Pharmaceutically acceptable" means that the drug is present in a form or an amount that does not adversely affect the subject to be administered.

In the present invention, unless otherwise specified, the parameters and detection method parameters of each detection instrument are as follows:

(1) X-ray powder diffractometer (XRD) & hot stage XRD, Bruker D8 Advance diffractometer; technical specifications: Kα irradiation (40 Kv, 40 mA) with a copper target wavelength of 1.54 Å, θ-2θ goniometer, Mo monochromator, Lynxeye detector; standard material: $Al_2O_3$; acquisition software: Diffrac Plus XRD Commander; analysis software: MDI Jade 6;

Method parameters: detection angle, 340° 2θ/3-30° 2θ (hot stage XRD); step length, 0.02° 2θ; velocity, 0.15 s·step$^{-1}$; weight of the sample to be detected >2 mg.

(2) Differential Thermal Scanner (DSC), TA Instruments Q200 DSC; controlling software: Thermal Advantage; analytical software: Universal Analysis; sample plate: aluminium crucible; amount of the sample to be detected: 0.5-5 mg; protective gas: nitrogen; gas flow rate: 40 mL/min; detection method: the temperature is raised at a rate of 10° C./min, and then raised to 300° C. after equilibration at 20° C.

(3) Thermogravimetric Analyzer (TGA), TA Instruments Q500 TGA; controlling software: Thermal Advantage; analysis software: Universal Analysis; sample plate: platinum crucible; amount of the sample to be detected: 1-10 mg; protective gas: nitrogen; gas flow fate: 40 mL/min; detection method: high resolution 3.0 (Hi-Res sensitivity 3.0), the temperature is raised at a rate of 10° C./min to 350° C.;

(4) Dynamic Water Adsorption (DVS), TA Instruments Q5000 TGA; controlling software: Thermal Advantage; analysis software: Universal Analysis; sample plate: platinum crucible; amount of the sample to be detected: 1-10 mg; protective gas: nitrogen; gas flow fate: 10 mL/min; detection method: equilibration at 25° C., humidity: 0%, isothermal treatment: 90 min, weight change to be detected: from 0% RH to 80% RH;

Criterion: non-hygroscopic: no more than 0.2%; slightly hygroscopic: more than 0.2%, but no more than 2.0%; easily hygroscopic: higher than 2%, but no higher than 15%; extremely easily hygroscopic: higher than 15%.

(5) Hot Stage Polarized Light Microscope (PLM), XP-500E; Shanghai Changfang Optical Instrument Co., Ltd.

(6) Determination of solubility: visual inspection method, comprising the following specific process: the known amount of sample is weighed at 25° C., added with a solvent gradually, stirred or supplemented with ultrasound until the sample is dissolved to clear visually; the amount of the consumed solvent is recorded. If the sample is still not dissolved at a specific concentration, its solubility is expressed as "<specific concentration";

Criterion: extremely easily soluble: greater than 1 g/mL; easily soluble: greater than 100 mg/mL but less than or equal to 1 g/mL; soluble: greater than 33.3 mg/mL but less than or equal to 100 mg/mL; more slightly soluble: greater than 10 mg/mL but less than or equal to 33.3 mg/mL; slightly soluble: greater than 1 mg/mL but less than or equal to 10 mg/mL; extremely slightly dissolved: greater than 0.1 mg/mL, but less than or equal to 1 mg/mL; practically insoluble or insoluble: less than 0.1 mg/mL.

On the basis of the common knowledge in the art, the above preferred conditions may be optionally combined to obtain other preferred embodiments of the present invention.

All the reagents and raw materials used in the present invention are commercially available.

ADVANTAGEOUS EFFECTS

The crystalline forms according to the present invention have good stability and chemical stability. The reduction in the purity of the main ingredient under the stability experimental condition is less than 2%. In addition, the crystalline forms of the present invention have improved pharmaceutical properties, pharmacokinetic properties, tissue accumulation and stability (such as milling stability), thereby possessing good prospect of pharmaceutical applications. Surprisingly, the inventors have also found that the crystalline form 2 has good stability and hygroscopicity. Furthermore, in addition to its excellent stability and improved hygroscopicity, the crystalline form 1 can further achieve good overall performance in other aspects, thus having excellent drug-forming properties. Also, the crystalline form 1 and form 2 have the highest solubility in methanol.

Additionally, the method for preparing the crystalline forms described in the present invention, such as the method for obtaining the crystalline form 1 from methanol, can produce the crystalline forms of the compound of formula I in good yield and high purity. Also, the preparation methods according to the invention are suitable for large-scale production.

EXAMPLES

Figure 1:
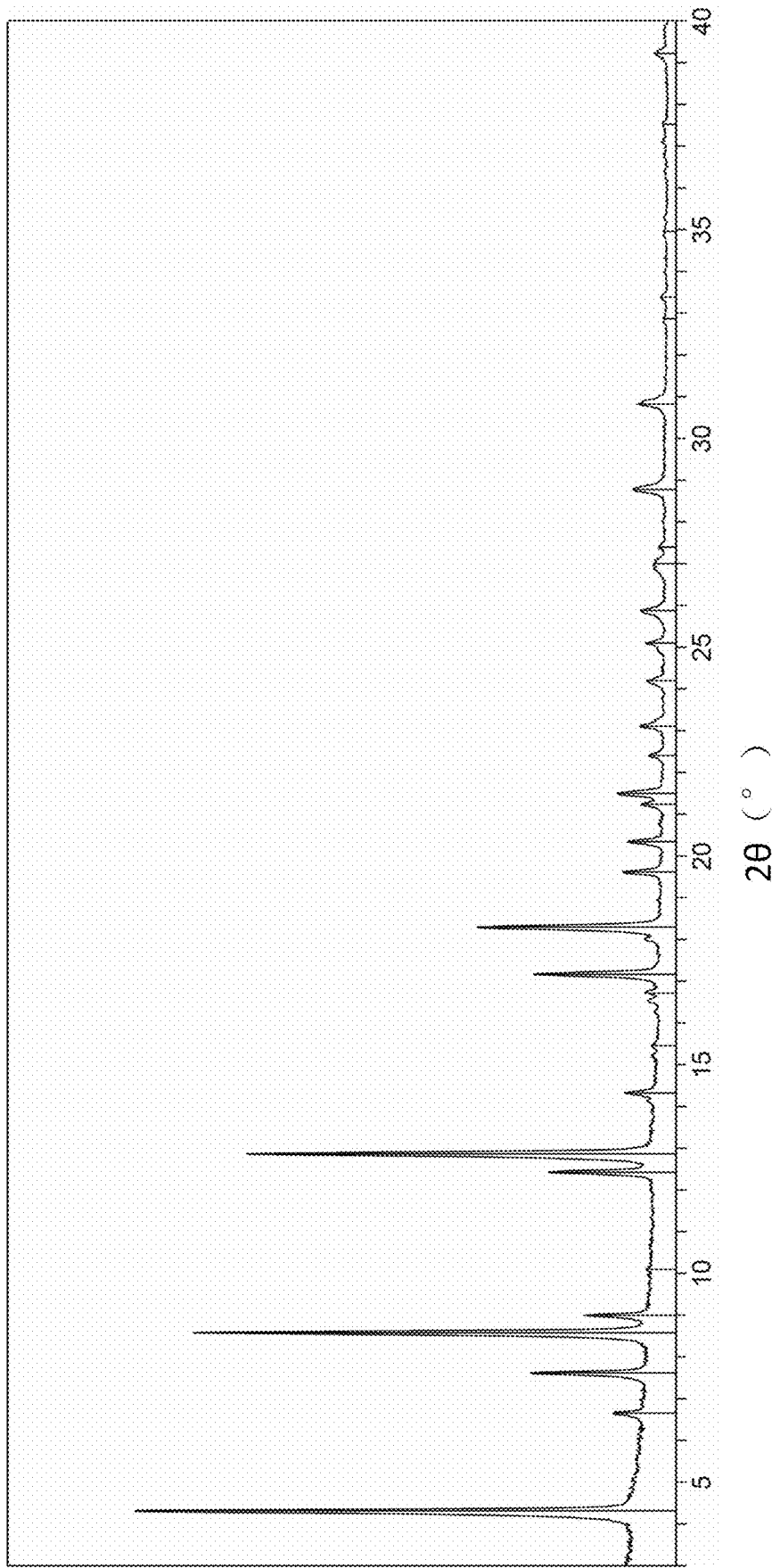
FIG. 1 shows the X-ray powder diffraction pattern of the crystalline form 1.

The present invention will be further illustrated by the following examples, but it should not be construed that the present invention is confined to the scope of the examples. In the experimental methods of the following examples, where the specific conditions were not specifically described, they could be selected from conventional methods and conditions, or those recited in commercially available instructions.

Unless otherwise specified, the information and parameters of the detection instruments and methods used in the following examples and effect examples are as follows:

(1) X-ray powder diffractometer (XRD) & hot stage XRD, Bruker D8 Advance diffractometer; technical specifications: Kα irradiation (40 Kv, 40 mA) with a copper target wavelength of 1.54 Å, θ-2θ goniometer, Mo monochromator, Lynxeye detector; standard material: $Al_2O_3$; acquisition software: Diffrac Plus XRD Commander; analysis software: MDI Jade 6;

Method parameters: detection angle, 3-40° 2θ/3-30° 2θ (hot stage XRD); step length, 0.02° 2θ; velocity, 0.15 s/step; weight of the sample to be detected >2 mg.

(2) Differential Thermal Scanner (DSC), TA Instruments Q200 DSC; controlling software: Thermal Advantage; analytical software: Universal Analysis; sample plate: aluminium crucible; amount of the sample to be detected: 0.5-5 mg; protective gas: nitrogen; gas flow rate: 40 mL/min; detection method: the temperature is raised at a rate of 10° C./min, and then raised to 300° C. after equilibration at 20° C.

(3) Thermogravimetric Analyzer (TGA), TA Instruments Q500 TGA; controlling software: Thermal Advantage; analysis software: Universal Analysis; sample plate: platinum crucible; amount of the sample to be detected: 1-10 mg; protective gas: nitrogen; gas flow fate: 40 mL/min; detection method: high resolution 3.0 (Hi-Res sensitivity 3.0), the temperature is raised at a rate of 10° C./min to 350° C.;

(4) Dynamic Water Adsorption (DVS), TA Instruments Q5000 TGA; controlling software: Thermal Advantage; analysis software: Universal Analysis; sample plate: platinum crucible; amount of the sample to be detected: 1-10 mg; protective gas: nitrogen; gas flow fate: 10 mL/min; detection method: equilibration at 25° C., humidity: 0%, isothermal treatment: 90 min, weight change to be detected: from 0% RH to 80% RH;

Criterion: non-hygroscopic: no more than 0.2%; slightly hygroscopic: more than 0.2%, but no more than 2.0%; easily hygroscopic: higher than 2%, but no higher than 15%; extremely easily hygroscopic: higher than 15%.

(5) Hot Stage Polarized Light Microscope (PLM), XP-500E; Shanghai Changfang Optical Instrument Co., Ltd.

(6) Determination of solubility: visual inspection method, comprising the following specific process: the known amount of sample is weighed at 25° C., added with a solvent gradually, stirred or supplemented with ultrasound until the sample is dissolved to clear visually; the amount of the consumed solvent is recorded. If the sample is still not dissolved at a specific concentration, its solubility is expressed as "<specific concentration";

Criterion: extremely easily soluble: greater than 1 g/mL; easily soluble: greater than 100 mg/mL but less than or equal to 1 g/mL; soluble: greater than 33.3 mg/mL but less than or equal to 100 mg/mL; more slightly soluble: greater than 10 mg/mL but less than or equal to 33.3 mg/mL; slightly soluble: greater than 1 mg/mL but less than or equal to 10 mg/mL; extremely slightly dissolved: greater than 0.1 mg/mL, but less than or equal to 1 mg/mL; practically insoluble or insoluble: less than 0.1 mg/mL.

(7) Nuclear magnetic apparatus (NMR), Bruker Ascend 500; detection type: nuclear magnetic proton spectrum; full frequency excitation, spectral width: 30 ppm single pulse, 30° angle excitation scanning for 16 times, digital orthogonal detection, temperature control: 298K.

(8) High Performance Liquid Chromatography (HPLC), Ultimate 3000; test purpose: solubility test (area method), related substances (area normalization method).

The method parameters are as follows:

Chromatographic column: Shimadzu shim-pack VP-ODS (150 L*4.6), Waters symmetry C18 (3.9*150 mm 5 μm); column temperature: 25° C.; flow rate: 1.0 mL/min; detection wavelength: 214 nm; injection volume: 10 μL; running time: 20 min; Sample solvent: ACN; injection concentration: 0.2 mg/mL;

Mobile phase: Mobile phase A, $H_2O$:CAN:$H_3PO_4$=90:10:0.1, Mobile phase B: $H_2O$:CAN: $H_3PO_4$=10:90:0.1; the elution gradient is shown in Table 7 below:

TABLE 7

| Time (min) | A (%) | B (%) |
|---|---|---|
| 0 | 90 | 10 |
| 10 | 0 | 100 |
| 15 | 0 | 100 |
| 15.1 | 90 | 10 |
| 20 | Stop | |

In the following examples, "volatilizing the solvent" refers to natural volatilization of a solvent to dryness in an open vessel; "room temperature" means the temperature of 10 to 30° C. (30 to 70% RH); "crystal slurry" refers to a supersaturated solution of the compound of formula I described herein; "overnight" refers to the time spanning the evening, usually 10 to 16 hours.

In the following example tables, "NA" means "not applicable" or "not used."

Preparation Example

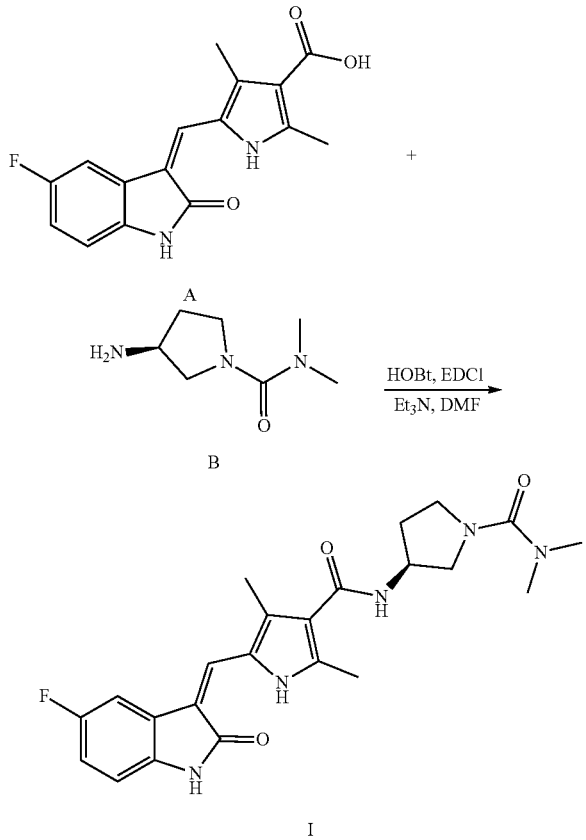

Compound A (13.00 kg, 1 eq.) was added to DMF (97.8 kg) in a reactor under nitrogen atmosphere at 20-30° C. Subsequently, triethylamine ("TEA", 21.88 kg, 5 eq.), hydroxybenzotriazole ("HOBt", 8.78 kg, 1.5 eq.), 1-ethyl-3-(3-dimethylaminopropyl)carbodiimide ("EDCI", 12.42 kg, 1.5 eq.) and Compound B (10.1 kg, 1.2 eq.) were added to the reactor under nitrogen atmosphere at 20-30° C. The mixture was stirred for 22 hours under nitrogen atmosphere at 20-30° C. After the reaction was completed, the reaction mixture was transferred to a clean container and weighed (163.8 kg).

About ¼ of the reaction mixture (40.90 kg) was added to a reactor, and then methyl tert-butyl ether ("MTBE", 62.8 kg) was added to the reaction mixture at 10-20° C. The resulting suspension was stirred at 10-20° C. for 2 hours and filtered. The remaining ¾ reaction solution was treated similarly. The filter cakes were combined and washed with MTBE (46.2 kg).

A portion of the combined solids (20.0 kg) was added to anhydrous methanol (74.2 kg) and the resulting mixture was heated to reflux for 45 minutes. Subsequently, the reaction mixture was cooled to 10-20° C. within 1-2 hours, and then continuously stirred at 10-20° C. for 1.5 hours. The resulting suspension was filtered. The other MTBE-washed materials were treated similarly. The filter cakes were combined and washed with cold methanol (44.2 kg). The wet crude product was dried under reduced pressure (500-1000 Pa) at 50° C. for 13 hours, and then dried at 76° C. for 23 hours to obtain about 12 kg of the initial product of the compound of formula I.

Example 1

Preparation Method 1 of the Crystalline Form 1 of the Compound of Formula I:

5 mg of the compound of formula I was mixed with a single solvent, or 10 mg of the compound of formula I was mixed with solvent 1 and solvent 2 to obtain a clear solution, which was naturally volatilized to dryness at the corresponding temperature to obtain crystalline form 1. The specific preparation parameters are shown in Table 8 below.

TABLE 8

| Temperature | Solvent 1 | Solvent 2 | Solvent 1/ Solvent 2 (mL) | Result analysis |
| --- | --- | --- | --- | --- |
| room temperature | methanol | NA | 1.0 | crystalline form 1 |
| 40° C. | methanol | NA | 1.0 | crystalline form 1 |
| room temperature | methanol | acetone | 0.2/0.4 | crystalline form 1 |
| 40° C. | methanol | water | 1.2/0.2 | crystalline form 1 |

Figure 2:
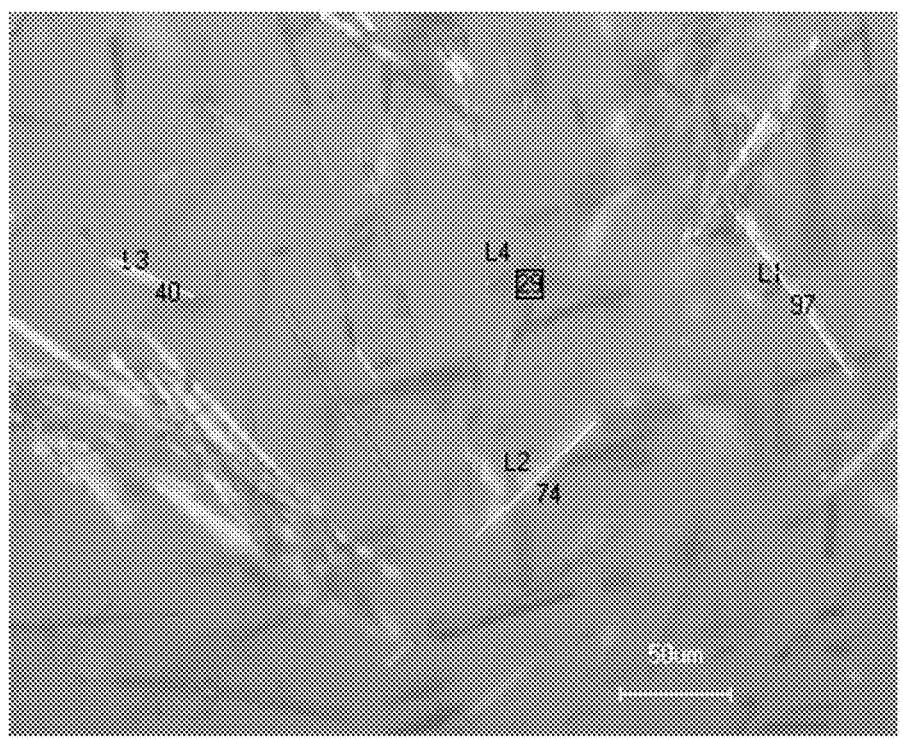
FIG. 2 shows the polarizing microscope photograph of the crystalline form 1.
Figure 3:
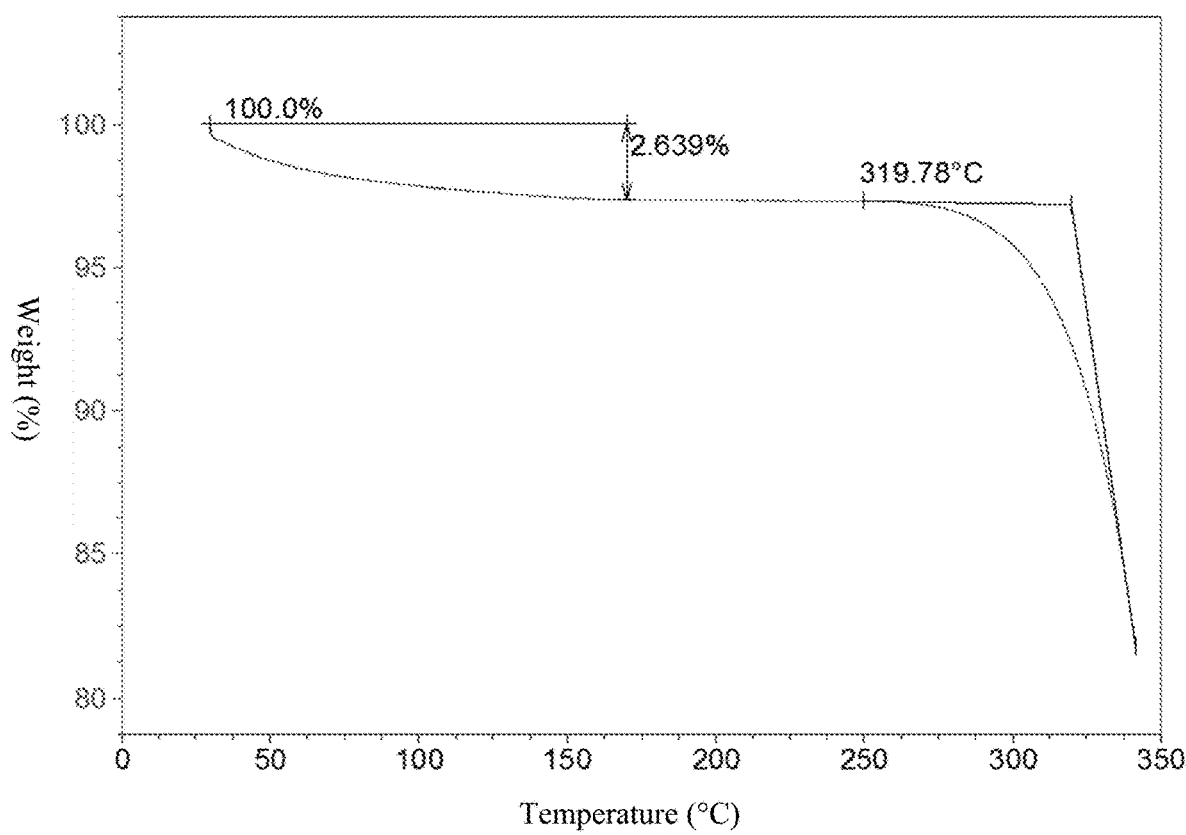
FIG. 3 shows the thermogravimetric analysis pattern of the crystalline form 1.
Figure 4:
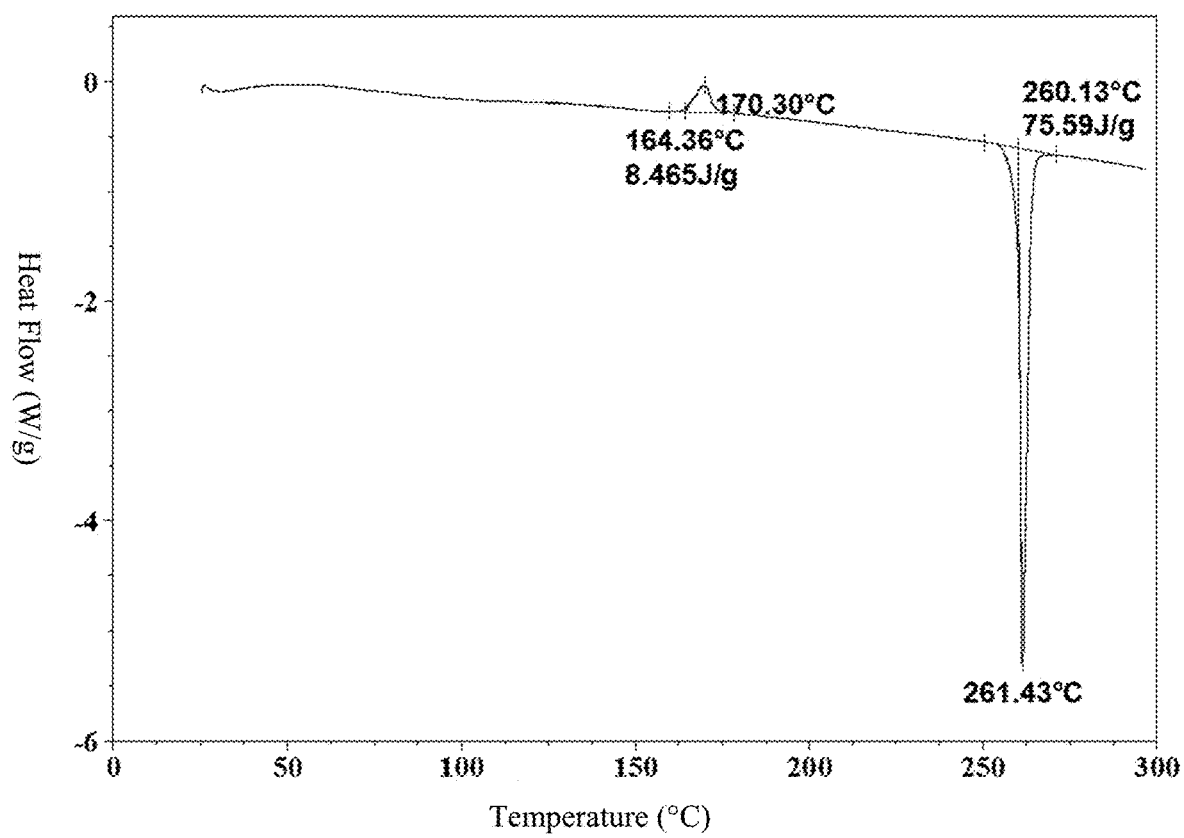
FIG. 4 shows the differential scanning calorimetry pattern of the crystalline form 1.
Figure 5:
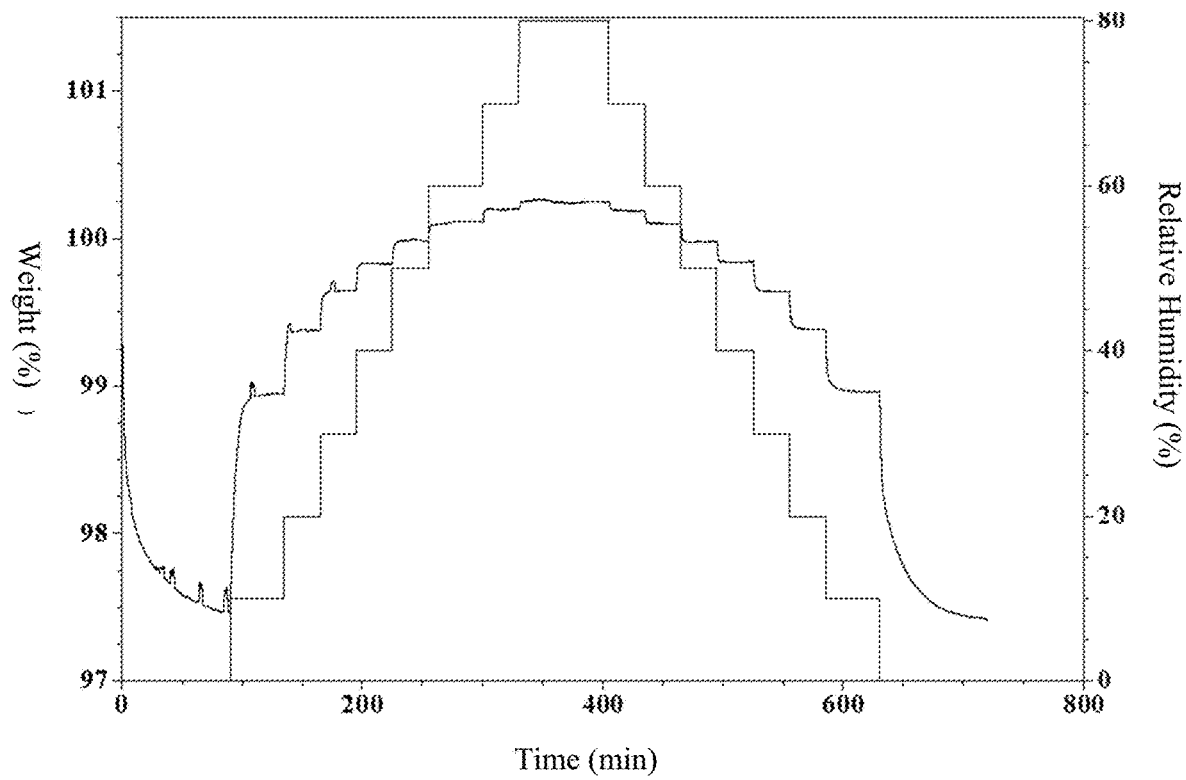
FIG. 5 shows the dynamic vapor sorption pattern of the crystalline form 1.

The products obtained by the above preparation methods are all found to be the crystalline form 1 by detection. The X-ray powder diffraction pattern of the crystalline form 1 is shown in FIG. 1 and the detailed data of the X-ray powder diffraction pattern thereof is shown in Table 1 above. The polarized light micrograph of crystalline form 1 is shown in FIG. 2, which shows that crystalline form 1 is a slender rod-like crystal. Crystalline form 1 has a thermogravimetric analysis pattern as shown in FIG. 3, which shows that crystalline form 1 has a weight loss of 2.6% before 170° C., which is an anhydrous substance with a decomposition temperature of about 320° C.; crystalline form 1 has the differential scanning calorimetry pattern shown in FIG. 4, which shows an exothermic peak at 150-170° C., confirmed by XRD as an exothermic peak of crystal transformation. Crystalline form 1 was transformed to crystalline form 3 and the melting point of crystalline form 1 is 260° C. Crystalline form 1 has a dynamic moisture adsorption pattern as shown in FIG. 5, showing a weight change of 2.8% in the range of 0% RH to 80% RH.

Figure 6:
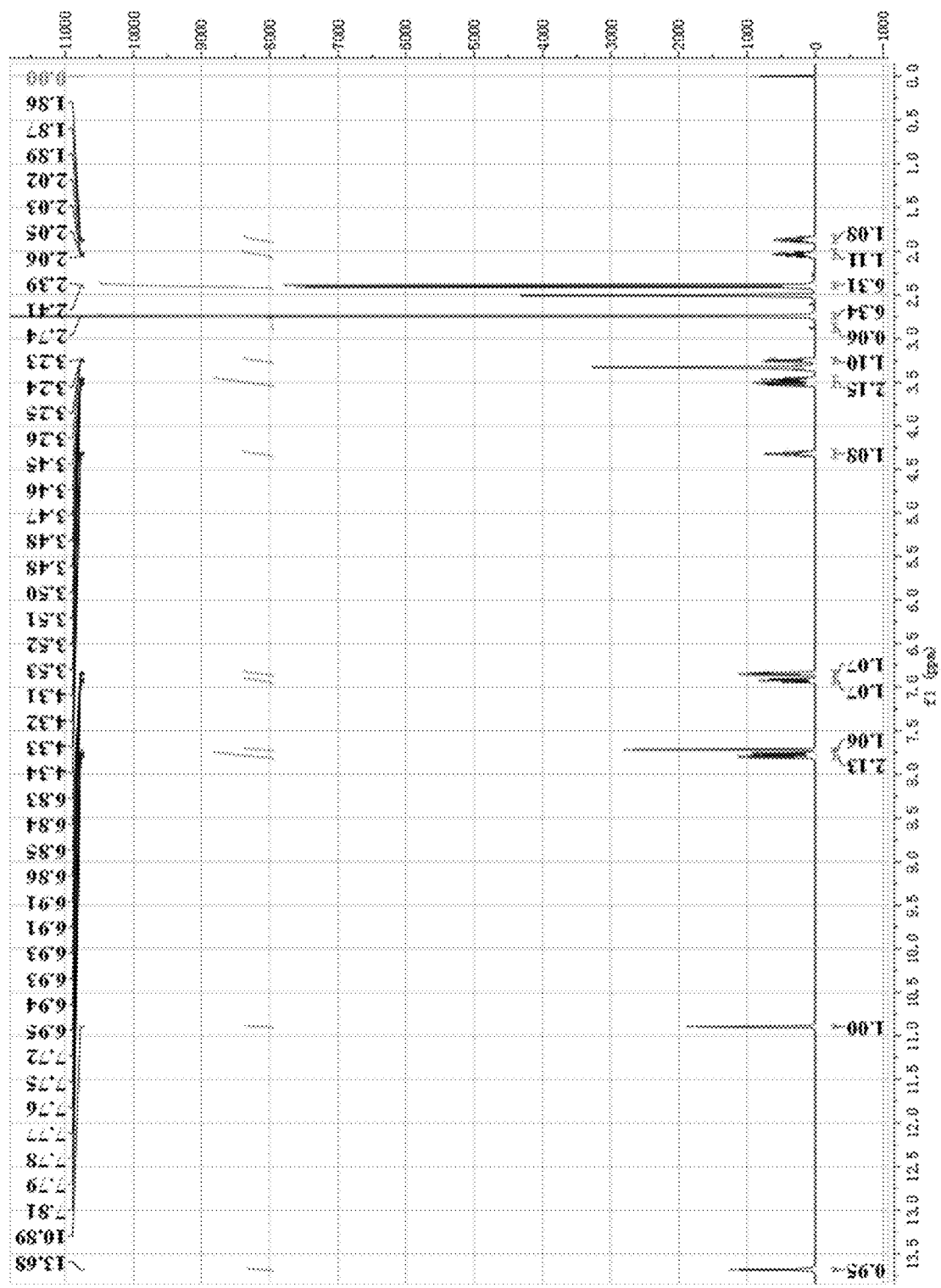
FIG. 6 shows the $^1$H-NMR spectrum of the compound of formula I of the present invention. Furthermore, all the $^1$H-NMR spectrum of the samples of crystalline forms 1, 2, 3, 5, 6 and 7 are consistent with FIG. 6.

The $^1$H-NMR spectrum of the compound of formula I and the crystalline form 1 is shown in FIG. 6, indicating that the chemical structure is shown in formula I:

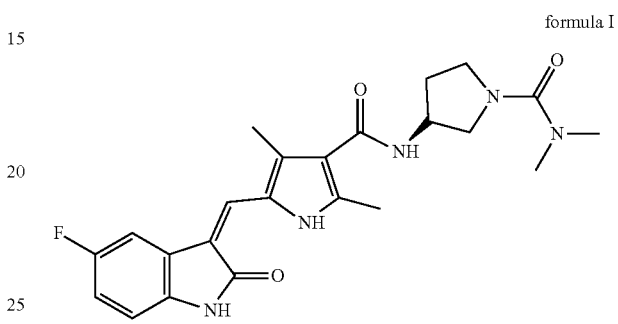

formula I

The results of solubility test showed that the solubility of the crystalline form 1 in conventional solvents at 25° C. is as follows: the solubility in methanol was 5 to 12.5 mg/mL; the solubility in ethanol was 1 to 2.5 mg/mL; the solubility in water was <1 mg/mL; the solubility in acetone was 1 to 2.5 mg/mL; the solubility in ethyl acetate was <1 mg/mL; the solubility in methyl tert-butyl ether was <1 mg/mL; the solubility in tetrahydrofuran was 1 to 2.5 mg/mL; the solubility in acetonitrile was <1 mg/mL; the solubility in toluene was <1 mg/mL; the solubility in n-heptane was <1 mg/mL.

Example 2

Preparation method 2 and preparation method 3 of crystalline form 1 of the compound of formula I:

20 mg of the compound of the formula I was mixed with 1.4 mL of methanol, heated to 50° C. to dissolve, and then hot filtered to obtain a clear solution. The operation of adding the solvent 2 to the dissolved solution under stirring was recorded as a positive addition (corresponding to the preparation method 2) and the operation of adding the clear solution to the solvent 2 under stirring was recorded as a reverse addition (corresponding to the preparation method 3). Stirring was continued once the solid was precipitated until the solid was completely precipitated to obtain the crystalline form 1. The specific preparation parameters are shown in Table 9 below.

TABLE 9

| Addition method | Solvent 1 | Solvent 2 | Solvent 1/ Solvent 2 (mL) | Result analysis |
| --- | --- | --- | --- | --- |
| positive addition | methanol | acetone | 1.4/3.0 | crystalline form 1 |
| positive addition | methanol | ethyl acetate | 1.4/3.0 | crystalline form 1 |
| positive addition | methanol | methyl tert-butyl ether | 1.4/3.0 | crystalline form 1 |

TABLE 9-continued

| Addition method | Solvent 1 | Solvent 2 | Solvent 1/ Solvent 2 (mL) | Result analysis |
|---|---|---|---|---|
| positive addition | methanol | acetonitrile | 1.4/3.0 | crystalline form 1 |
| reverse addition | methanol | water | 1.4/5.2 | crystalline form 1 |
| reverse addition | methanol | methyl tert-butyl ether | 1.4/11.2 | crystalline form 1 |

The products obtained by the above preparation methods were all found to be crystalline form 1 by detection, and the detection results of XRD, PLM, TGA, DSC, DVS, $^1$H-NMR and solubility were the same as in Example 1.

Example 3

Preparation Method 4 of Crystalline Form 1 of the Compound of Formula I:

20 mg of the compound of formula I was mixed with the corresponding solvent in a water bath at 50° C., and then filtered while hot to obtain a clear solution, which is naturally cooled to 4° C., stirred and crystallized to precipitate a solid product, so as to obtain the crystalline form 1. The specific preparation parameters are shown in table 10 below.

TABLE 10

| Crystallization temperature | Solvent 1 | Solvent 2 | Solvent 1/ Solvent 2(mL) | Result analysis |
|---|---|---|---|---|
| 4° C. | methanol | NA | 1.4 | crystalline form 1 |
| 4° C. | methanol | water | 1.4/0.4 | crystalline form 1 |
| 4° C. | methanol | ethyl acetate | 0.4/0.8 | crystalline form 1 |
| 4° C. | methanol | methyl tert-butyl ether | 0.8/1.4 | crystalline form 1 |
| 4° C. | methanol | acetonitrile | 0.4/0.4 | crystalline form 1 |

The products obtained by the above preparation methods were all found to be crystalline form 1 by detection, and the detection results of XRD, PLM, TGA, DSC, DVS, $^1$H-NMR and solubility were the same as in Example 1.

Example 4

Preparation Method 4 of Crystalline Form 1 of the Compound of Formula I:

The initial product of the compound of formula I (2.0 kg), anhydrous methanol (72.0 kg) and activated charcoal (0.20 kg) were added to a reactor and heated to reflux for 1.5 hours. The reaction solution was filtered and the filtrate was heated to reflux for 40 minutes. The resulting solution was hot filtered into a reactor and then concentrated under reduced pressure (500-1000 Pa) for about 4 hours to remove about 85 L of methanol. The resulting suspension was cooled to 10-20° C., stirred at 10-20° C. for about 45 minutes and then filtered. After the filter cake was washed with methanol, the purity was 99.9% detected by HPLC. The obtained solid was dried under reduced pressure (500-1000 Pa) at 40-60° C. The obtained product was detected as crystalline form 1 by XRD, with a yield over 80%.

Example 5

The preparation method of crystalline form 2 of the compound of formula I was as follows, wherein the crystalline form of the compound of formula I used below was crystalline form 1.

The preparation of No. 1 to 9 samples: 10 mg of the compound of formula I was mixed with the corresponding solvent to obtain a suspension, which was stirred at the corresponding temperature for 5 to 6 days. The crystal slurry was centrifuged and the solid was dried to obtain the samples.

The preparation of No. 10 sample: 199 mg of the compound of formula I was mixed with the corresponding solvent to obtain a suspension, which was stirred at 50° C. for 2 hours and then stirred at room temperature for 2 days. After the crystal slurry was filtered, the solid was dried under vacuum at room temperature overnight to obtain the sample.

The preparation of No. 11 sample: 200 mg of the compound of formula I was mixed with the corresponding solvent to obtain a suspension, which was stirred at 4° C. for 5 days. The crystal slurry was filtered and the solid was dried at room temperature under vacuum overnight to obtain the sample.

The preparation of No. 12 sample: 200 mg of the compound of formula I was mixed with the corresponding solvent to obtain a suspension, which was stirred at room temperature for 3 days. The crystal slurry was filtered and the solid was dried at room temperature under vacuum overnight to obtain the sample.

The specific preparation parameters are shown in table 11 below.

TABLE 11

| No. | Temperature | Solvent 1 | Solvent 2 | Solvent 1/ Solvent 2 (mL) | Result analysis |
|---|---|---|---|---|---|
| 1 | room temperature | water | NA | 0.5 | crystalline form 2 |
| 2 | 50° C. | ethyl acetate | NA | 0.5 | crystalline form 2 |
| 3 | 50° C. | toluene | NA | 0.5 | crystalline form 2 |
| 4 | room temperature | water | acetone | 0.2/0.4 | crystalline form 2 |
| 5 | room temperature | water | acetonitrile | 0.1/0.5 | crystalline form 2 |
| 6 | 50° C. | ethanol | toluene | 0.4/0.4 | crystalline form 2 |
| 7 | 50° C. | water | acetonitrile | 0.2/0.4 | crystalline form 2 |
| 8 | 4° C. | water | methanol | 0.4/0.4 | crystalline form 2 |
| 9 | — | ethyl acetate | NA | 5 | crystalline form 2 |
| 10 | 4° C. | water | methanol | 8/8 | crystalline form 2 |
| 11 | room temperature | water | acetonitrile | 2/10 | crystalline form 2 |

Figure 7:
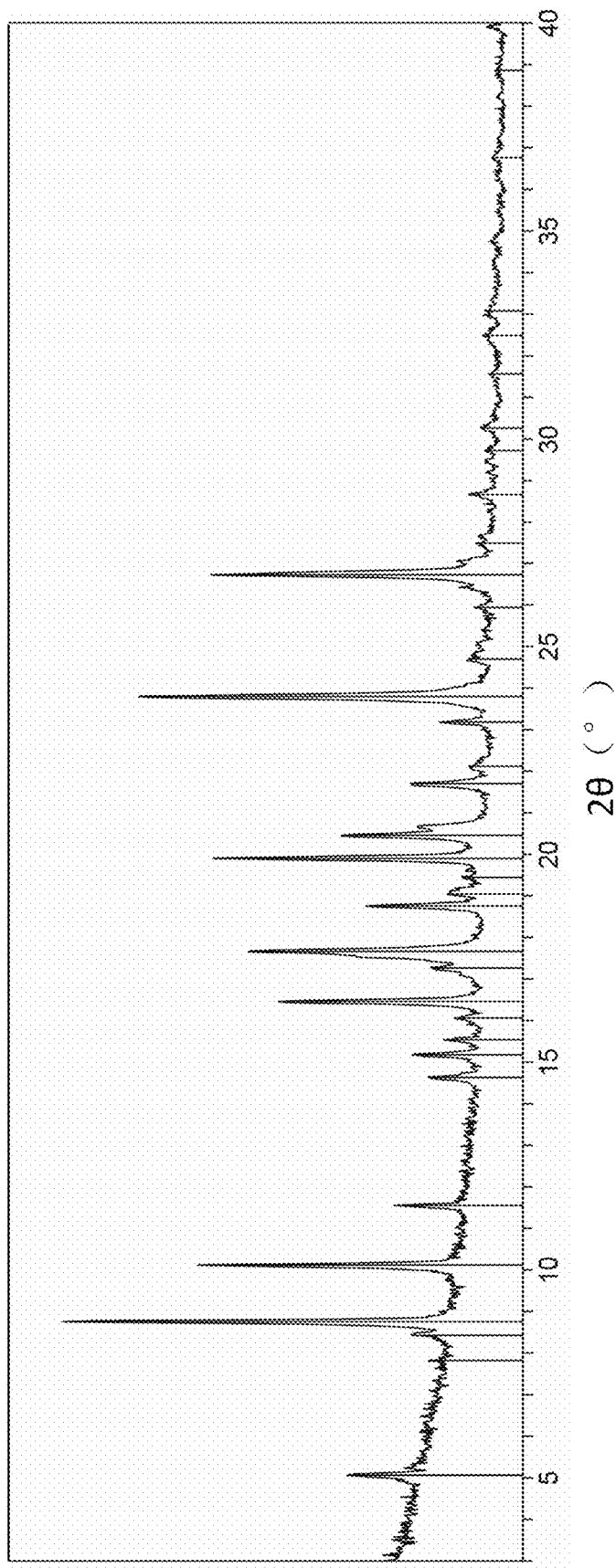
FIG. 7 shows the X-ray powder diffraction pattern of the crystalline form 2.
Figure 8:
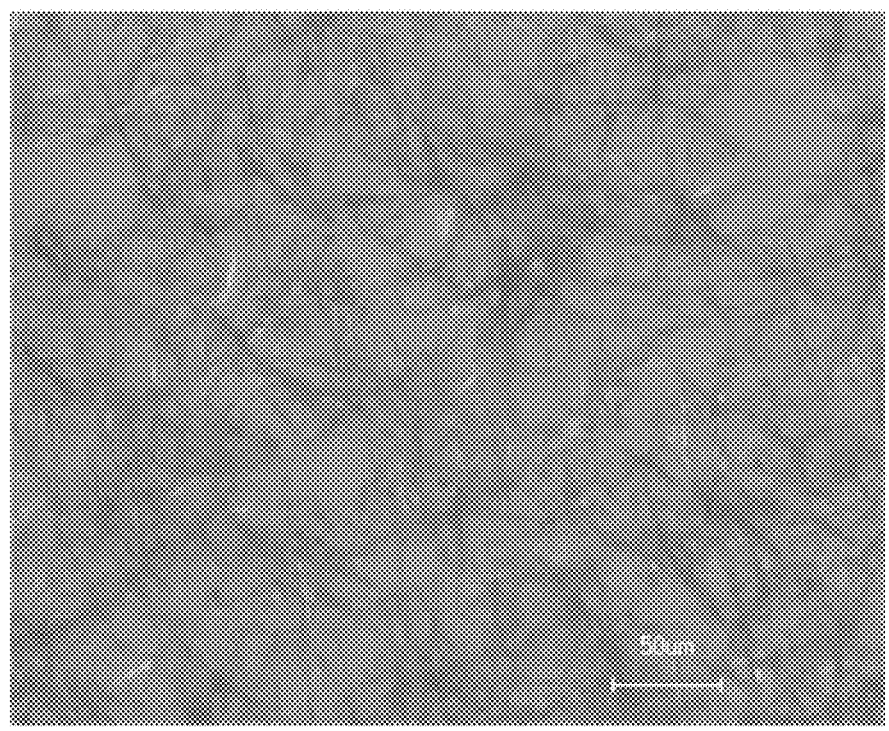
FIG. 8 shows the polarizing microscope photograph of the crystalline form 2.
Figure 9:
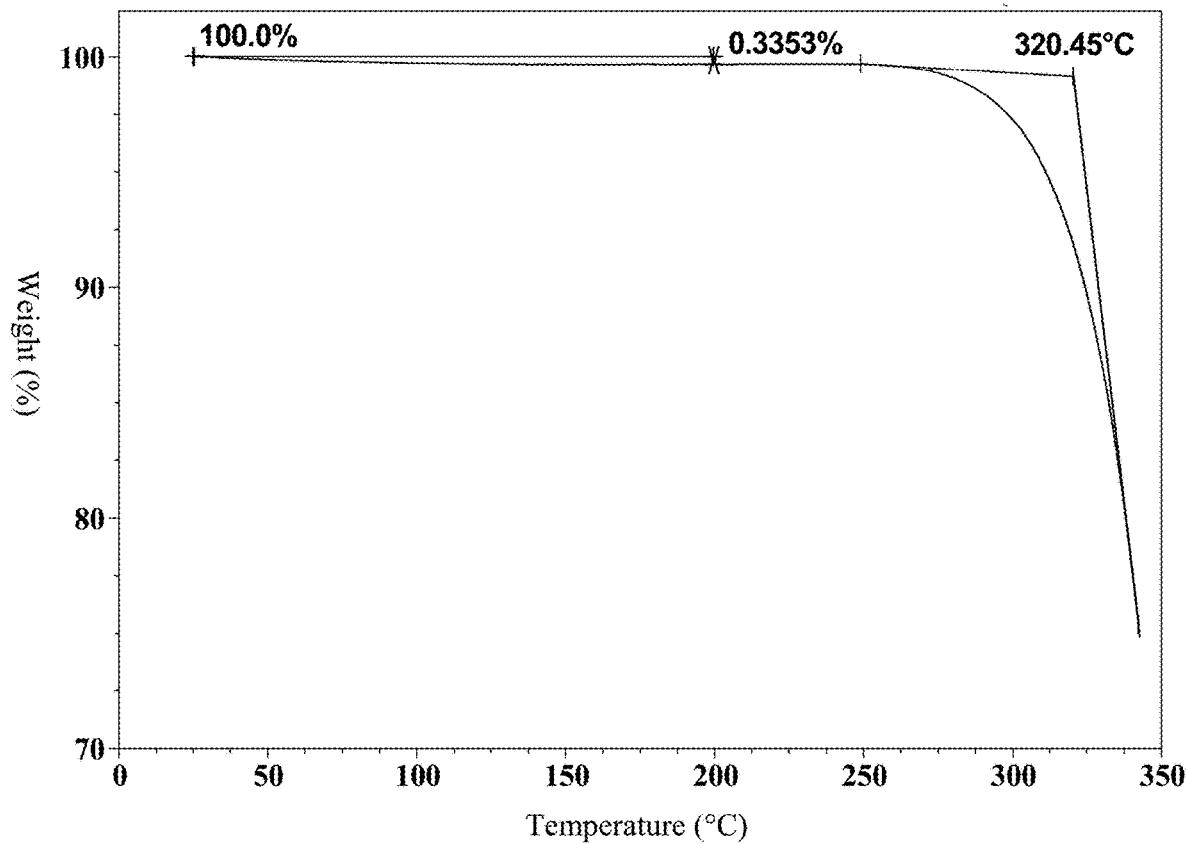
FIG. 9 shows the thermogravimetric analysis pattern of the crystalline form 2.
Figure 10:
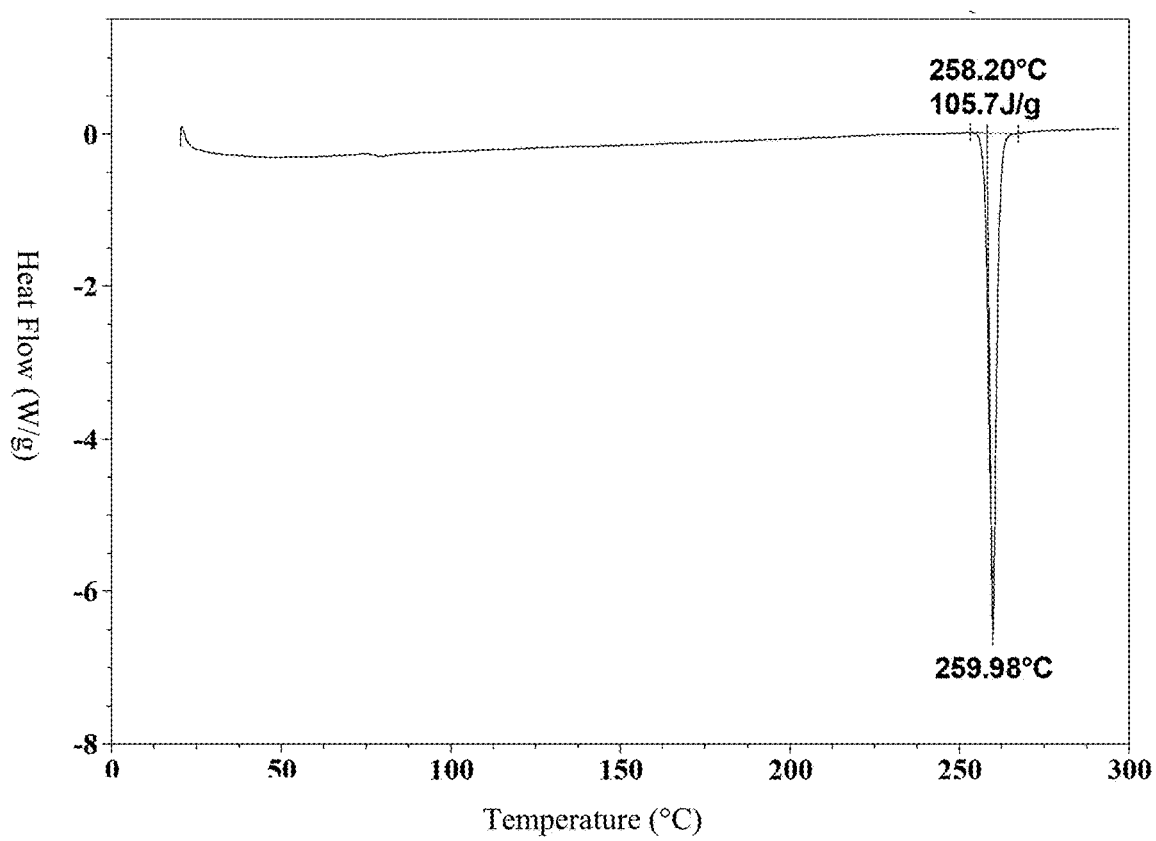
FIG. 10 shows the differential scanning calorimetry pattern of the crystalline form 2.
Figure 11:
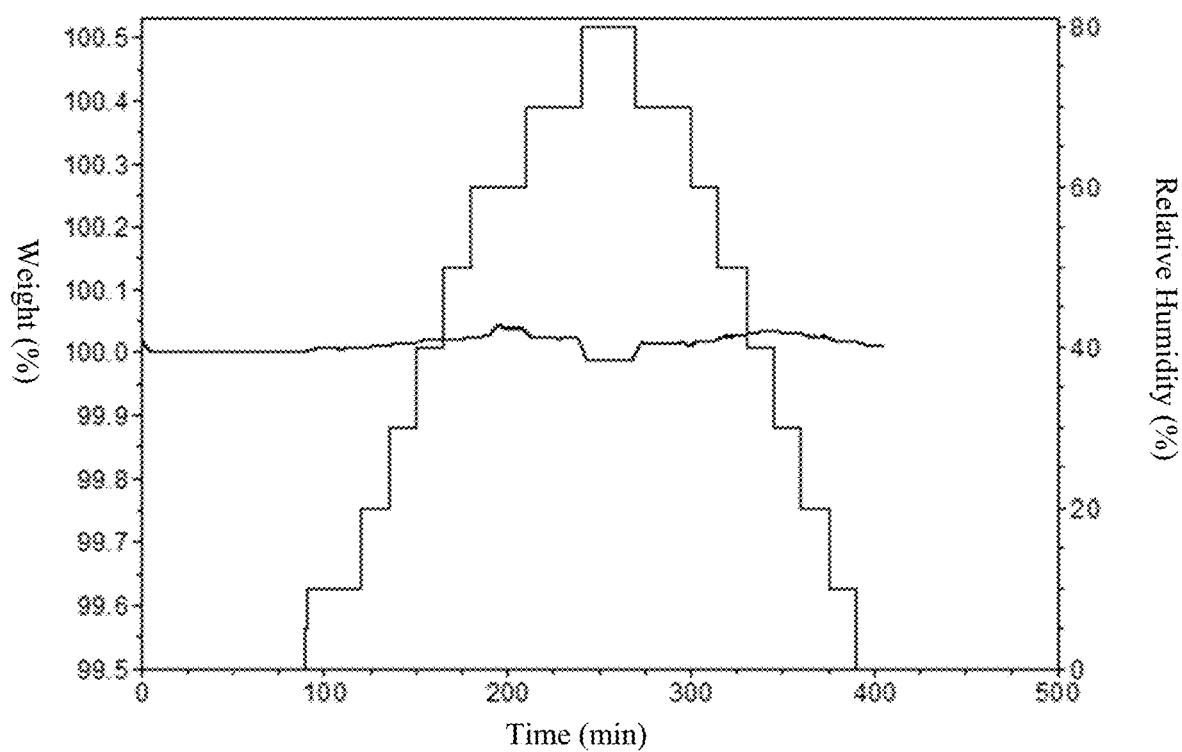
FIG. 11 shows the dynamic vapor sorption pattern of the crystalline form 2.

The products obtained by the above preparation methods were all found to be the crystalline form 2 by detection. The X-ray powder diffraction pattern of the crystalline form 2 is shown in FIG. 7 and the detailed data of the X-ray powder diffraction pattern thereof is shown in Table 2 above. The polarized light micrograph of crystalline form 2 is shown in FIG. 8, which shows that crystalline form 2 is a fine needle crystal. Crystalline form 2 has a thermogravimetric analysis pattern as shown in FIG. 9, which shows that crystalline form 1 has a weight loss of 0.3% before 200° C., which is an anhydrous substance with a decomposition temperature of 320° C. Further, the crystalline form 2 has a differential scanning calorimetry (DSC) pattern substantially as shown in FIG. 10, showing a melting point of the crystalline form 2 of 258° C. The crystalline form 2 has a dynamic moisture adsorption pattern as shown in FIG. 11, showing a weight change of 0.05% in the range of 0% RH to 80% RH. The $^1$H-NMR spectrum of the crystal form 2 is consistent with FIG. 6.

Example 6

Preparation Methods 1, 2 and 3 of the Crystalline Form 3 of the Compound of Formula I:

5 mg of the compound of formula I was mixed with a single solvent, or 10 mg of the compound of formula I was mixed with solvent 1 and solvent 2 to obtain a clear solution, which was naturally volatilized to dryness at the corresponding temperature, so as to obtain the crystalline form 3. The specific preparation parameters are shown in Table 12 below.

TABLE 12

| Preparation method | Temperature | Solvent 1 | Solvent 2 | Solvent 1/ Solvent 2 (mL) | Result analysis |
|---|---|---|---|---|---|
| preparation method 2 | room temperature | ethanol | NA | 3.0 | crystalline form 3 |
| preparation method 1 | room temperature | tetrahydrofuran | NA | 5.0 | crystalline form 3 |
| preparation method 1 | 40° C. | tetrahydrofuran | NA | 5.0 | crystalline form 3 |
| preparation method 3 | 60° C. | ethanol | water | 1.0/0.2 | crystalline form 3 |

Figure 12:
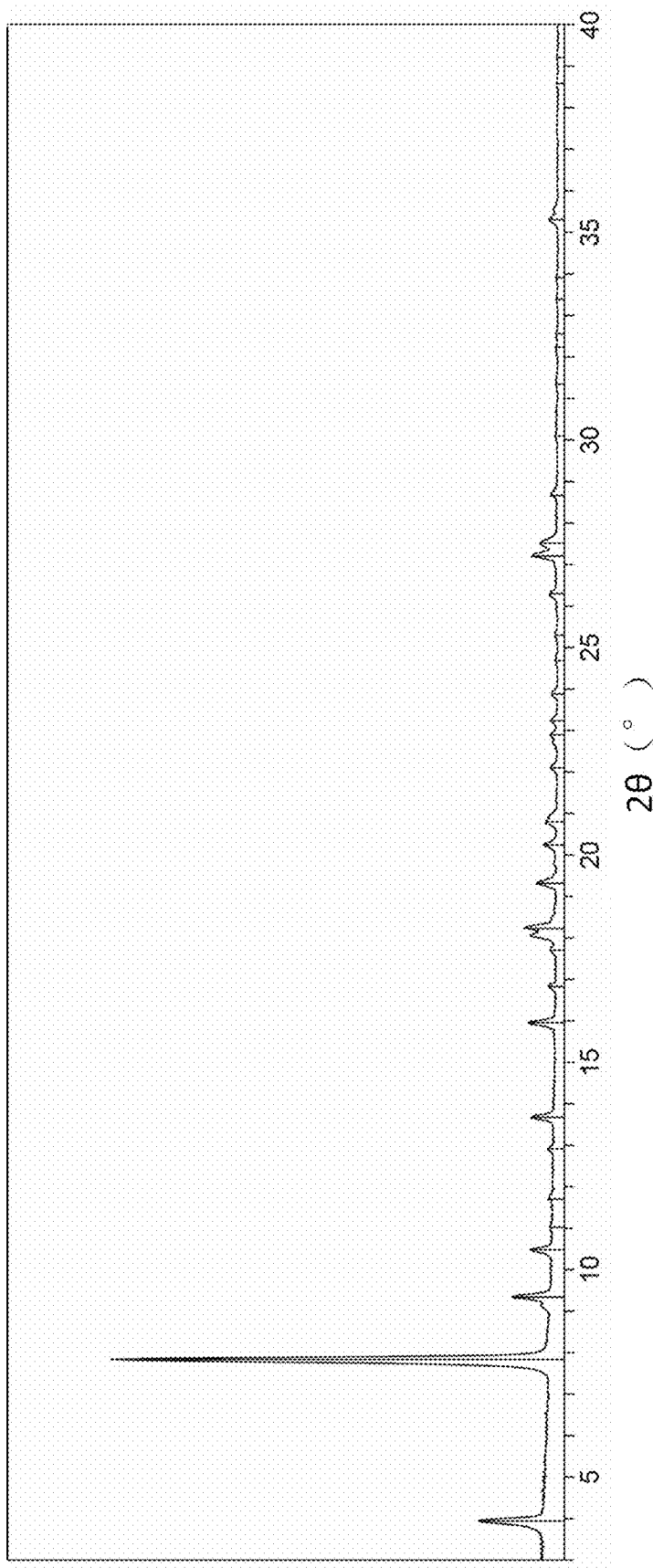
FIG. 12 shows the X-ray powder diffraction pattern of the crystalline form 3.
Figure 13:
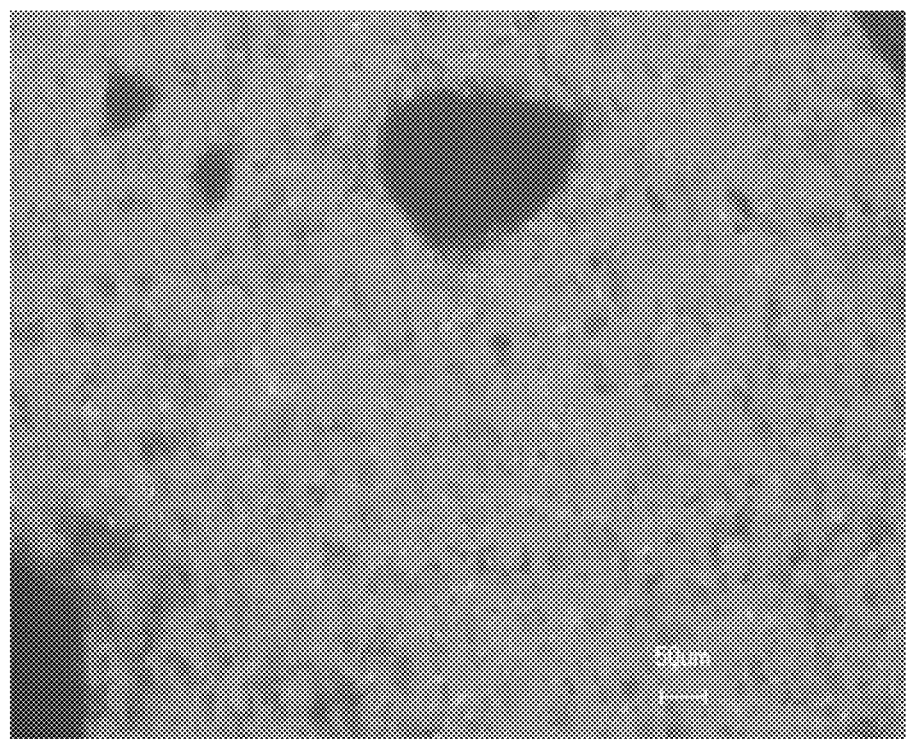
FIG. 13 shows the polarizing microscope photograph of the crystalline form 3.
Figure 14:
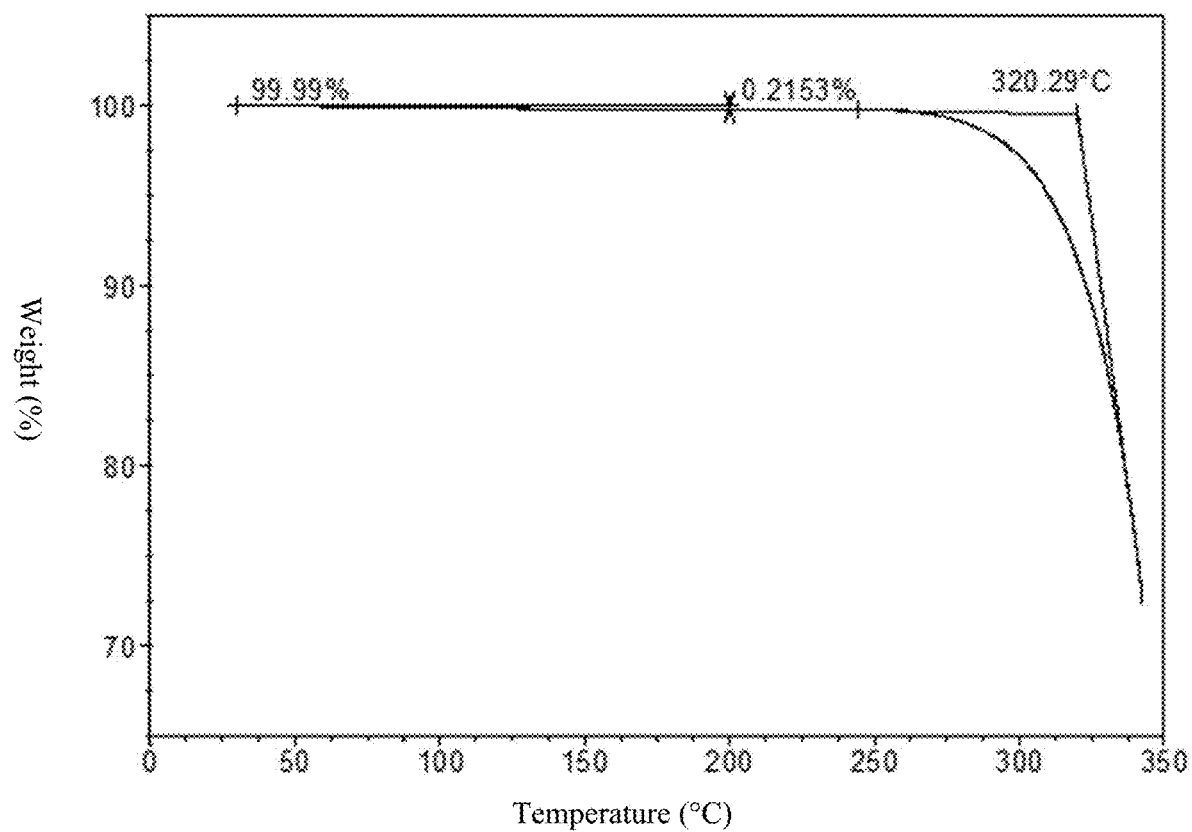
FIG. 14 shows the thermogravimetric analysis pattern of the crystalline form 3.
Figure 15:
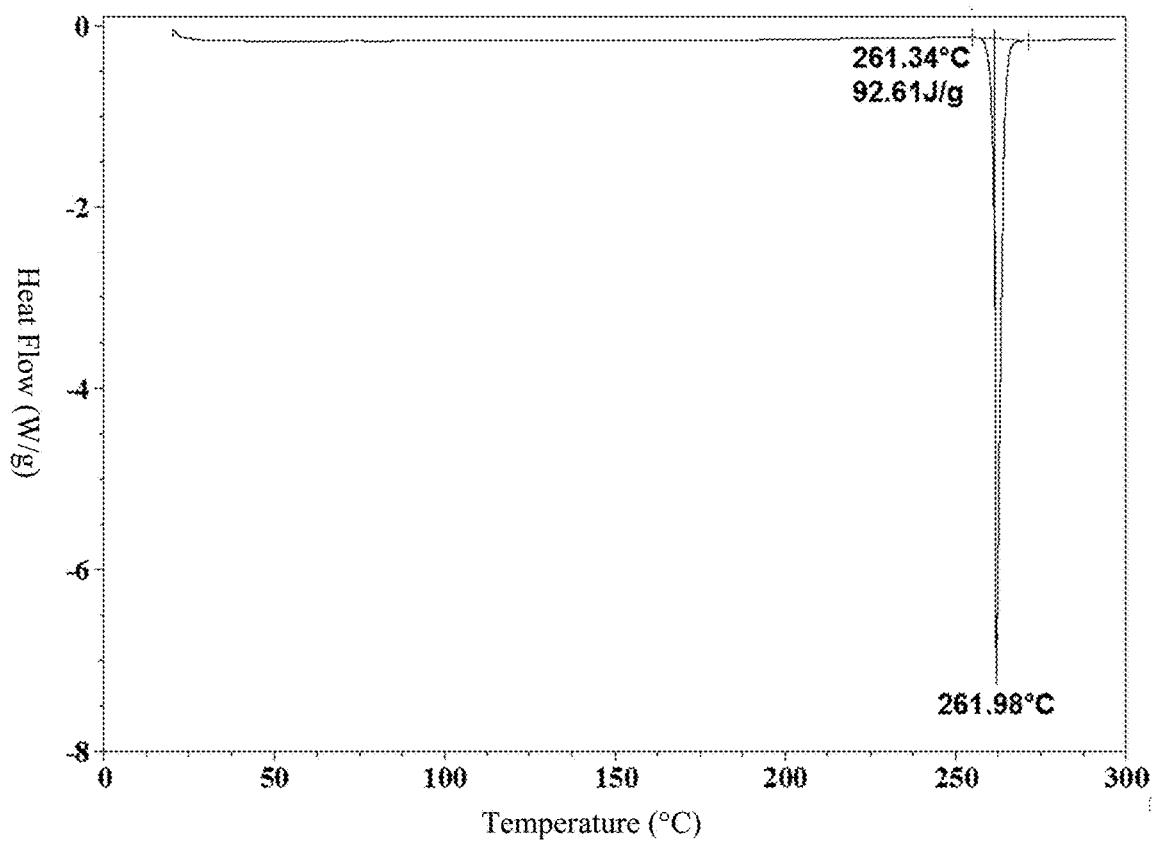
FIG. 15 shows the differential scanning calorimetry pattern of the crystalline form 3.
Figure 16:
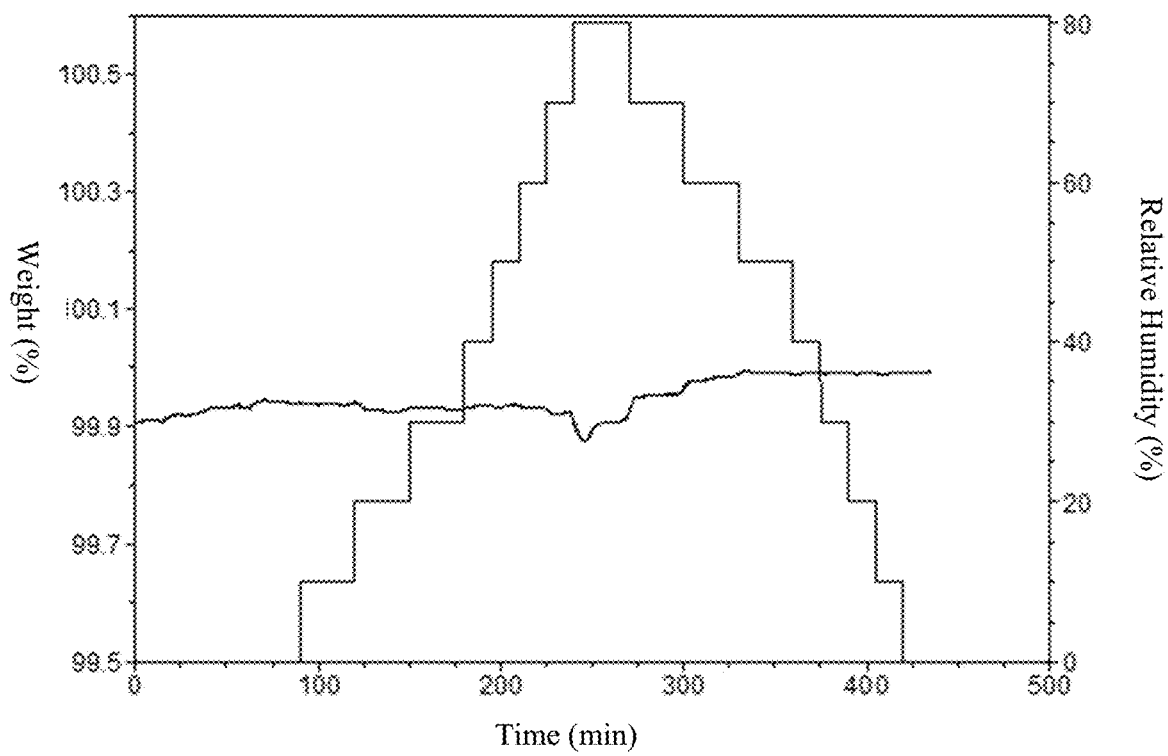
FIG. 16 shows the dynamic vapor sorption pattern of the crystalline form 3.

The products obtained by the above preparation methods were all found to be crystalline form 3 by detection. The X-ray powder diffraction pattern of crystalline form 3 is shown in FIG. 12 and the detailed data of the X-ray powder diffraction pattern thereof is shown in Table 3 above. The polarized light micrograph of crystalline form 3 is shown in FIG. 13, which shows that crystalline form 3 is fine particles. Crystalline form 3 has a thermogravimetric analysis pattern as shown in FIG. 14, which shows that crystalline form 3 has a weight loss of 0.2% before 200° C., which is an anhydrous substance with a decomposition temperature of 320° C. Moreover, the crystalline form 3 has a differential scanning calorimetry (DSC) pattern substantially as shown in FIG. 15, showing that the melting point of crystalline form 3 is 261° C. The crystalline form 3 has a dynamic moisture adsorption pattern as shown in FIG. 16, showing a weight change of 0.08% in the range of 0% RH to 80% RH. The $^1$H-NMR spectrum of crystalline form 3 is consistent with FIG. 6.

Example 7

The preparation method 4 of crystalline form 3 of the compound of formula I was as follows, wherein the crystalline form of the compound of formula I used below was the crystalline form 1.

The preparation of No. 1 to 3 samples: 10 mg of the compound of formula I was mixed with the corresponding solvent to obtain a suspension, which was stirred at the corresponding temperature for 5 to 6 days. The crystal slurry was centrifuged and the solid was dried to obtain the samples.

The preparation of No. 4 to 6 samples: 200 mg of the compound of formula I was mixed with the corresponding solvent to obtain a suspension, which was stirred at the corresponding temperature for 5 days. The crystal slurry was filtered and the solid was dried at room temperature under vacuum overnight to obtain the samples.

The preparation of No. 7 sample: 201.0 mg of the compound of formula I was mixed with the corresponding solvent to obtain a suspension, which was stirred at 800 rpm for 20 hours at the corresponding temperature. The crystal slurry was filtered and the solid was separated and dried at 60° C. for 1 hour to obtain the sample.

The specific preparation parameters are shown in Table 13 below.

TABLE 13

| No. | Temperature | Solvent 1 | Solvent 2 | Solvent 1/ Solvent 2 (mL) | Result analysis |
|---|---|---|---|---|---|
| 1 | room temperature | ethanol | NA | 0.5 | crystalline form 3 |
| 2 | 4° C. | acetone | NA | 0.5 | crystalline form 3 |
| 3 | room temperature | water | tetrahydrofuran | 0.4/0.4 | crystalline form 3 |
| 4 | room temperature | ethanol | NA | 8 | crystalline form 3 |
| 5 | 4° C. | acetone | NA | 8 | crystalline form 3 |
| 6 | room temperature | water | tetrahydrofuran | 5/5 | crystalline form 3 |
| 7 | room temperature | ethanol | NA | 15 | crystalline form 3 |

The products obtained by the above preparation methods were all found to be crystalline form 3 by detection, wherein the detection results of XRD, PLM, TGA, DSC, DVS, 1H-NMR and solubility were the same as in Example 4.

Example 8

Preparation Method 5 for Crystalline Form 3 of the Compound of Formula I:

20 mg of the compound of formula I was mixed with the corresponding solvent and dissolved in a water bath at 50° C., and then hot filtered to obtain a clear solution, which was naturally cooled to 4° C., stirred and crystallized to precipitate a solid. The specific preparation parameters are shown in Table 14 below.

TABLE 14

| Crystallization temperature | Solvent 1 | Solvent 2 | Solvent 1/ Solvent 2(mL) | Result analysis |
|---|---|---|---|---|
| 4° C. | tetrahydrofuran | NA | 5 | crystalline form 3 |
| 4° C. | methanol | tetrahydrofuran | 0.2/0.2 | crystalline form 3 |

The products obtained by the above preparation methods were all found to be crystalline form 3 by detection, wherein the detection results of XRD, PLM, TGA, DSC, DVS, 1H-NMR and solubility were the same as in Example 4.

Example 9

Preparation Method 6 for Crystalline Form 3 of the Compound of Formula I:

The crystalline form 1 was heated to 180° C. and cooled to room temperature to obtain the crystalline form 3.

The product obtained by the above preparation method was found to be the crystalline form 3 by detection, and the detection results of XRD, PLM, TGA, DSC, DVS, 1H-NMR and solubility was the same as in Example 4.

Example 10

Preparation Method 1 for Crystalline Form 5 of the Compound of Formula I:

20 mg of the compound of formula I was dissolved with 5 mL of acetone in a water bath at 50° C., then hot filtered to obtain a clear solution, which was naturally cooled to 4° C., stirred and crystallized to precipitated a solid. The mixture was centrifuged and dried at room temperature in vacuum to obtain the crystalline form 5.

Figure 17:
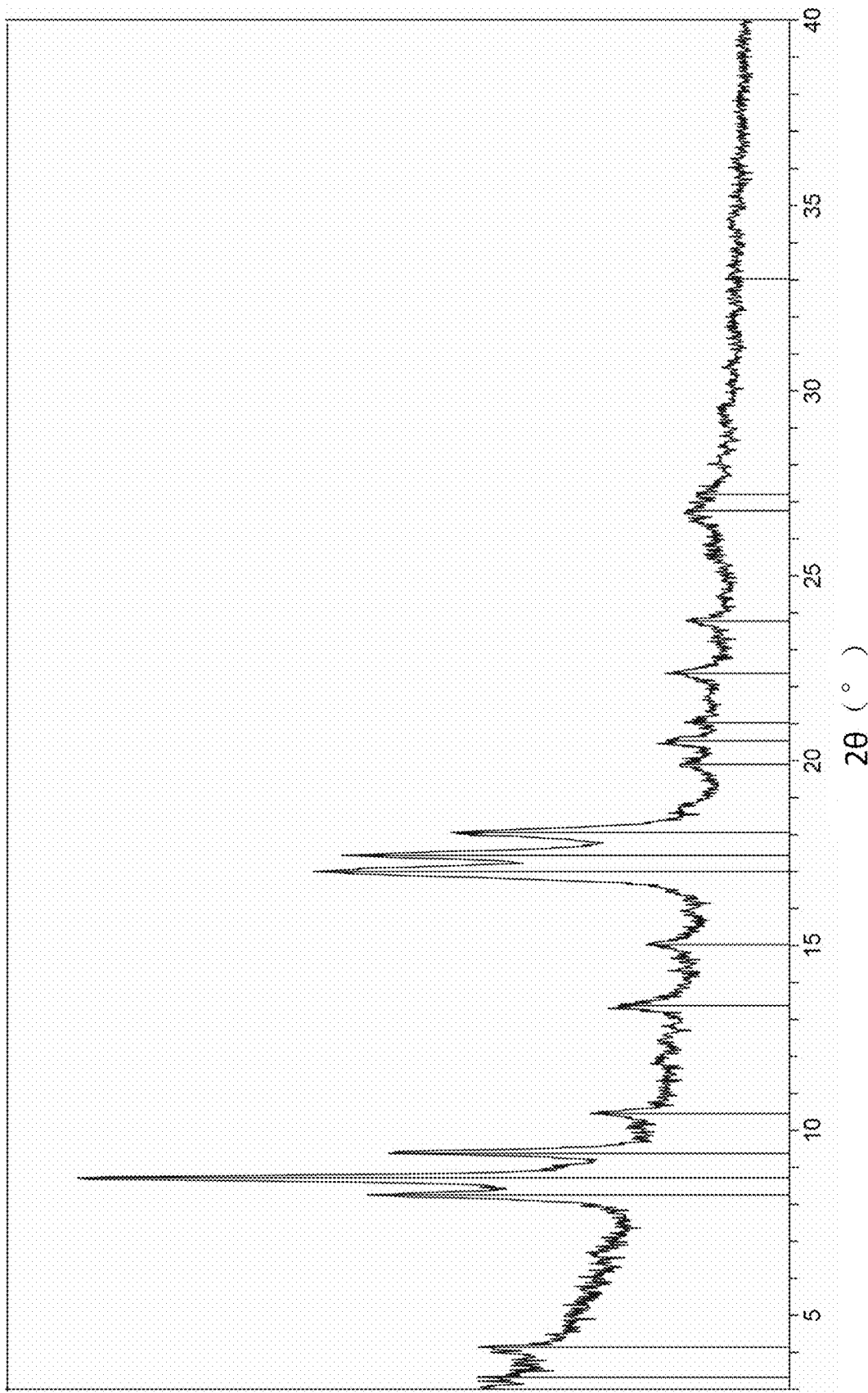
FIG. 17 shows the X-ray powder diffraction pattern of the crystalline form 5.
Figure 18:
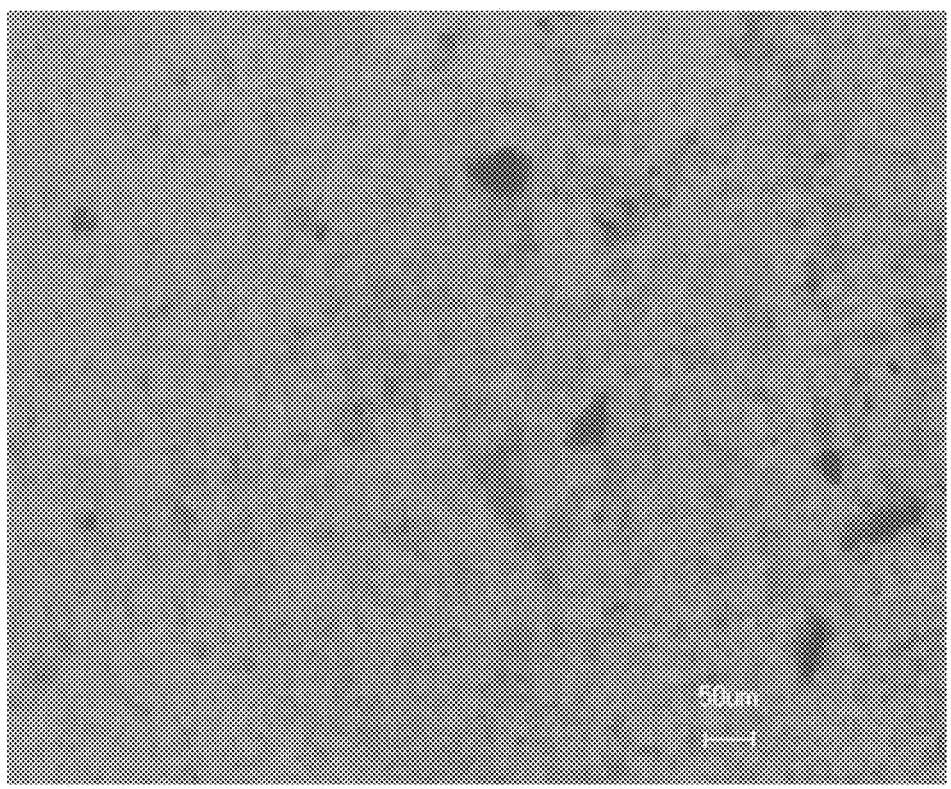
FIG. 18 shows the polarizing microscope photograph of the crystalline form 5.
Figure 19:
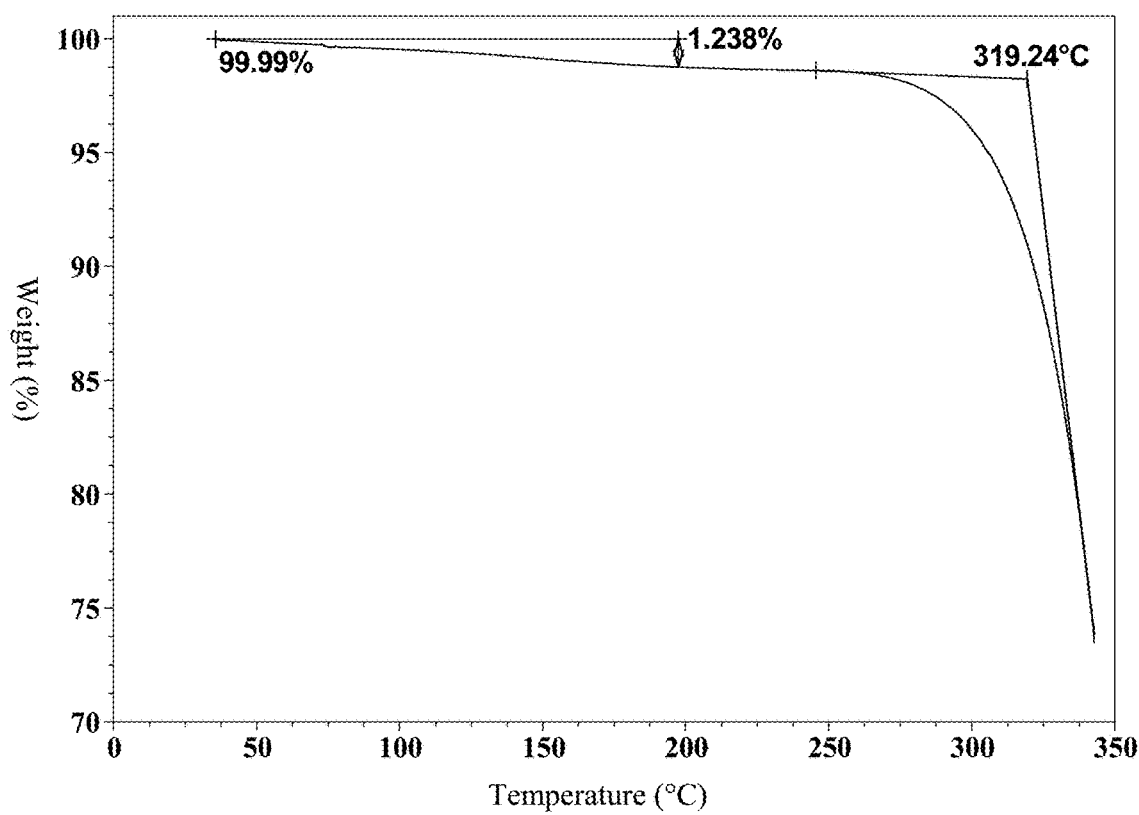
FIG. 19 shows the thermogravimetric analysis pattern of the crystalline form 5.
Figure 20:
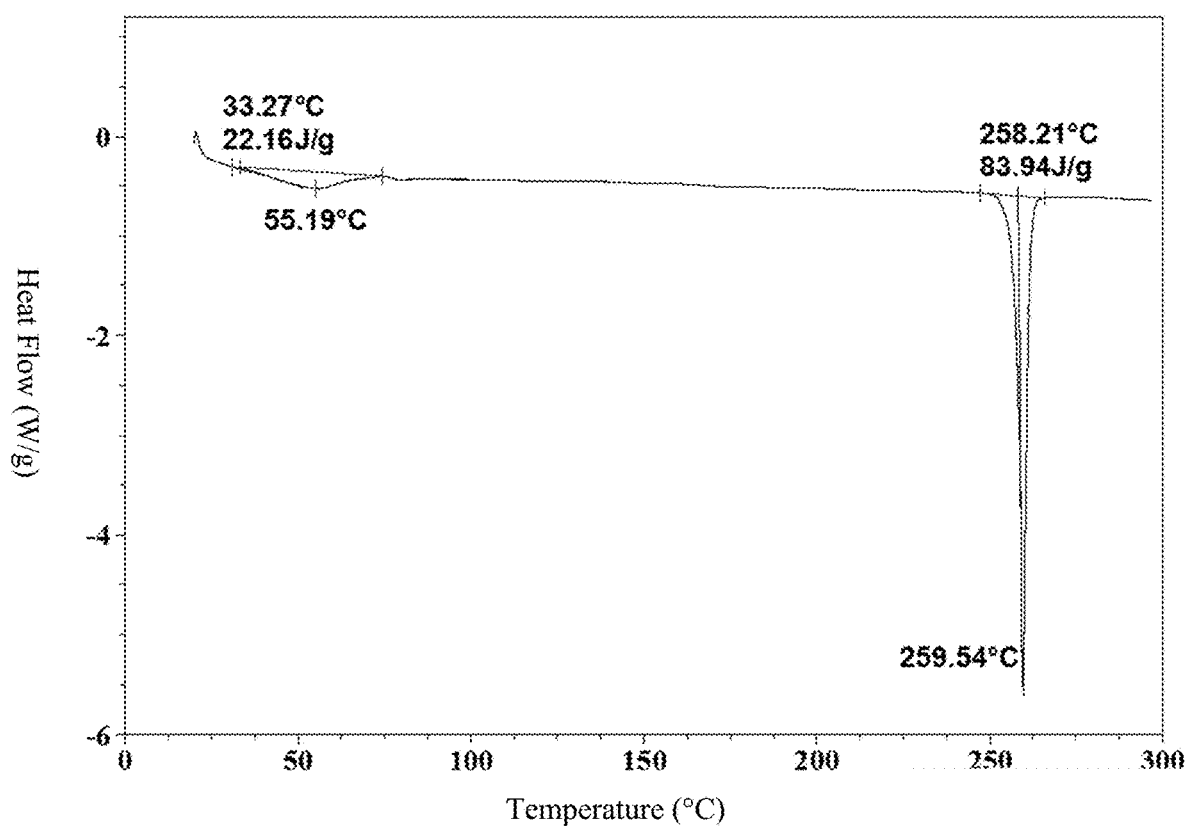
FIG. 20 shows the differential scanning calorimetry pattern of the crystalline form 5.
Figure 21:
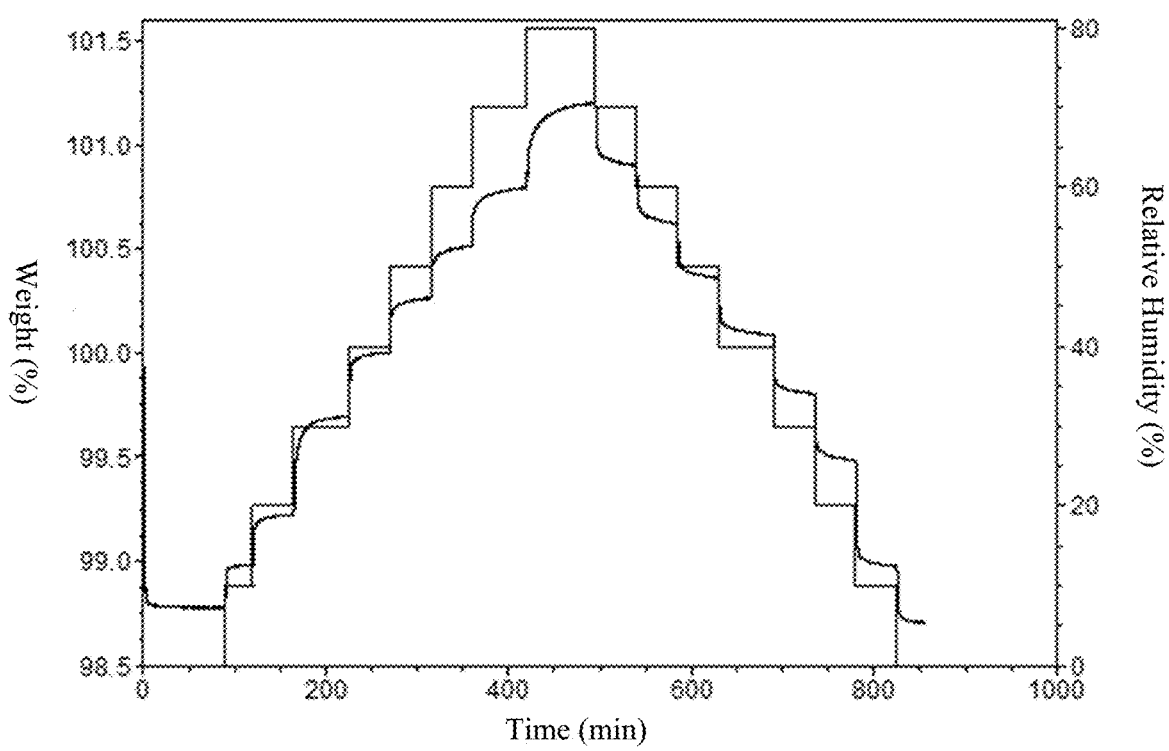
FIG. 21 shows the dynamic vapor sorption pattern of the crystalline form 5.

The product obtained by the above preparation method was found to be the crystalline form 5 by detection. The X-ray powder diffraction pattern of crystalline form 5 is shown in FIG. 17 and the detailed data of the X-ray powder diffraction pattern thereof is shown in Table 4 above. The polarized light micrograph of crystalline form 5 is shown in FIG. 18, which shows that crystalline form 5 is fine particles. Crystalline form 5 has a thermogravimetric analysis pattern as shown in FIG. 19, which shows that crystalline form 5 has a weight loss of 1.2% before 200° C., which is an anhydrous substance with a decomposition temperature of 319° C.; crystalline form 5 has a differential scanning calorimetry diagram as shown in FIG. 20, which shows that the melting point of crystalline form 5 is 258° C., and the broad endothermic peak before 100° C. is caused by the removal of the surface solvent. Moreover, the crystalline form 5 has a dynamic moisture adsorption diagram as shown in FIG. 21, showing a weight change of 2.5% in the range of 0% RH to 80% RH. The $^1$H-NMR spectrum of crystalline form 5 is consistent with FIG. 6.

Example 11

Preparation method 2 of crystalline form 5 of the compound of formula I was as follows. wherein the crystalline form of the compound of formula I used below was crystalline form 1.

Preparation of No. 1 sample: 199 mg of the compound of formula I was mixed with 10 ml of methyl t-butyl ether to obtain a suspension, which was stirred at room temperature for 2 days, and the crystal slurry was filtered, and the solid was dried under vacuum at room temperature overnight to obtain the sample.

Preparation of No. 2 sample: 600 mg of the compound of formula I was mixed with 30 ml of methyl t-butyl ether, added with the seed of crystalline form 5 of 2% of the crystal slurry mass, and stirred at room temperature for 1 day, and the crystal slurry was filtered. The solid was dried under vacuum at room temperature overnight to obtain the sample.

Preparation of No. 3 sample: The sample was prepared in the same manner as the preparation method of the No. 1 sample, only except that acetone was used instead of methyl tert-butyl ether.

The products obtained by the above preparation methods were all found to be crystalline form 5 by detection, wherein the detection results of XRD, PLM, TGA, DSC, DVS, $^1$H-NMR and solubility were the same as in Example 9.

Example 12

Preparation Method 1 of Crystalline Form 6 of the Compound of Formula I:

10 mg of the compound of the formula I and 0.4 mL was mixed with a mixture of toluene and methanol (volume ratio of toluene to methanol was 1:1), sonicated for dissolution and filtered to obtain a clear solution, which was naturally volatilized to dryness at room temperature to obtain the crystal.

Figure 22:
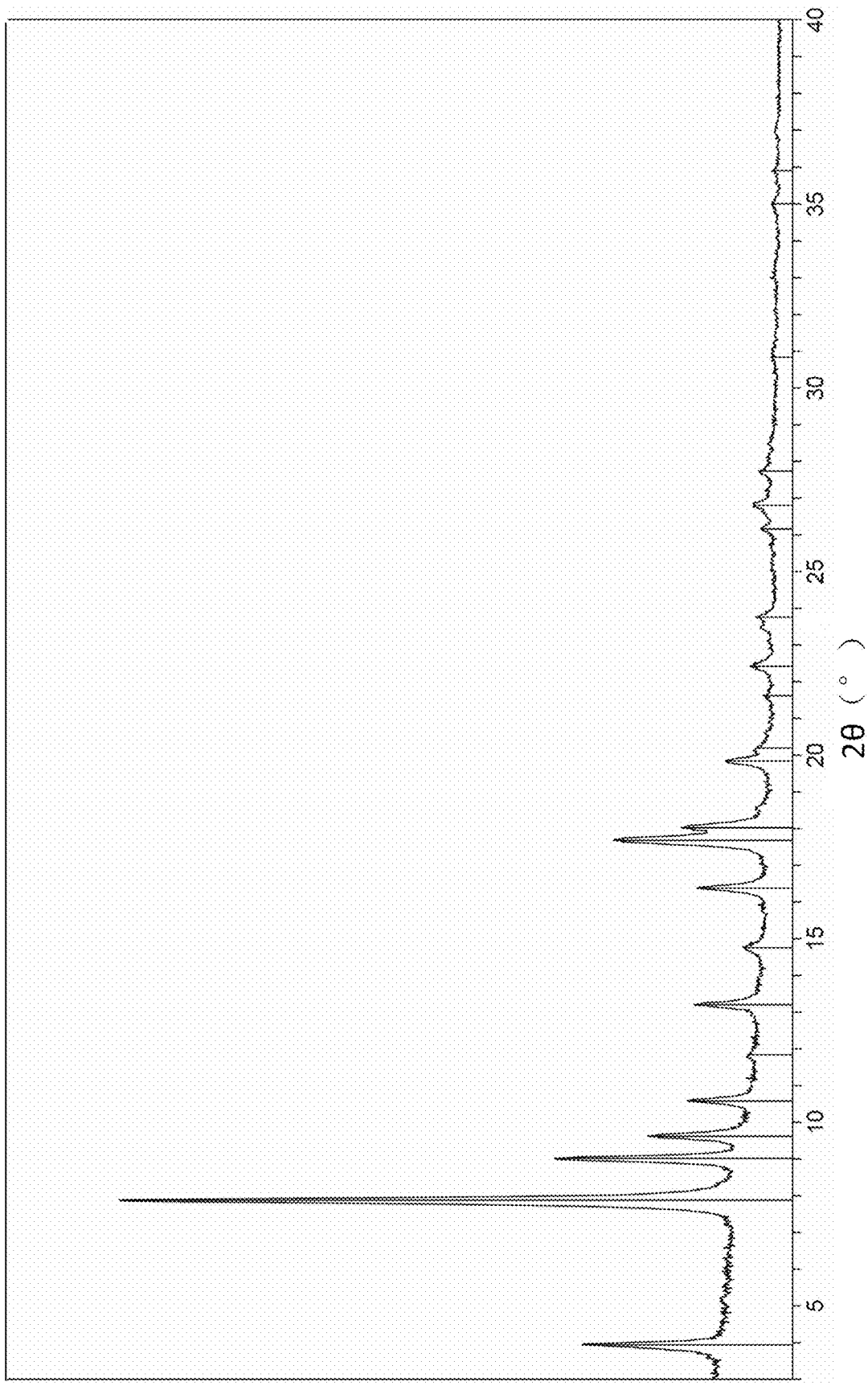
FIG. 22 shows the X-ray powder diffraction pattern of the crystalline form 6.
Figure 23:
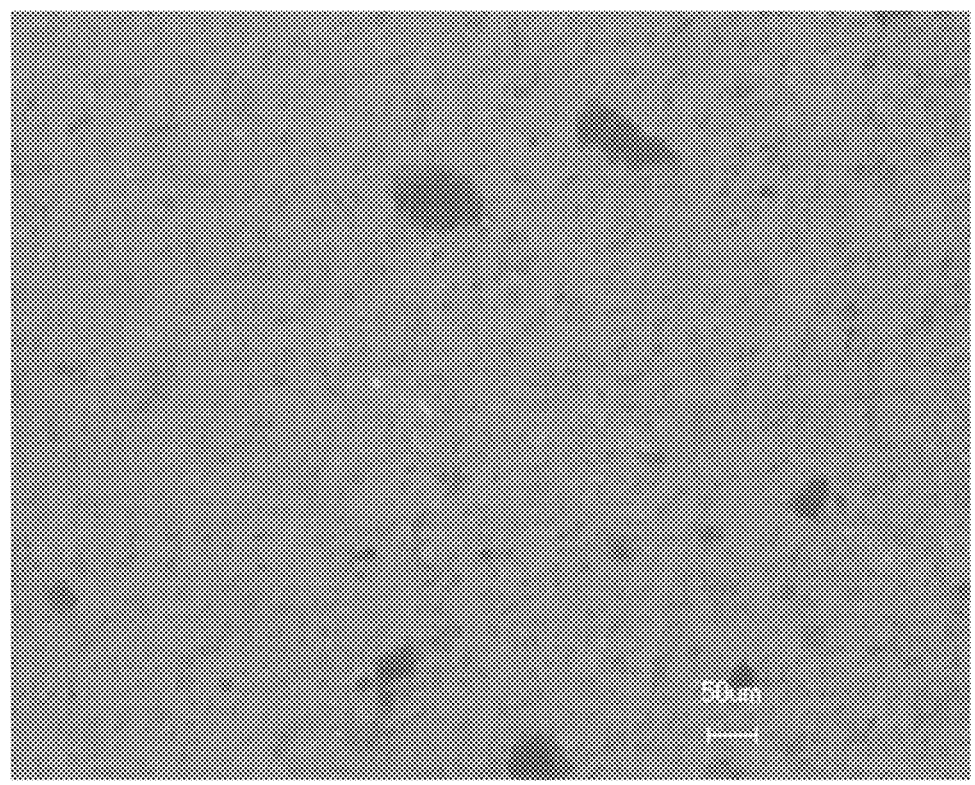
FIG. 23 shows the polarizing microscope photograph of the crystalline form 6.
Figure 24:
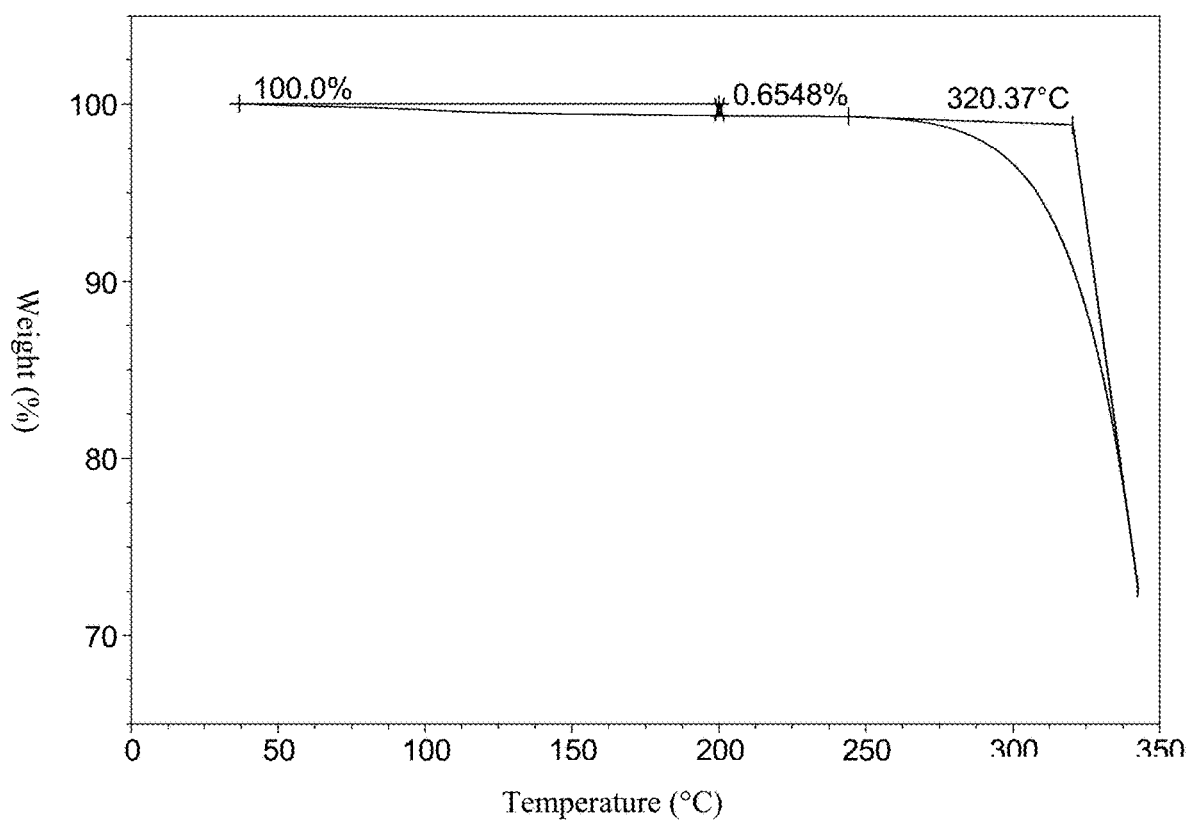
FIG. 24 shows the thermogravimetric analysis pattern of the crystalline form 6.
Figure 25:
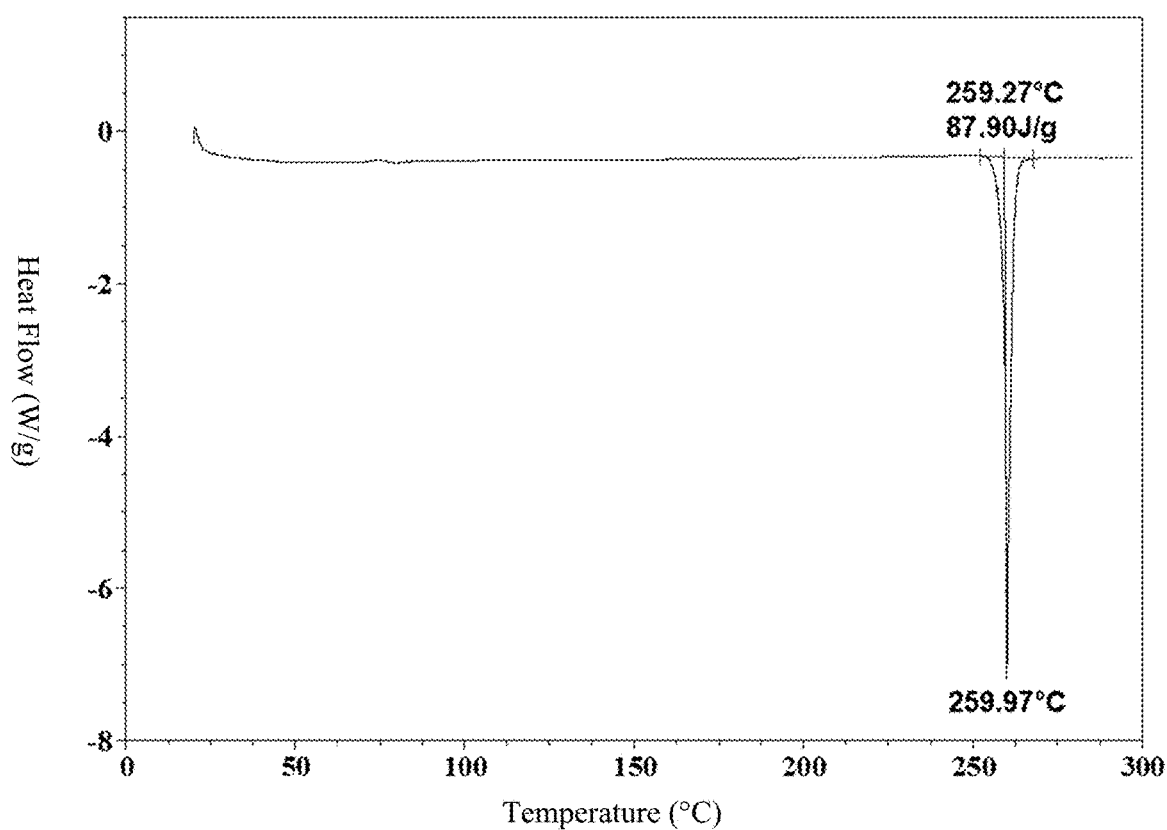
FIG. 25 shows the differential scanning calorimetry pattern of the crystalline form 6.
Figure 26:
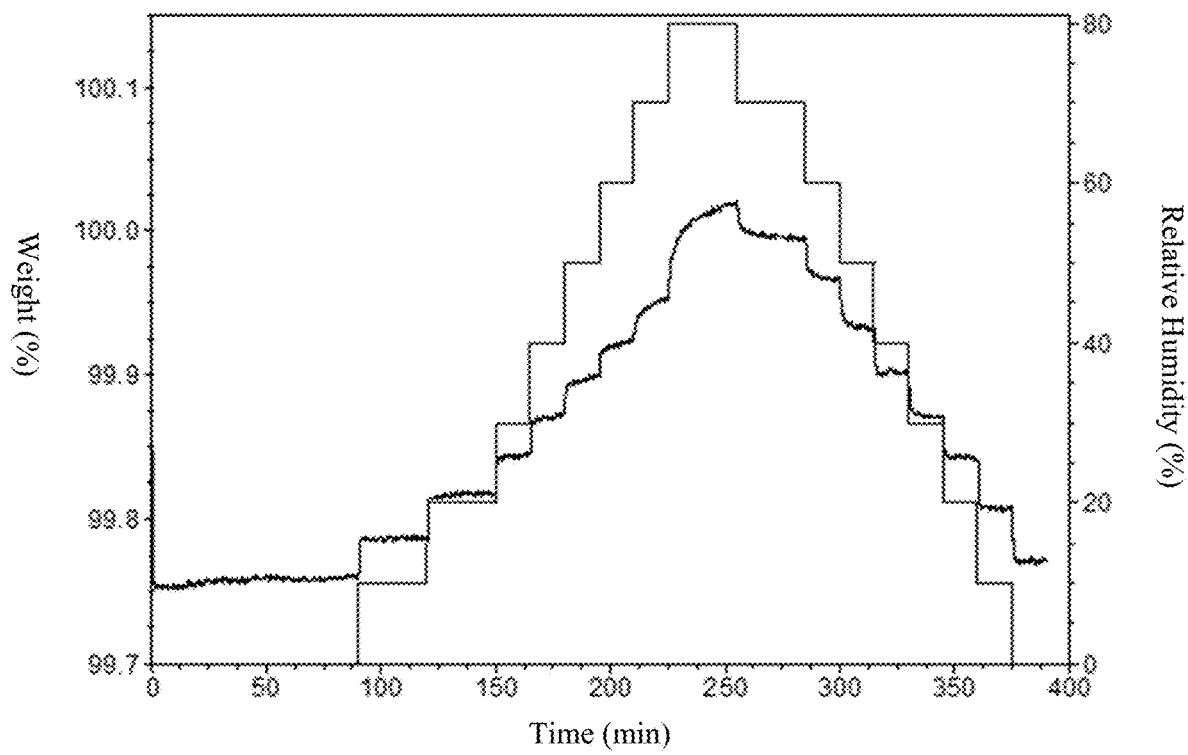
FIG. 26 shows the dynamic vapor sorption pattern of the crystalline form 6.

The product obtained by the above preparation method was found to be the crystalline form 6 by detection. The X-ray powder diffraction pattern of crystalline form 6 is shown in FIG. 22 and the detailed data of the X-ray powder diffraction pattern thereof is shown in Table 5 above. The polarized light micrograph of crystalline form 6 is shown in FIG. 23, which shows that crystalline form 6 is fine particles and partially agglomerated. Crystalline form 6 has a thermogravimetric analysis pattern as shown in FIG. 24, which shows that the crystalline form 6 has a weight loss of 0.7% before 200° C., which is an anhydrous substance with a decomposition temperature of 320° C.; crystalline form 6 has a differential scanning calorimetry diagram as shown in FIG. 25, which shows that the melting point of crystalline form 6 is 259° C. Moreover, the crystalline form 6 has a dynamic moisture adsorption diagram as shown in FIG. 26, showing a weight change of 0.26% in the range of 0% RH to 80% RH.

The $^1$H-NMR spectrum of crystalline form 6 is consistent to that of FIG. 6.

Example 13

Preparation Method 2 of Crystalline Form 6 of the Compound of Formula I:

Preparation of No. 1 sample: 20 mg of the compound of formula I was mixed with 1.4 mL of methanol, heated to 50° C. to dissolve, and then hot filtered to obtain a clear solution, and 3.0 mL of toluene was added to the solution under stirring. When the solid was precipitated, stirring was continued until the solid was completely precipitated to obtain the crystalline form 6.

Preparation of No. 2 sample: 20 mg of the compound of formula I was mixed with 1.4 mL of methanol, heated to 50° C. to dissolve, and then hot filtered to obtain a clear solution, and the clear solution was added to 11.2 ml of toluene under stirring. When the solid was precipitated, stirring was continued until the solid was completely precipitated.

The product obtained by the above preparation methods was all found to be crystalline form 6 by detection, wherein the detection results of XRD, PLM, TGA, DSC, DVS, 1H-NMR and solubility were the same as in Example 12.

Example 14

Preparation method 3 of crystalline form 6 of the compound of formula I, wherein the crystalline form of the compound of formula I used therein is the crystalline form 1.

Preparation of No. 1 sample: 200 mg of the compound of formula I was mixed with 20 mL of toluene, stirred at room temperature for 16-22 hours, and then the crystal slurry was dried under vacuum at 60° C. for 1 hour to obtain the sample.

Preparation of No. 2 sample: 600 mg of the compound of formula I was mixed with 60 mL of toluene, added with the seed of crystalline form 6 of 2% of the crystal slurry mass, and stirred at room temperature for 1 day, and then the crystal slurry was dried under vacuum at 50° C. for 1 hour to obtain the sample.

The products obtained by the above preparation methods were all found to be crystalline form 6 by detection, wherein the detection results of XRD, PLM, TGA, DSC, DVS, 1H-NMR and solubility were the same as in Example 11.

Further, in the preparation process of the No. 1 sample, a sample taken after the mixture was stirring at room temperature for 6 hours was found containing an agglomerate product after suction filtration. Additionally, the wet product was found comprising crystalline form 1 by detection.

Example 15

Preparation Method 1 of Crystalline Form 7 of the Compound of Formula I:

Preparation of No. 1 sample: 199 mg of the compound of formula I was mixed with 10 mL of ethyl acetate and stirred at 50° C. for 30 minutes. After filtration, the filter cake was dried under vacuum at 60° C. for 1 hour to obtain the sample.

Preparation of No. 2 sample: 600 mg of the compound of formula I was mixed with 30 mL of ethyl acetate and stirred at 50° C. for 30 minutes. After filtration, the filter cake was dried under vacuum at 60° C. for 1 hour.

Figure 27:
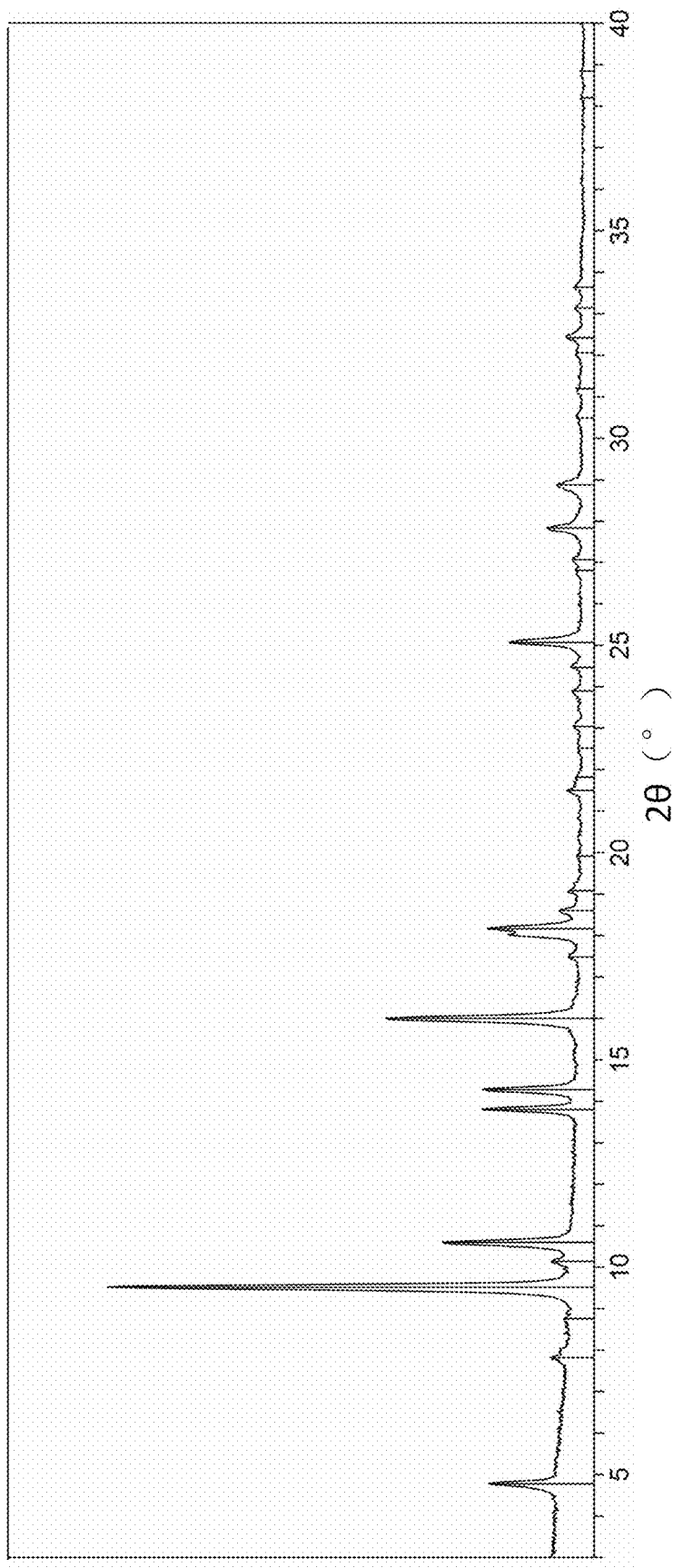
FIG. 27 shows the X-ray powder diffraction pattern of the crystalline form 7.
Figure 28:
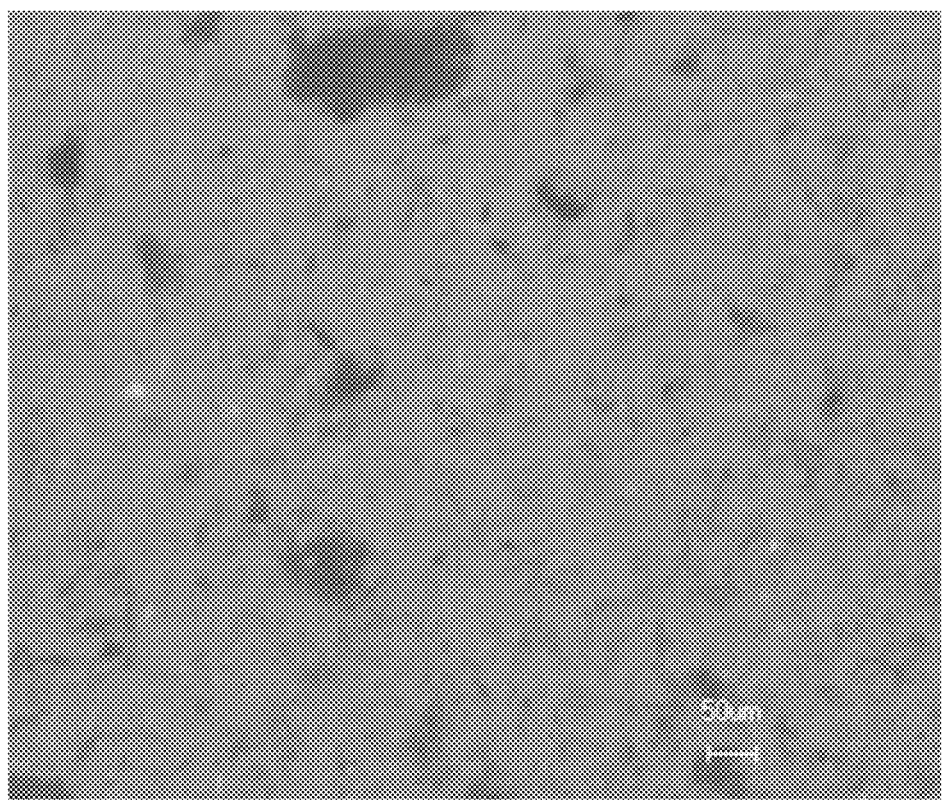
FIG. 28 shows the polarizing microscope photograph of the crystalline form 7.
Figure 29:
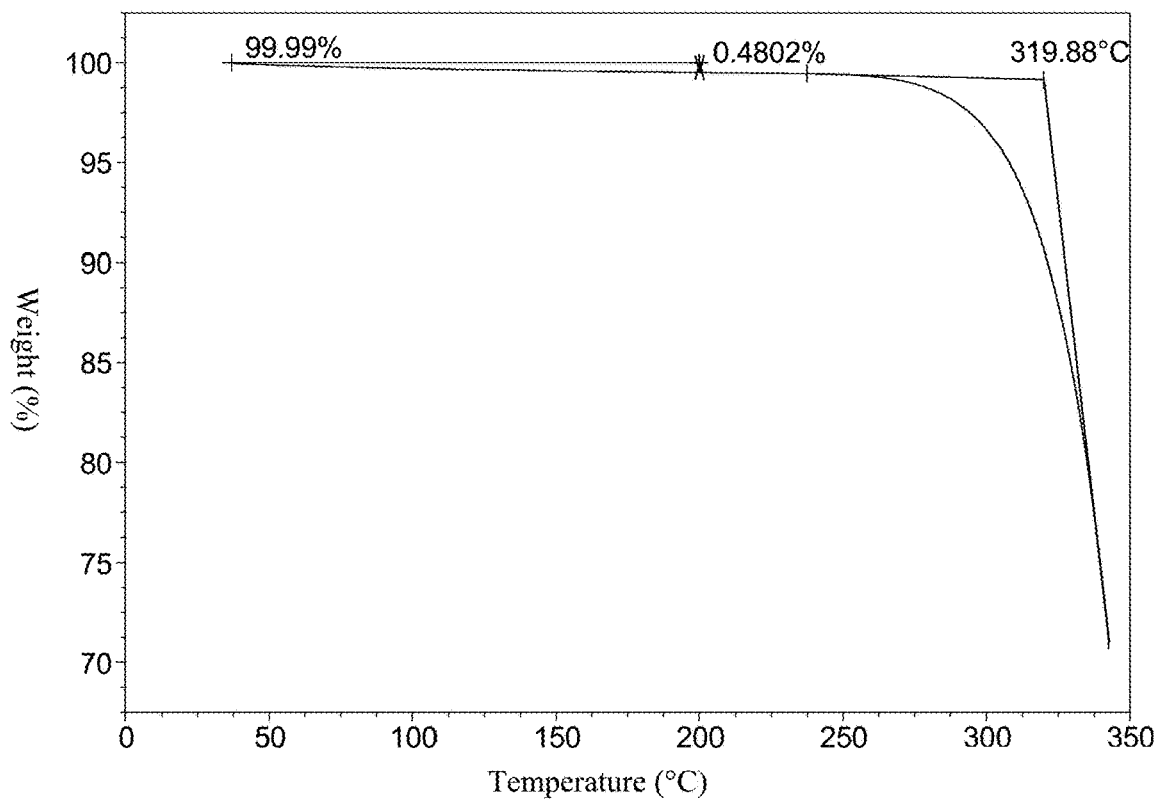
FIG. 29 shows the thermogravimetric analysis pattern of the crystalline form 7.
Figure 30:
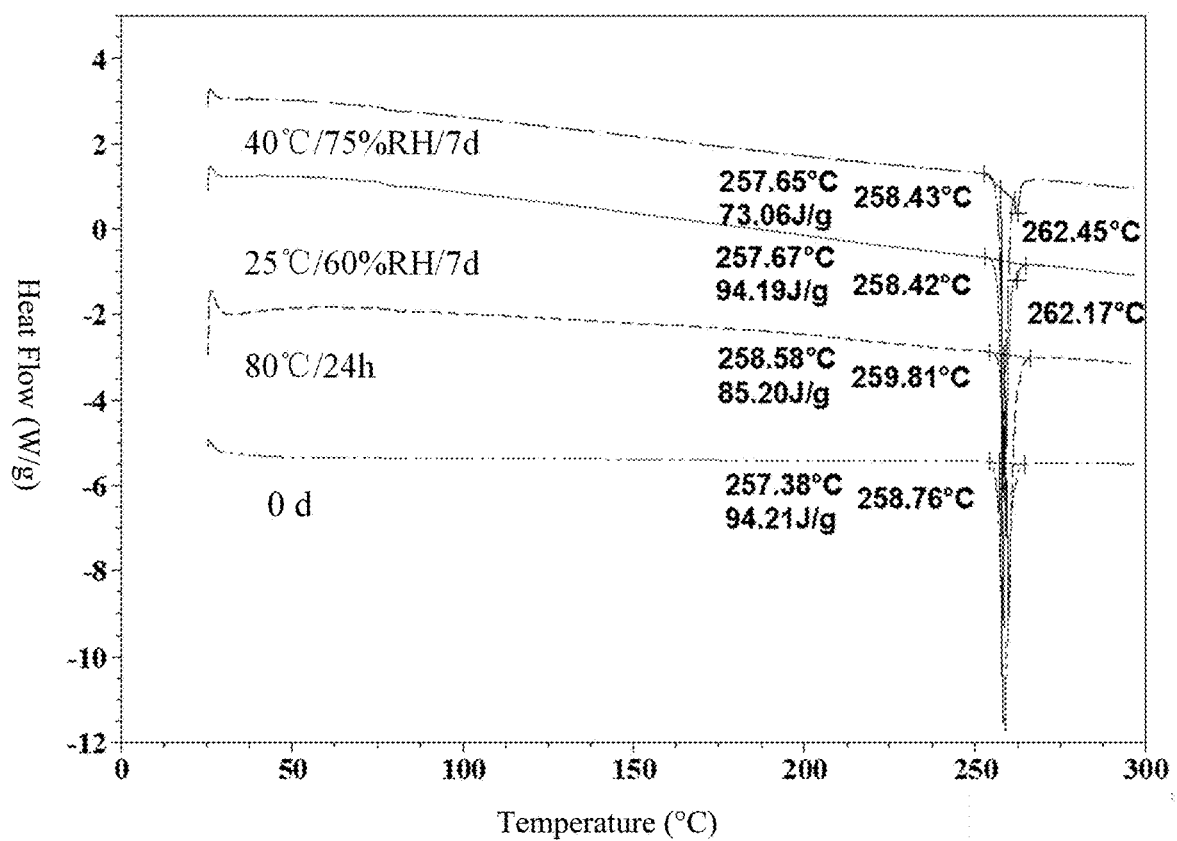
FIG. 30 shows the differential scanning calorimetry pattern of the crystalline form 7.
Figure 31:
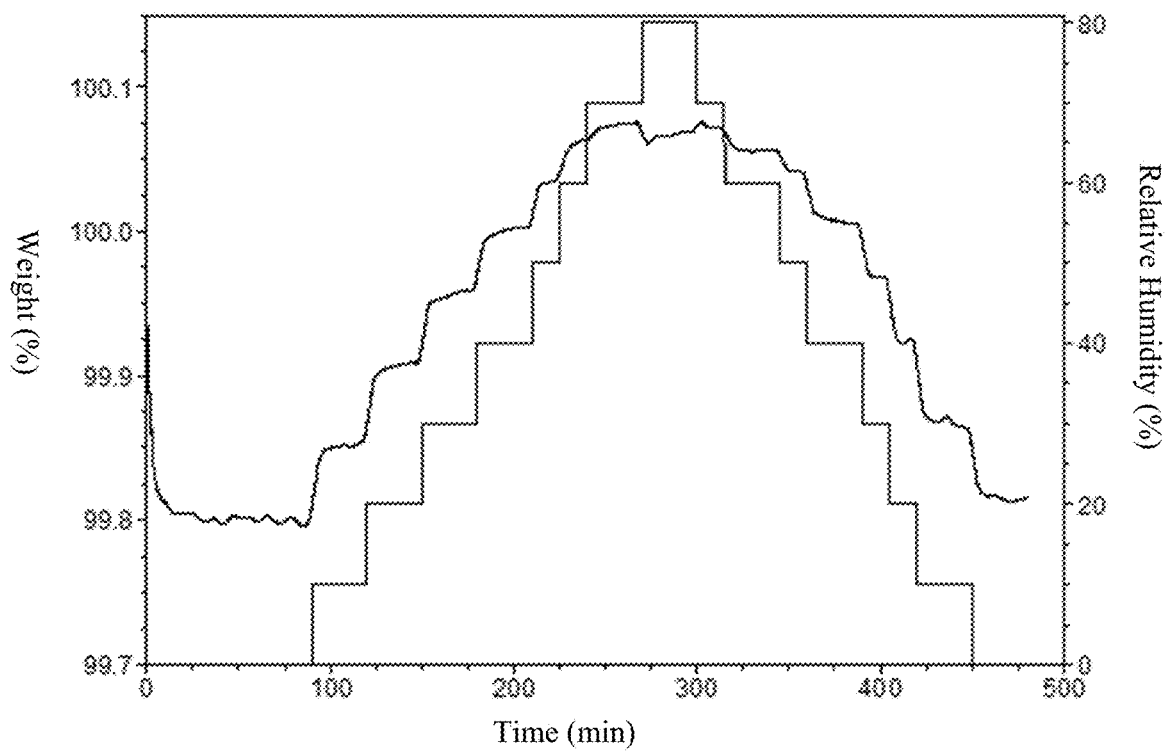
FIG. 31 shows the dynamic vapor sorption pattern of the crystalline form 7.
Figure 32:
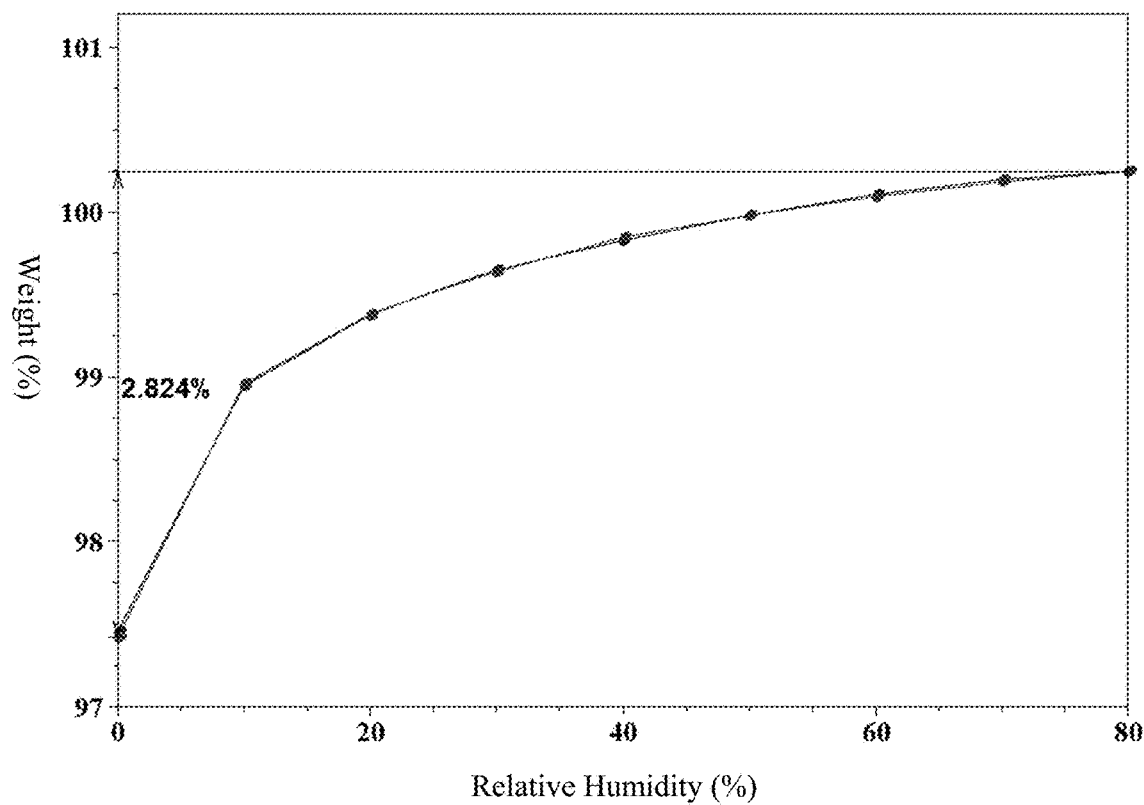
FIG. 32 shows the isothermal adsorption curve of the crystalline form 1.
Figure 33:
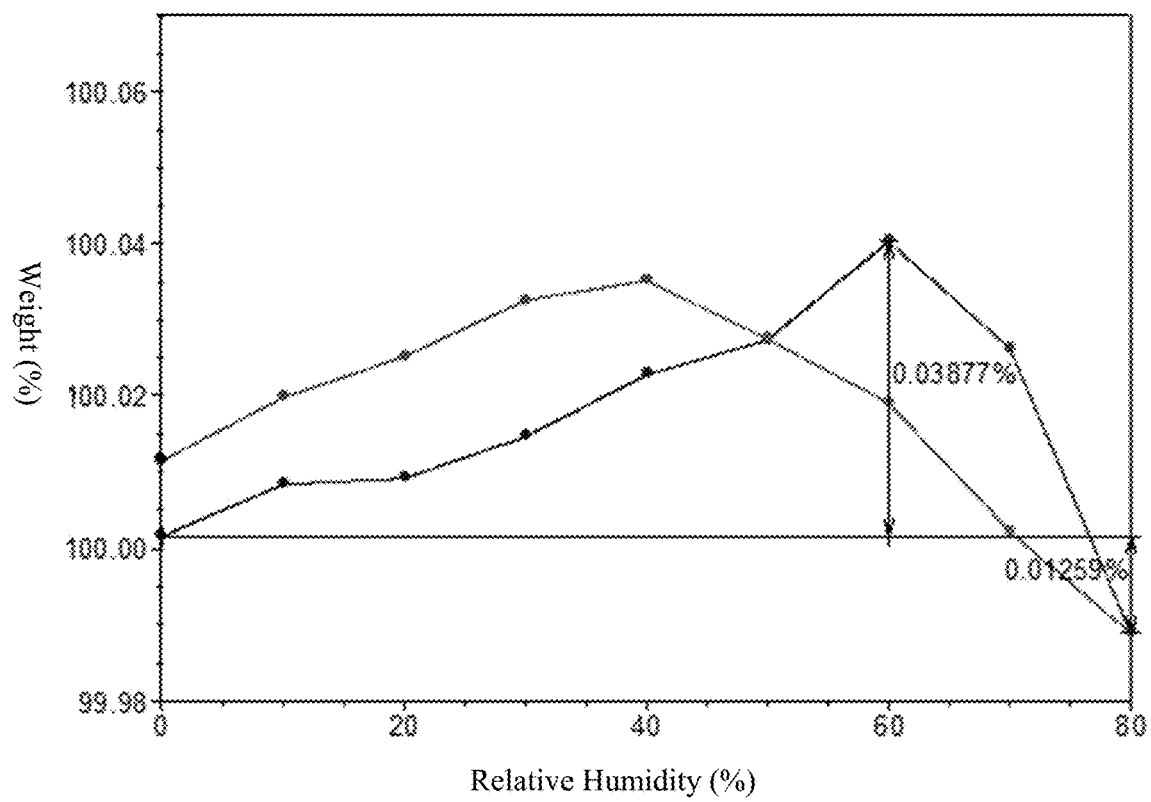
FIG. 33 shows the isothermal adsorption curve of the crystalline form 2.
Figure 34:
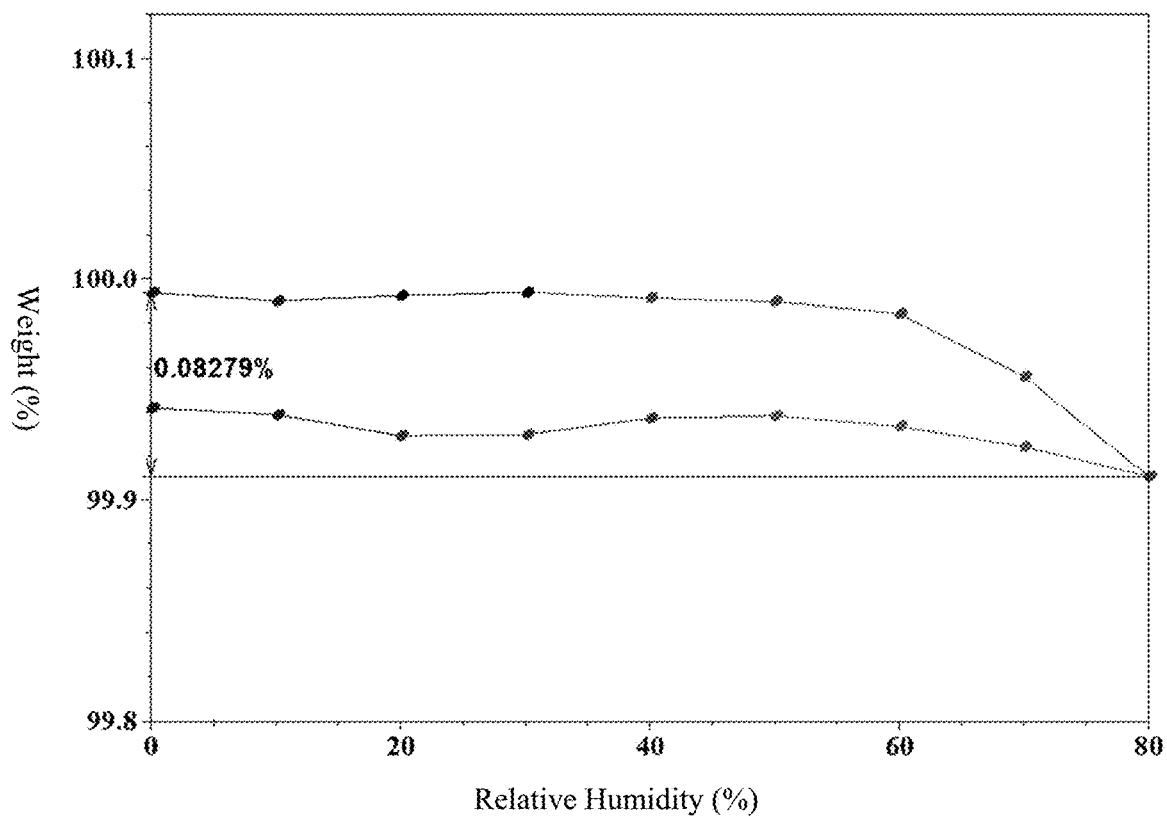
FIG. 34 shows the isothermal adsorption curve of the crystalline form 3.
Figure 35:
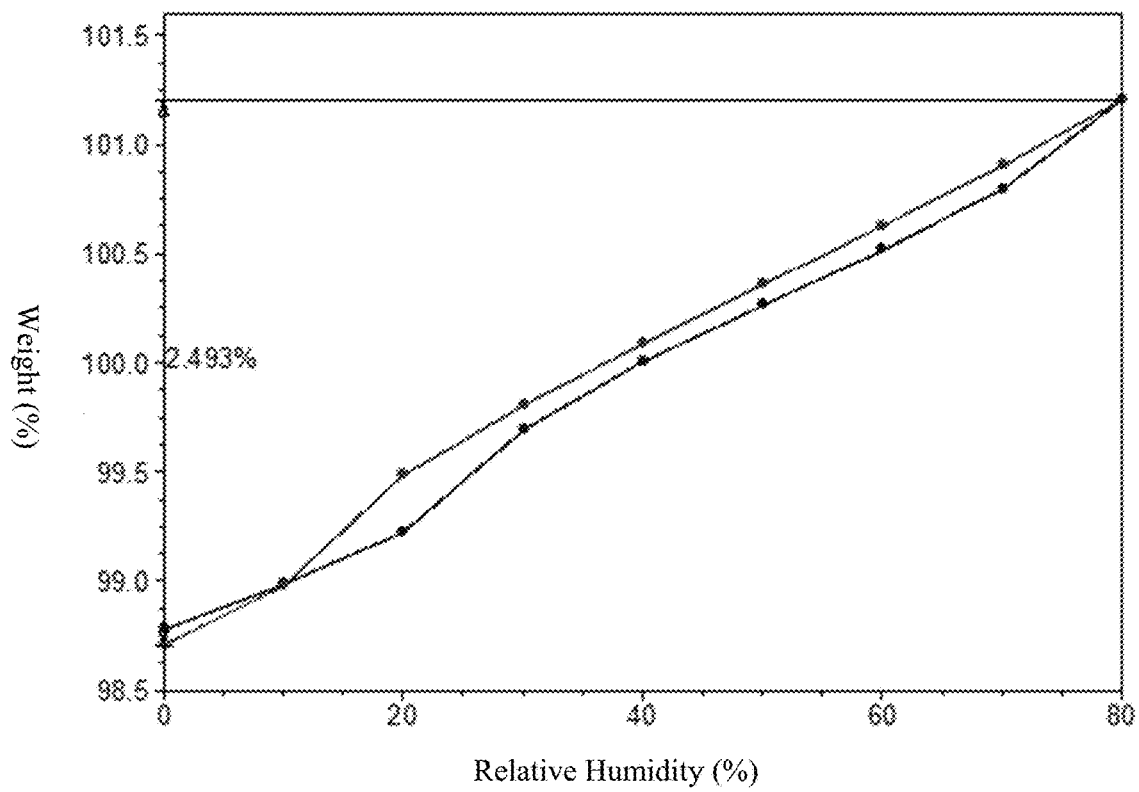
FIG. 35 shows the isothermal adsorption curve of the crystalline form 5.
Figure 36:
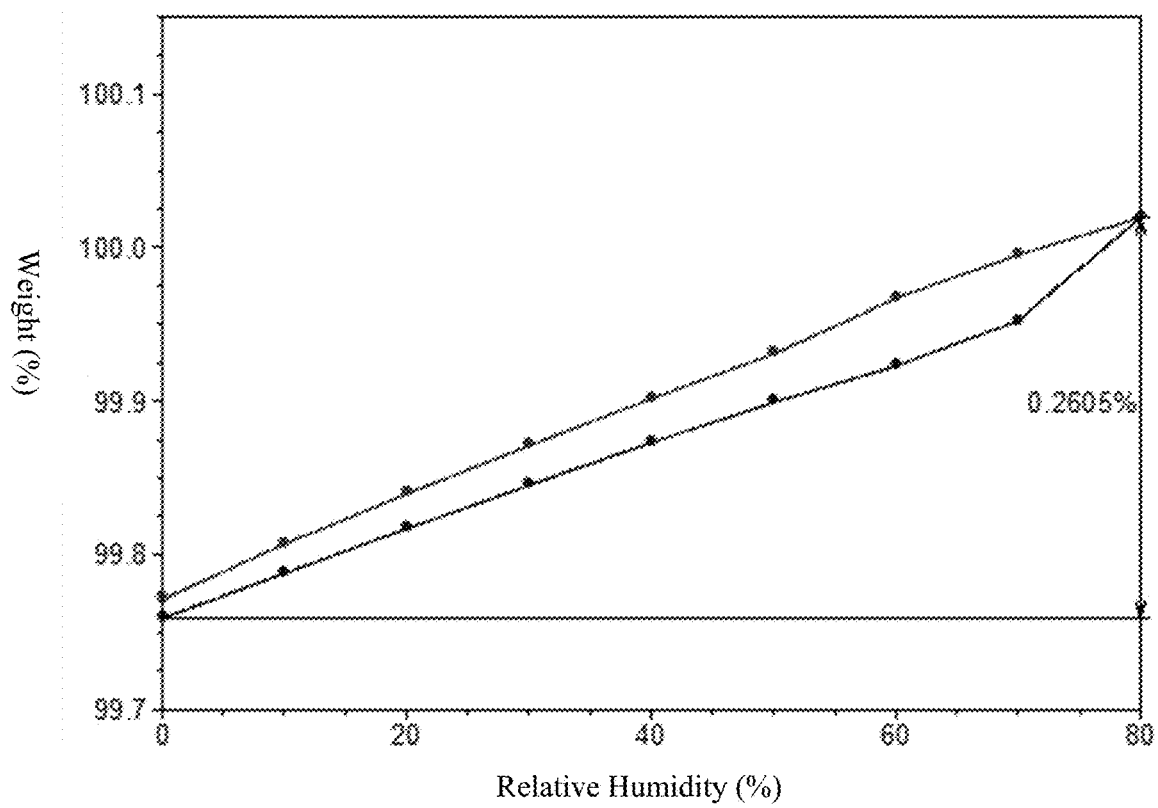
FIG. 36 shows the isothermal adsorption curve of the crystalline form 6.
Figure 37:
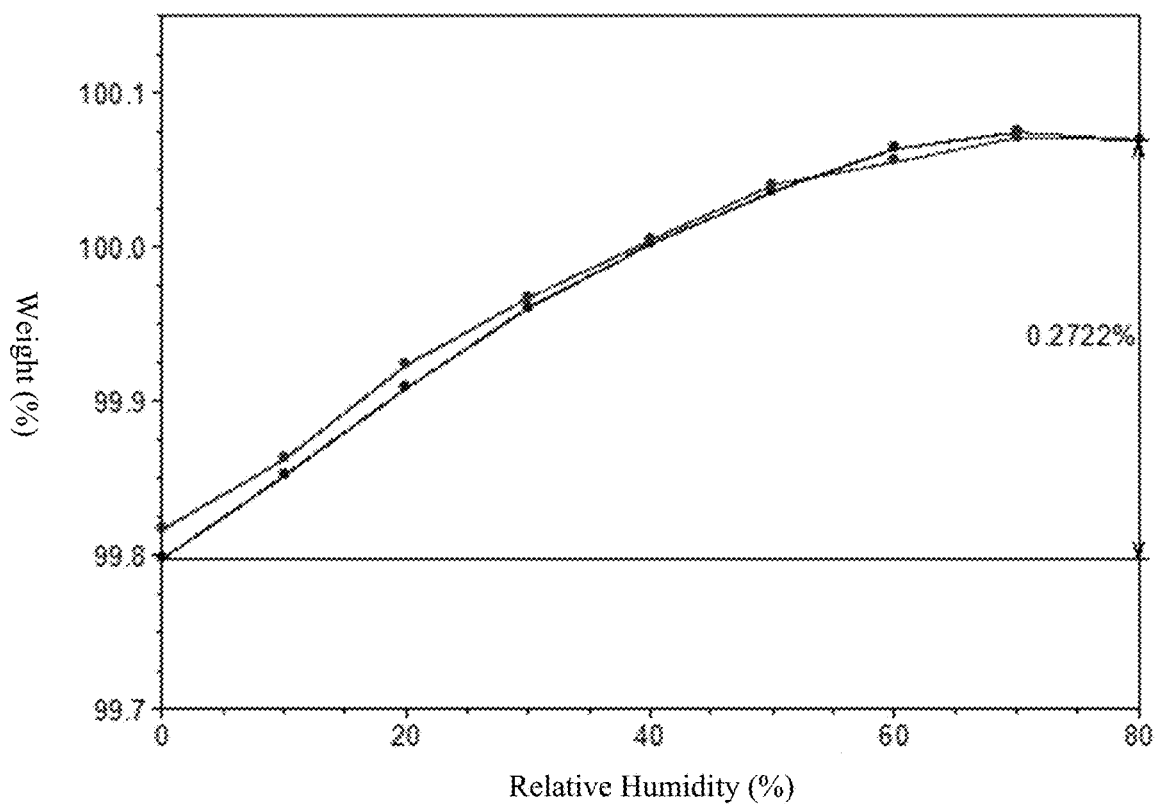
FIG. 37 shows the isothermal adsorption curve of the crystalline form 7.
Figure 38:
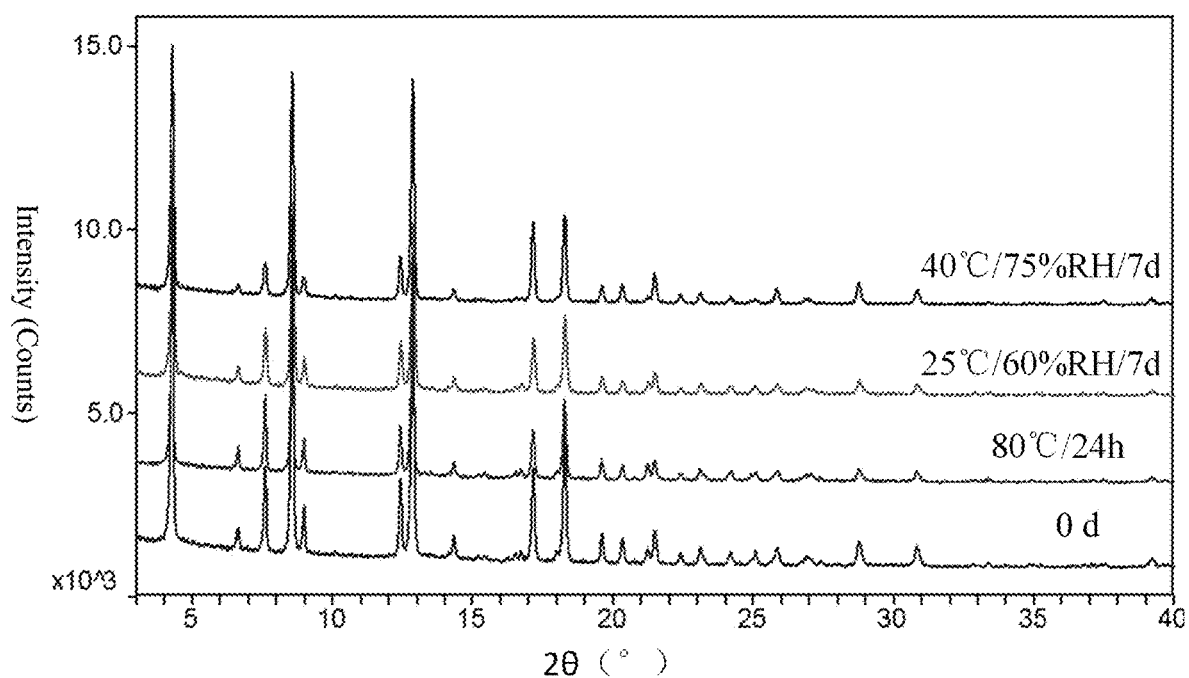
FIG. 38 shows the XRD pattern of crystalline stability of the crystalline form 1.
Figure 39:
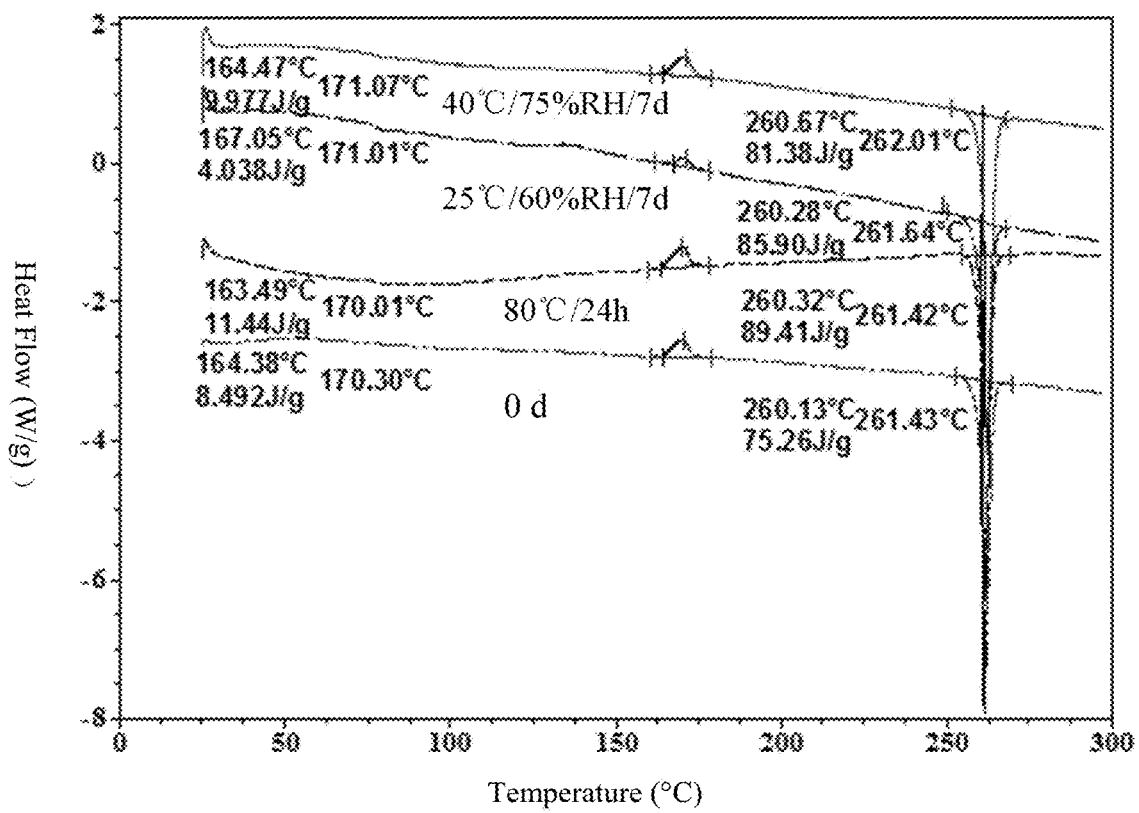
FIG. 39 shows the DSC pattern of crystalline stability of the crystalline form 1.
Figure 40:
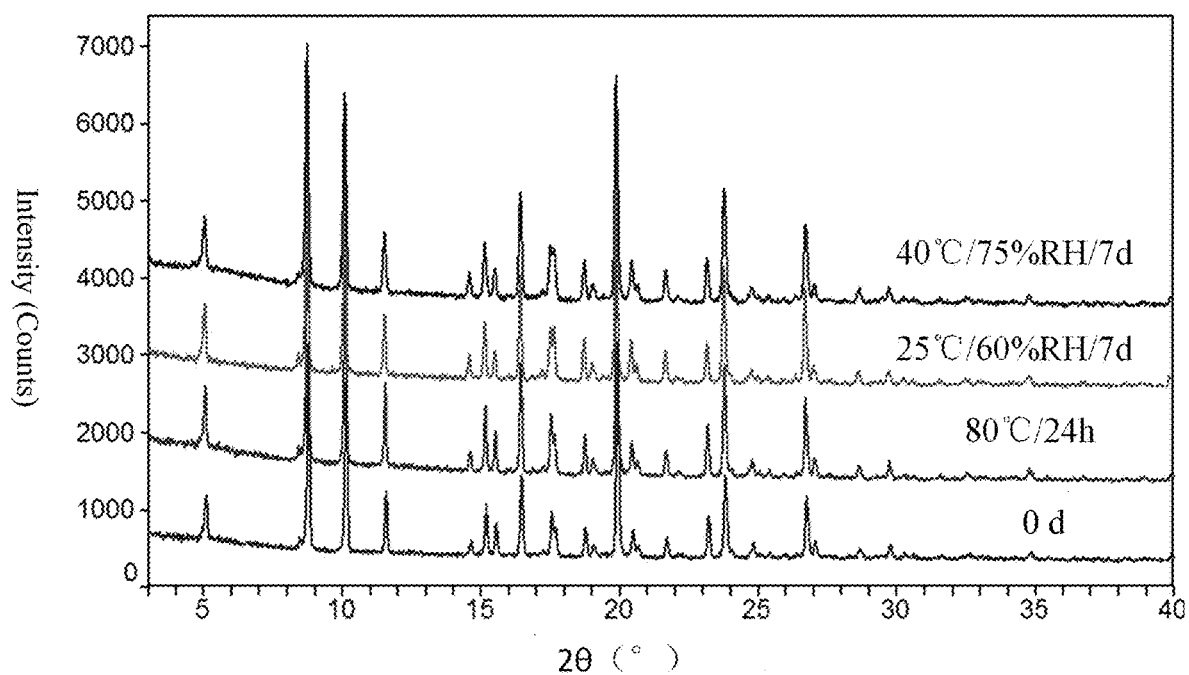
FIG. 40 shows the XRD pattern of crystalline stability of the crystalline form 2.
Figure 41:
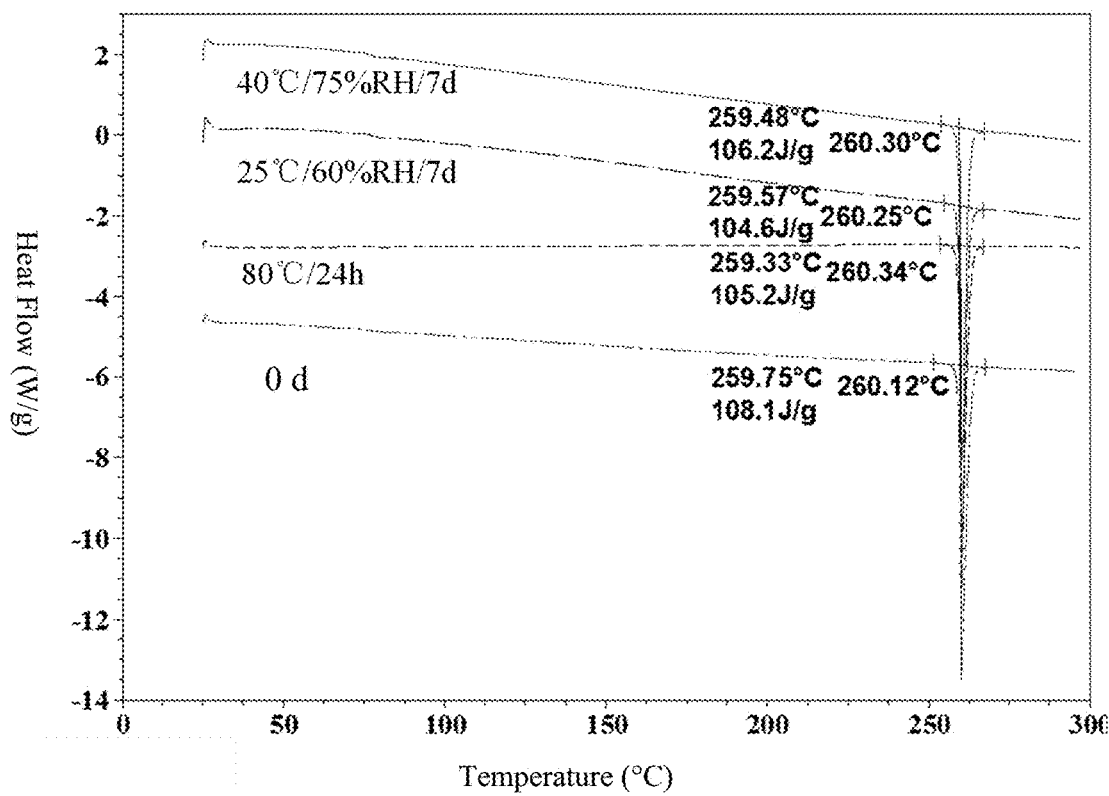
FIG. 41 shows the DSC pattern of crystalline stability of the crystalline form 2.
Figure 42:
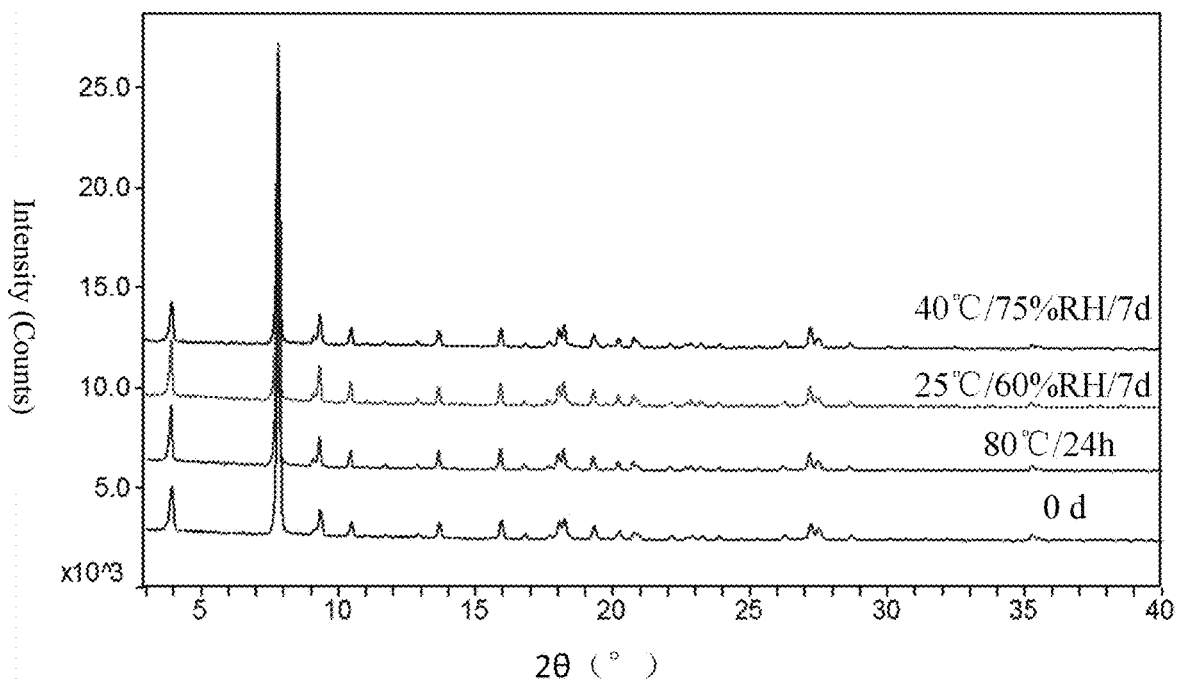
FIG. 42 shows the XRD pattern of crystalline stability of crystalline form 3.
Figure 43:
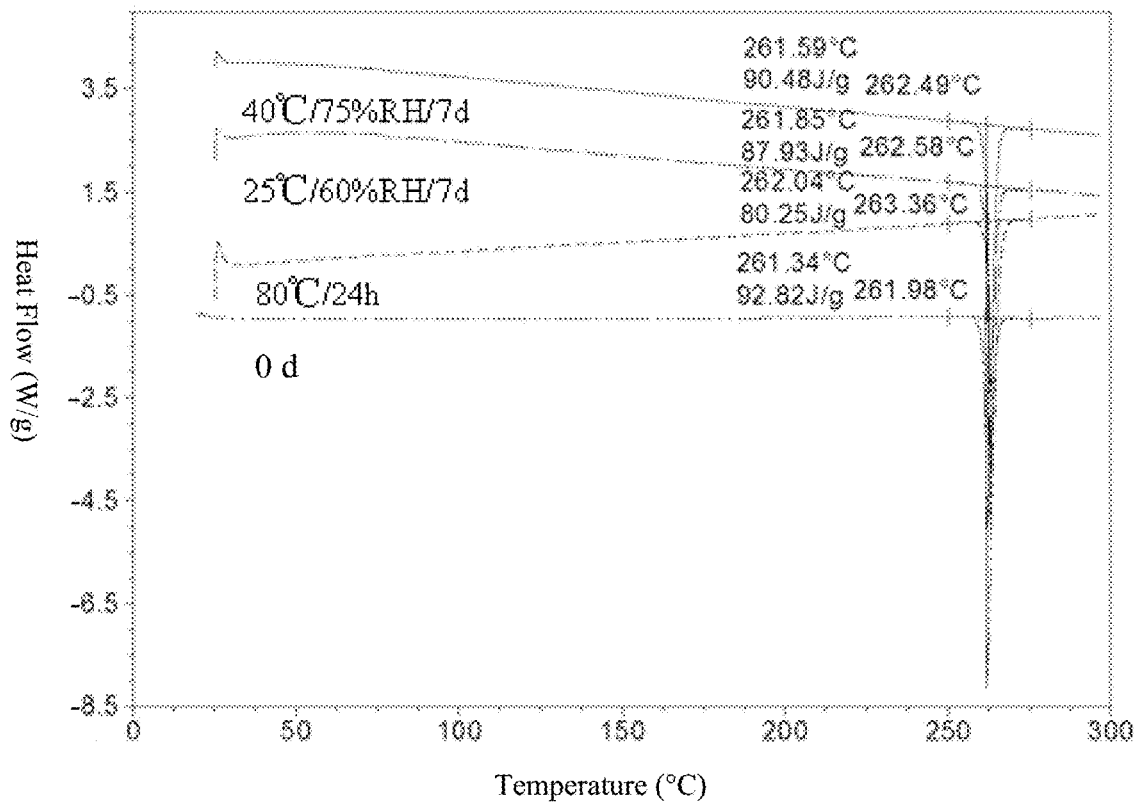
FIG. 43 shows the DSC pattern of crystalline stability of the crystalline form 3.
Figure 44:
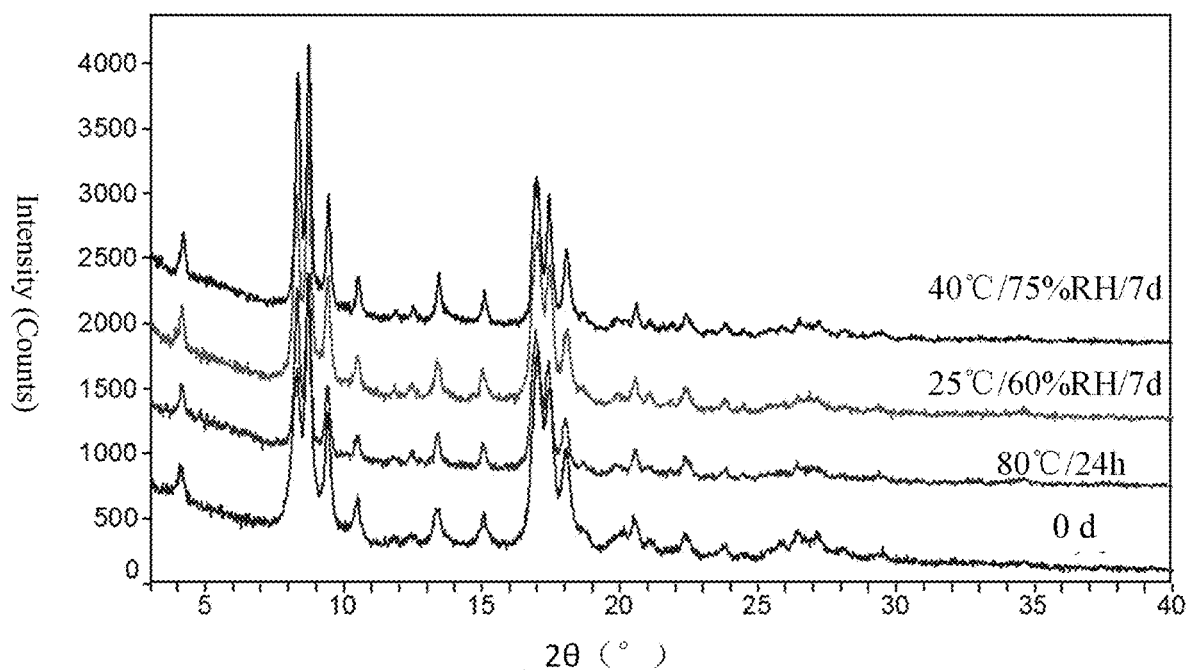
FIG. 44 shows the XRD pattern of crystalline stability of the crystalline form 5.
Figure 45:
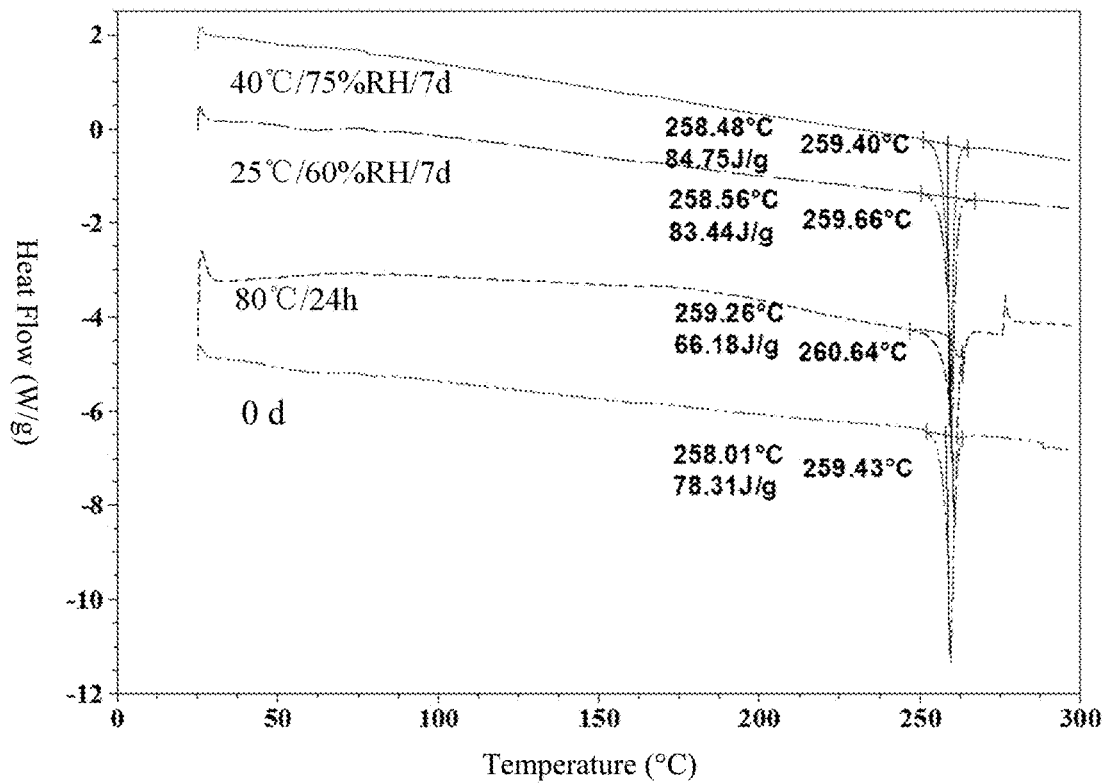
FIG. 45 shows the DSC pattern of crystalline stability of the crystalline form 5.
Figure 46:
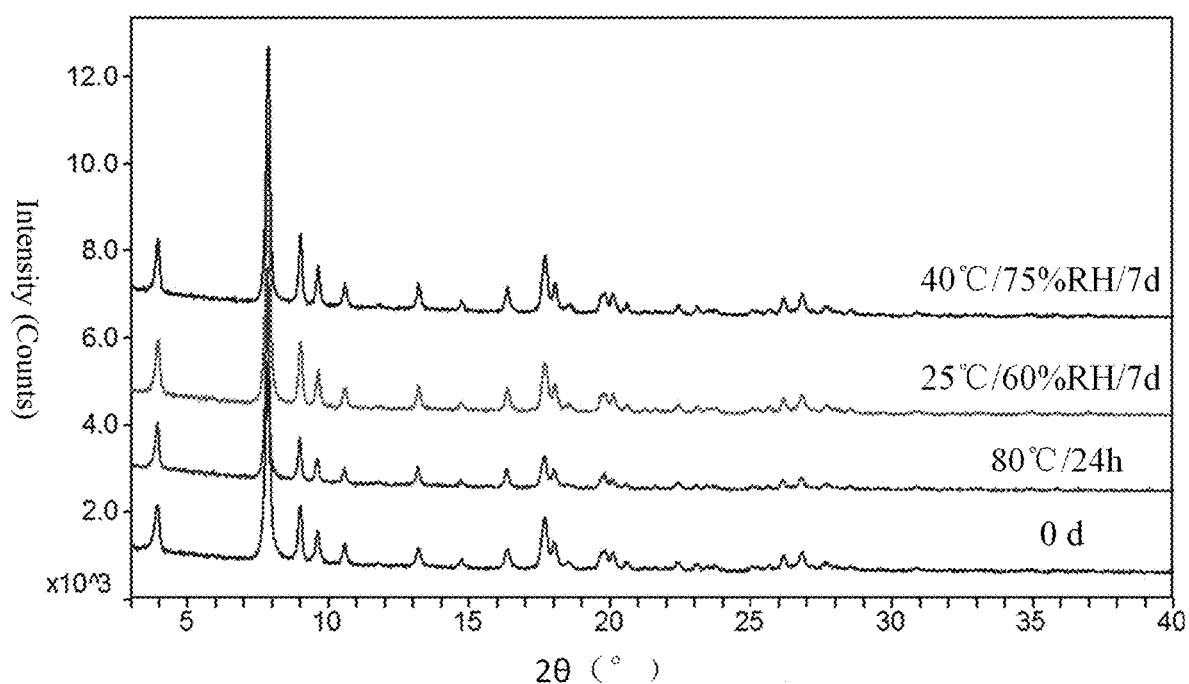
FIG. 46 shows the XRD pattern of crystalline stability of the crystalline form 6.
Figure 47:
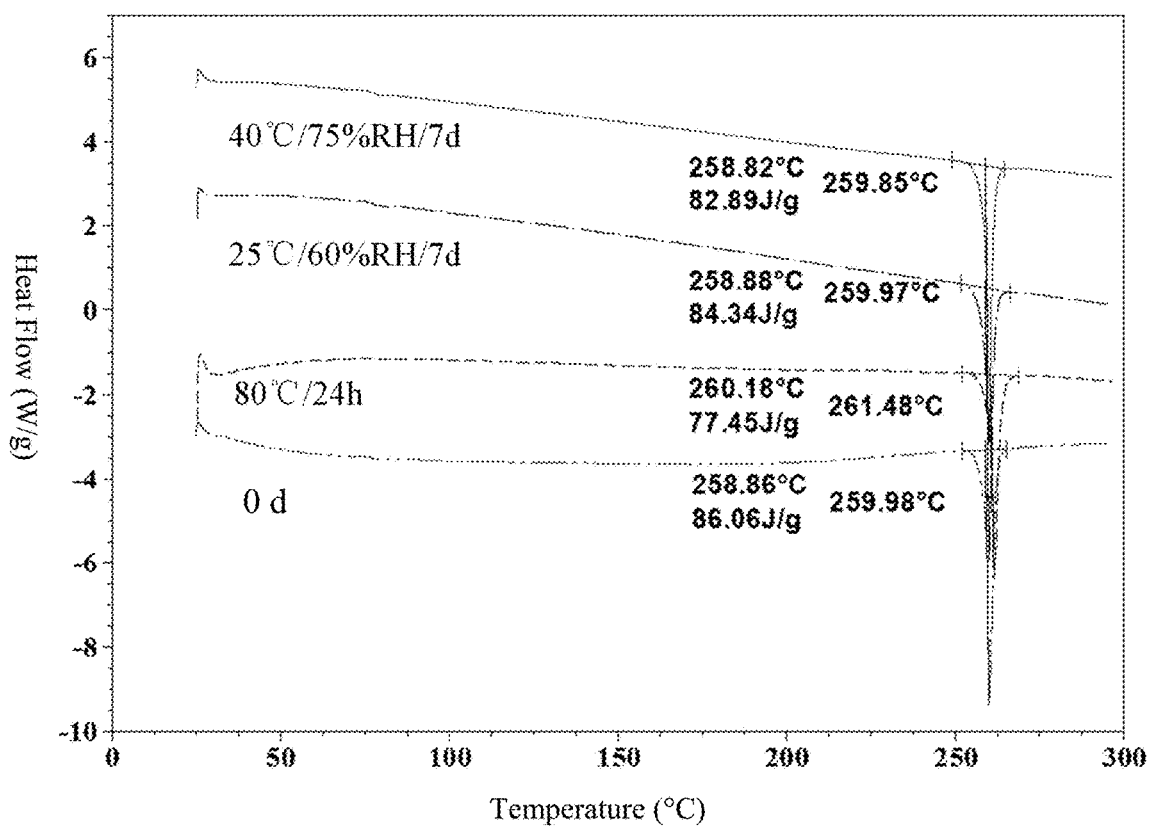
FIG. 47 shows the DSC pattern of crystalline stability of the crystalline form 6.
Figure 48:
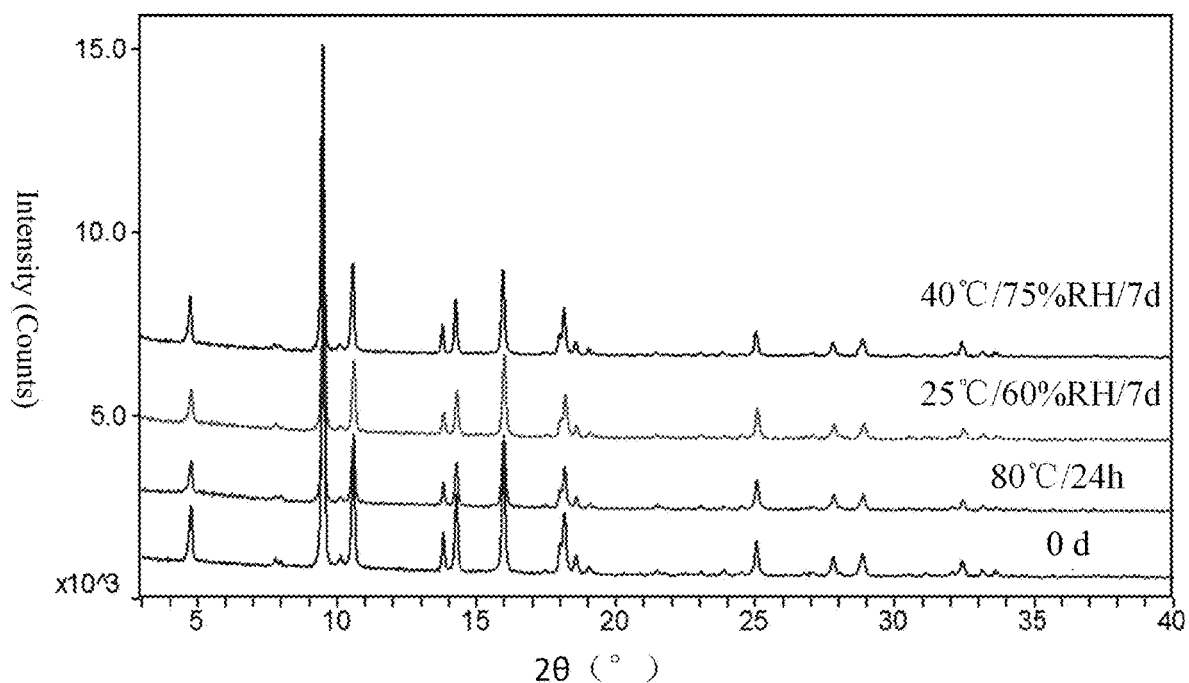
FIG. 48 shows the XRD pattern of crystalline stability of the crystalline form 7.

The products obtained by the above preparation methods were all found to be crystalline form 7 by detection. The X-ray powder diffraction pattern of crystalline form 7 is shown in FIG. 27 and the detailed data of the X-ray powder diffraction pattern thereof is shown in Table 7 above. The polarized light micrograph of crystalline form 7 is shown in FIG. 28, which shows that crystalline form 7 is fine particles and partially agglomerated. Crystalline form 7 has a thermogravimetric analysis pattern as shown in FIG. 29, which shows that crystalline form 6 has a weight loss of 0.5% before 200° C., which is an anhydrous substance with a decomposition temperature of 320° C.; crystalline form 7 has a differential scanning calorimetry diagram as shown in FIG. 30, which shows that the melting point of crystalline form 7 is 259° C., and the crystalline form 7 has a dynamic moisture adsorption diagram as shown in FIG. 31, showing a weight change of 0.27% in the range of 0% RH to 80% RH. The $^1$H-NMR spectrum of crystalline form 7 is consistent to that of FIG. 6.

Example 16

Preparation method 2 of crystalline form 7 of the compound of formula I (wherein the crystalline form of the compound of formula I used below is the crystalline form 1):

The compound of formula I was mixed with a mixture of N,N-dimethylacetamide and toluene (the volume ratio of N,N-dimethylacetamide to toluene was 1:9), and after stirring, the crystal slurry was filtered and dried to obtain the crystalline form 7.

The products obtained by the above preparation methods were all found to be the crystalline form 7 by detection, wherein the detection results of XRD, PLM, TGA, DSC, DVS, 1H-NMR and solubility were the same as in Example 14.

Effect Example 1

The isothermal adsorption curves of the samples of crystalline forms 1, 2, 3, 5, 6 and 7 were shown in FIGS. 32 to 37.

Effect Example 2

The stability of the crystalline forms 1, 2, 3, 5, 6, and 7 was investigated.

Experimental conditions: the samples were sealed and placed at 80° C. for 24 hours, and then placed in an open dish at 25° C./60% RH (relative humidity) and 40° C./75% RH for 7 days. Detection method: HPLC (only for the starting samples and samples placed at 80° C. for 24 hours), XRD, DSC.

Investigation Results:

1) The XRD and DSC tests showed that the crystalline forms and melting points of crystalline forms 1, 2, 3, 5, 6 and 7 are substantially unchanged and relatively stable. The specific test results are shown in FIGS. 38-48, and the DSC spectrum of the crystalline form 7 to show its crystal stability is shown in FIG. 30;

2) HPLC analysis showed that as compared with the initial samples, although decreases in the purity of the main ingredient were found in all the crystalline forms at 80° C. for 24 hours, but they were all kept lower than 2%, as can be seen from the specific data shown in Table 15. Note: the impurity with a retention time of 4.73 min was the transform of the compound, of which the content was related to the degree of protection from light while detection.

TABLE 15

| | HPLC | |
|---|---|---|
| Samples | Purity % | Maximum single impurity % (retention time, min) |
| crystalline form 1 (0 day) | 99.67 | 0.22 (4.73) |
| crystalline form 2 (0 day) | 97.76 | 2.15 (4.73) |
| crystalline form 5 (0 day) | 99.86 | 0.05 (8.82) |
| crystalline form 6 (0 day) | 99.09 | 0.80 (4.73) |
| crystalline form 7 (0 day) | 99.28 | 0.58 (4.73) |
| crystalline form 3 (0 day) | 99.14 | 0.76 (4.73) |
| crystalline form 1 (80° C./24 h) | 98.87 | 1.03 (4.73) |
| crystalline form 2 (80° C./24 h) | 98.95 | 0.96 (4.73) |
| crystalline form 5 (80° C./24 h) | 98.80 | 1.10 (4.73) |
| crystalline form 6 (80° C./24 h) | 99.12 | 0.78 (4.73) |
| crystalline form 7 (80° C./24 h) | 98.70 | 1.19 (4.73) |
| crystalline form 3 (80° C./24 h) | 98.32 | 1.58 (4.73) |

In addition, the long-term stabilities of the crystalline form 1 for 12 months, 24 months, 36 months, and 48 months at 25° C./60% RH were also investigated. The results showed that the crystalline forms are substantially unchanged.

Effect Example 3: Thermodynamic Stability Experiment

The crystalline form 1, crystalline form 2, crystalline form 3 and crystalline form 7 of the compound of formula I were mixed with acetone, ethyl acetate, methanol, water and tetrahydrofuran respectively, and then kept at 60° C. for one day for the investigation of the thermodynamic stability of each crystalline form. Insoluble solid was recovered by filtration and analyzed by XRD. Analysis conditions: Shimadzu XRD-6000, CuK source (1.54056 A) 40 kV, 30 mA; detection angle: 5-50°, speed: 5°/min.

Figure 49:
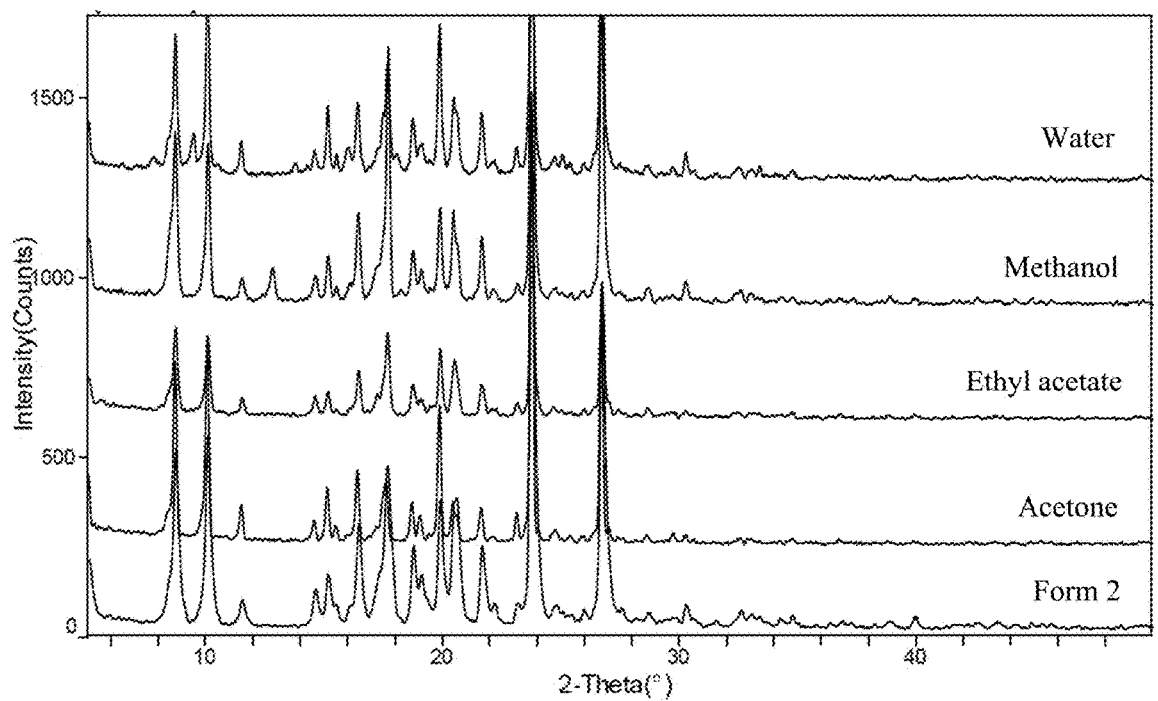
FIG. 49 shows the transformation of the crystalline form 1, crystalline form 2, crystalline form 3 and crystalline form 7 to crystalline form 2 in acetone, ethyl acetate, methanol or water.
Figure 50:
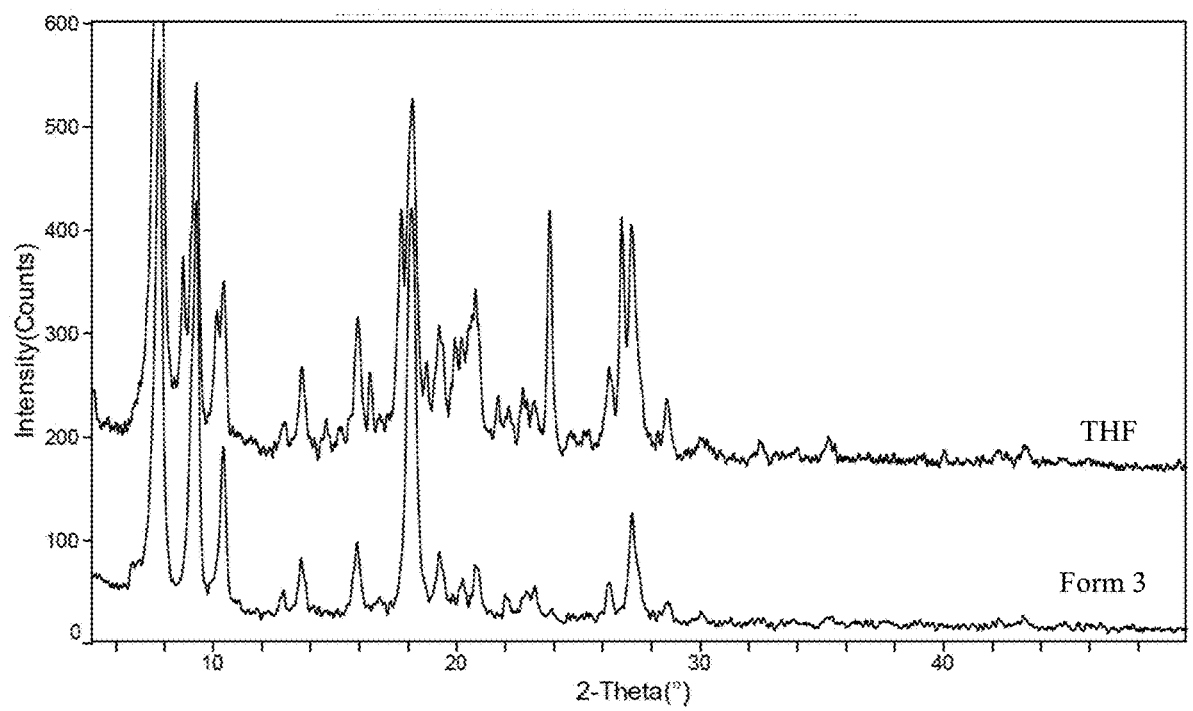
FIG. 50 shows the transformation of the crystalline form 1, crystalline form 2, crystalline form 3 and crystalline form 7 to crystalline form 3 in tetrahydrofuran (THF).

The results showed that the crystalline form 1, crystalline form 2, crystalline form 3 and crystalline form 7 could be converted to crystalline form 2 while being treated with acetone, ethyl acetate, methanol or water. However, according to the peak having a 2θ angle of 13° in FIG. 49, it was found that the conversion to the crystalline form 2 was not completely achieved when methanol was used. FIG. 50 showed that the crystalline form 3 could be provided using THF.

Effect Example 4: Stability of Crystalline Form 1 in Methanol

The stability of the crystalline form 1 in aqueous methanol solution at different temperature and for different time is as follows. The results showed that high temperature and moisture can accelerate the conversion of the crystalline form 1 to the crystalline form 2.

TABLE 16

|  |  | condition |  |  | XRPD detection |  |  |  |
| --- | --- | --- | --- | --- | --- | --- | --- | --- |
|  |  | form 1 | Moisture |  |  |  |  |  |
| Experiment | batch No. | (g) | methanol | (KF) | temperature | 2 hrs | 4 hrs | 8 hrs | 21 hrs |
| 1 | 0556-023-A | 5.0 | 50 mL | 0.1% | reflux | form 1 | form 1 | form 2 | form 2 |
| 2 | 0556-023-B | 5.0 | 50 mL | 5.2% | reflux | form 1 | form 1 + form 2 | form 2 | form 2 |
| 3 | 0556-023-C | 5.0 | 50 mL | 10% | reflux | form 1 | form 2 | form 2 | form 2 |
| 4 | 0556-023-D | 2.0 | 50 mL | 0.1% | 20-30° C. | form 1 | form 1 | form 1 | form 1 |
| 5 | 0556-023-E | 2.0 | 50 mL | 5.2% | 20-30° C. | form 1 | form 1 | form 1 | form 1 |
| 6 | 0556-023-F | 2.0 | 50 mL | 10% | 20-30° C. | form 1 | form 1 | form 1 | form 1 |

Effect Example 5: Quantitative Detection of Crystalline Form 2 in the Crystalline Form 1

The content of crystalline form 2 in the crystalline form 1 of the compound of formula I was analyzed by XRD pattern obtained from Shimadzu XRD-6000, CuK source (1.54056 Å, 40 kV, 30 mA). Detection angle: 9.6-10.4° 2θ; step size: 0.02° 2θ; counting time: 10 s.

Figure 51:
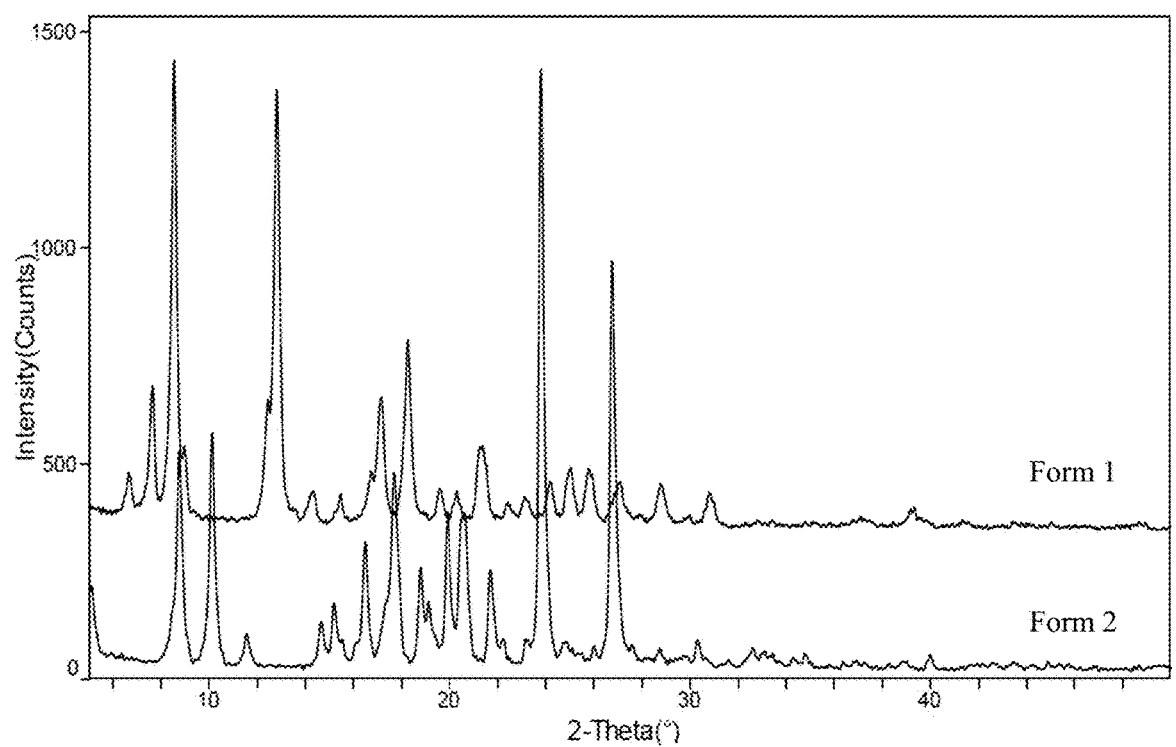
FIG. 51 shows the XRD pattern comparison between the crystalline form 1 and crystalline form 2, wherein the upper spectrum line represents the crystalline form 1 and the lower spectrum line represents the crystalline form 2.

The XRD patterns of the crystalline form 1 and crystalline form 2 are compared in FIG. 51, wherein the peak of the crystalline form 1 at 2θ of 10.1° is very weak, while the crystalline form 2 has a strong characteristic peak. Therefore, the area of the peak may be used to determine the content of crystalline form 2 in crystalline form 1. Crystalline forms 1 and 2 were passed through a 100 mesh screen to ensure that the samples had similar particle sizes. The samples were prepared by mixing an appropriate amount (weight percent) of the crystalline forms 1 and 2 as shown in Table 17. The detection was performed three times in parallel, and the average was taken as the peak intensity at 2θ of 10.1°.

TABLE 17

Peak area of the samples with different content (weight percent) of the crystalline form 2 in the crystalline form 1 at 2θ of 10.1°

|  | crystalline form 2% | | | | | |
| --- | --- | --- | --- | --- | --- | --- |
|  | 0.96% | 2.01% | 3.89% | 5.10% | 10.41% | 15.55% |
| Area | 3528 | 6648 | 16148 | 18025 | 35106 | 57326 |
|  | 3454 | 6517 | 15875 | 18135 | 35510 | 56696 |
|  | 3263 | 6794 | 16145 | 18333 | 35587 | 57621 |

TABLE 17-continued

Peak area of the samples with different content (weight percent) of the crystalline form 2 in the crystalline form 1 at 2θ of 10.1°

|  | crystalline form 2% | | | | | |
| --- | --- | --- | --- | --- | --- | --- |
|  | 0.96% | 2.01% | 3.89% | 5.10% | 10.41% | 15.55% |
| Average area | 3415 | 6653 | 16056 | 18164.3 | 35401 | 57214.3 |
| Relative standard deviation (%) | 3.27 | 1.7 | 0.8 | 0.7 | 0.6 | 0.67 |

Figure 52:
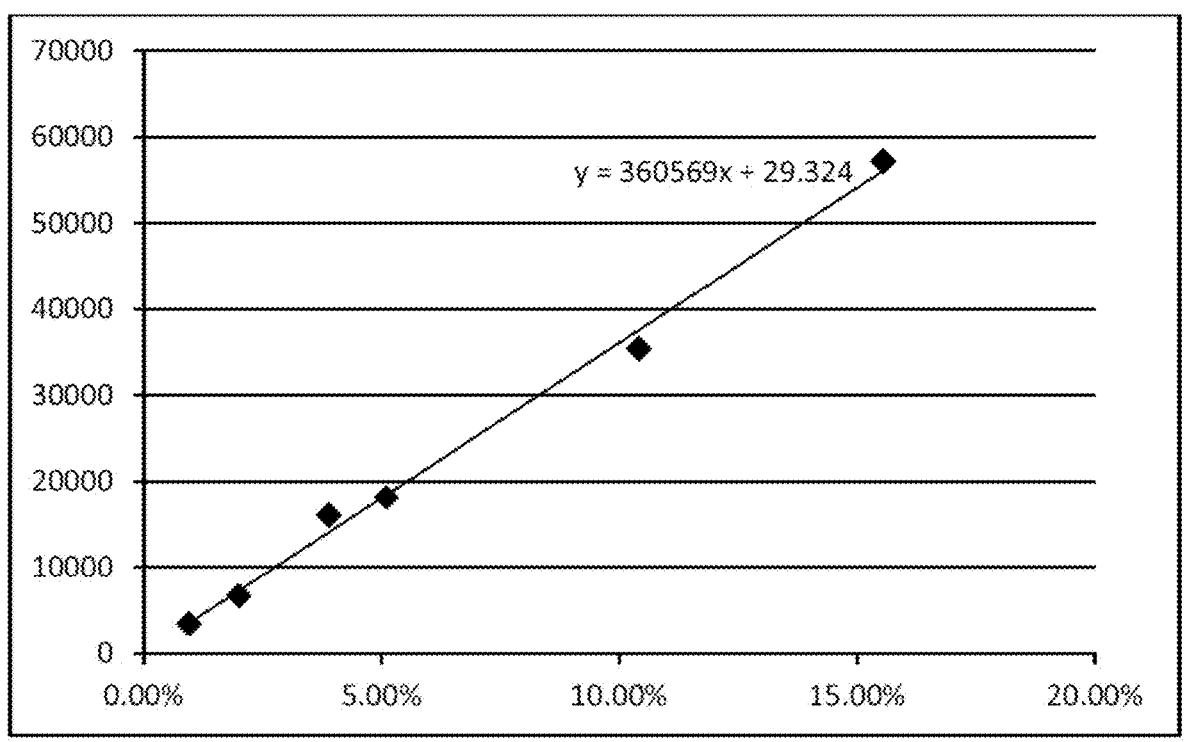
FIG. 52 shows the relationship between the peak area at 2θ of 10.1° and the weight percentage of the crystalline form 2 in the crystalline form 1.

As shown in FIG. 52, the peak area at 2θ of 10.1° is linear with the weight percentage of the crystalline form 2 in the crystalline form 1, which indicates that when the content of the crystalline form 2 in the crystalline form 1 is from 0.96% to 15.55%, the content may be accurately determined by this method.

Samples containing 4.75 wt % and 6.36 wt % crystalline form 2 were prepared separately, and the peak area at 2θ of 10.1° thereof was determined. Also, the peak area was calculated by the linear relationship shown in FIG. 52. As shown below, the calculated value deviation is within 10% of the measured value.

TABLE 18

| Crystalline form 2% | 4.75% | 6.36% |
| --- | --- | --- |
| Measured | 15976 | 21546 |
|  | 15520 | 21238 |
|  | 15707 | 22177 |
| Average area | 15734.3 | 21653.7 |
| Relative standard deviation (%) | 1.19 | 1.8 |
| Calculated value | 17156 | 22961 |
| Calculated value/measured value % | 109.0 | 106.0 |

Effect Example 6: Solubility Determination

The solubility detection method was as follows: an appropriate amount of the sample was added into water to form a suspension, stirred at 25° C. in a water bath, and the solution was taken after 0.5 hour and 4 hours respectively for HPLC concentration detection.

HPLC detection was performed using the crystalline form 1 as a standard, with its concentration of 204.2 µg*mL$^{-1}$ and its content set as 100%, and the detection was performed 7 times. The average peak area was 159.691 mAU*min (retention time was 7.4 min).

Analysis of results: The results of solubility detection of the crystalline forms were shown in Table 19 below. The results show that the solubility of crystalline form 1 is much higher than that of the most stable crystalline form 2.

form 1 are higher than that of the crystalline form 2. Moreover, the crystalline forms 1 and 2 have the highest solubility in methanol.

TABLE 19

| crystalline form | 0.5 hours | | 4 hours | |
|---|---|---|---|---|
| | peak area mAU*min | concentration ug*mL$^{-1}$ | peak area mAU*min | concentration ug*mL$^{-1}$ |
| crystalline form 1 | 0.829 | 1.12 | 0.984 | 1.32 |
| crystalline form 2 | 0.143 | 0.19 | 0.191 | 0.26 |
| crystalline form 5 | 1.232 | 1.66 | 0.313 | 0.42 |
| crystalline form 6 | 0.217 | 0.29 | 0.275 | 0.37 |
| crystalline form 7 | 0.389 | 0.52 | 0.450 | 0.61 |
| crystalline form 3 | 0.432 | 0.58 | 0.574 | 0.77 |

Effect Example 7: Moisture-Induced Crystallization Experiment of the Crystalline Form 1

About 10 mg of the crystalline form 1 was taken and placed in the corresponding environment, and the solid was detection by XRD at different time. The characterization results showed that only the known crystalline form 1 was detected in this experiment. The specific experiment details and results are shown in Table 20 below, which shows that the crystalline form 1 is stable under these conditions.

TABLE 20

| Temperature-relative humidity | Result analysis | | |
|---|---|---|---|
| | 1 day | 5 days | 10 days |
| Room temperature-58% RH | crystalline form 1 | crystalline form 1 | crystalline form 1 |
| Room temperature - 75% RH | crystalline form 1 | crystalline form 1 | crystalline form 1 |
| Room temperature - 97% RH | crystalline form 1 | crystalline form 1 | crystalline form 1 |

Effect Example 8: Pharmacological Properties of the Crystalline Forms 1 and 2

The moisture content, solubility and dissolution rate of the crystalline forms 1 and 2 were detected using the methods described above. The results are shown in Table 21, which indicate that the solubility, dissolution, and moisture content (total pharmaceutical properties) of the crystalline

TABLE 21

| Parameters | | Crystalline form 2 | Crystalline form 1 |
|---|---|---|---|
| Moisture absorption (%) | RH 50% | 0.064 | 2.015 |
| | RH 80% | 0.112 | 2.578 |
| Solubility (µg/ml) | aqueous solution with pH of 1.0-7.5 | 0.0048-0.04 | 0.12-0.53 |
| | acetonitrile | 270 | 680 |
| | methanol | 3500 | 8170 |
| | ethanol | 1940 | 2460 |
| | PEG 400 | 2670 | 3660 |
| | glycerin | 120 | 570 |
| | 1% sodium lauryl sulfate | 580 | 3480 |
| | 2% sodium lauryl sulfate | 950 | 3790 |
| | 1% Tween 80 | 20 | 60 |
| Internal dissolution rate mg/(min · cm$^2$) | | 0.0062 | 0.022 |
| Solubility of artificial gastric juice (4 hours) | | 2.25 | 10.15 |
| Solubility of artificial gastric juice (4 hours) | | 0.00 | 0.43 |

Effect Example 9: Pharmacokinetic Experiment

Twelve Sprague Dawley rats with weight of 230-250 g were randomly divided into 2 groups, wherein each group consisted of 3 males and 3 females. Crystalline forms 1 and 2 were separately prepared as suspensions in 0.5% carboxymethylcellulose (CMC). The rats were fasted for 12 hours with free access to water and then orally administered at a dose of 10 mg/kg. Blood samples (0.2-0.3 ml) before and after 15, 30, 60, 120, 240, 360, 480, 720, 1440 minutes of the oral administration were collected in heparin anticoagulation tubes, which were then centrifuged to obtain plasma. The plasma was stored at −20° C., followed by analysis using API 4000 MS in conjunction with a HPLC unit. The pharmacokinetic parameters Cmax and AUC were calculated according to the determined plasma concentrations and summarized in Table 22. The results show that the crystalline form 1 has a Cmax of about 4 times higher than the crystalline form 2, and about 3 times more exposure (AUC) than the crystalline form 2.

TABLE 22

| | female 1 | female 2 | female 3 | male 1 | male 2 | male 3 | average value |
|---|---|---|---|---|---|---|---|
| | crystalline form 1 | | | | | | |
| Cmax (ng/ml) | 593.9 | 2649.0 | 2033.3 | 716.6 | 1071.3 | 977.7 | 1340.3 |
| AUC(0-t) (ng · hr/ml) | 3536.6 | 28571.4 | 16634.2 | 3180.0 | 6766.0 | 4241.5 | 10488.3 |
| | crystalline form 2 | | | | | | |
| Cmax (ng/ml) | 317.0 | 451.4 | 614.6 | 204.4 | 114.7 | 180.4 | 313.8 |
| AUC(0-t) (ng · hr/ml) | 4344.4 | 3899.2 | 7850.6 | 1557.1 | 925.0 | 1349.3 | 3320.9 |

Effect Example 10: Tissue Accumulation Experiment of the Crystalline Form 1

Human colon cancer H-29 cells were implanted into the armpits of BALB/cA nude mice. Seven days after the implantation of H-29 cells, 8 female mice were administered with the crystalline form 1 (twice a day) at 40 mg/kg or sunitinib at 40 mg/kg (once a day). The drug administration was continuous for 21 days. Plasma, tissue and tumor samples were collected for analysis 4 hours after the administration on the 22nd day morning. The results were summarized in Table 23. The data shows that the tissue accumulation of crystalline form 1 in all tested tissues is significantly lower than that of sunitinib, while the content of crystalline form 1 in plasma was comparable to that of sunitinib.

TABLE 23

| | Samples | | | | | | | |
|---|---|---|---|---|---|---|---|---|
| | Plasma | Tumor | Liver | Kidney | Heart | Lung | Muscle | Brain |
| crystalline form 1 | 191.6 | 153.4 | 1,715.3 | 418.3 | 124.8 | 144.9 | 77.6 | 9.3 |
| Sunitinib | 261.3 | 27,137.2 | 14,816.6 | 14,852.0 | 3,881.2 | 15,713.5 | 1,483.2 | 333.9 |

Effect Example 11: Grinding Stability Experiment of the Crystalline Form 1

Crystalline form 1 was ground and sieved. The US standard 200-300 mesh sieved samples were collected and XRD analyzed. Analysis conditions: Shimadzu XRD-6000, CuK source (1.54056 Å) 40 kV, 30 mA; detection angle: 5-50°, speed: 5°/min.

Figure 53:
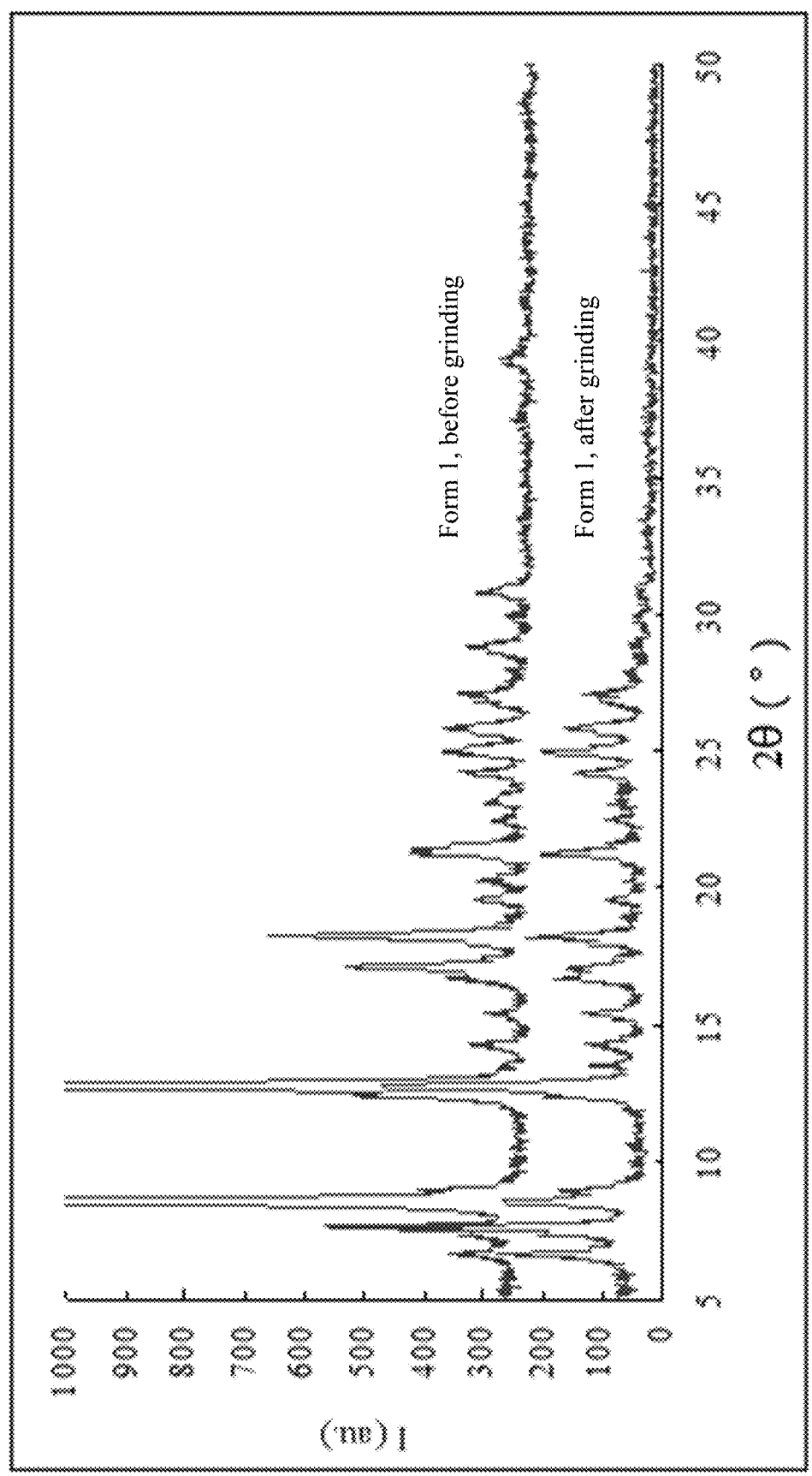
FIG. 53 shows the XRD pattern comparison of crystalline form 1 before and after grinding, wherein the upper spectrum line is the XRD pattern before grinding, and the lower spectrum line is the XRD pattern after grinding.

FIG. 53 shows that the XRD pattern substantially did not change before and after grinding, indicating that the crystalline form 1 remained stable during the grinding process.

Effect Example 12: Preparation of Capsules

1) Weighing, Grinding and Sieving

About ¼ volume of crystalline form 1 was added to the mortar. The crystalline form 1 was ground with a muller to reduce the particle size, and sieved through 250 μm (#60) to the sieve collection tray. The ground and sieved crystalline form 1 was transferred into a container. The above steps were repeated until all the crystalline form 1 was ground and sieved. The total amount of crystalline form 1 that may be used to prepare the capsule was calculated.

The Pearlitol 200 SD was sieved through a 500 μm (#35) sieve and collected into a suitable container.

2) Mixing 830.3±0.1 g of the sieved Pearlitol in Container #1, 1417.5±0.1 g of sodium bicarbonate powder, 405.0±0.1 g of sodium lauryl sulfate and 405.0±0.1 g of croscarmellose sodium were transferred to a preparation container containing the crystalline form 1 (162.0±0.1 g). The container of the crystalline form 1 which was ground and sieved was dry-cleaned three times by the sieved Pearlitol (830.3±0.1 g) in Container #2, and the dry-cleaned product was transferred to the preparation container of the crystalline form 1. Subsequently, the remaining sieved Pearlitol was transferred to the preparation container of crystalline form 1.

3) Blending

Turbula Type T10B Shaker Mixer and the preparation container of crystalline form 1 were installed according to the manufacturer's instructions. After blending in Turbula Type T10B Shaker Mixer for 10 minutes, the preparation of crystalline form 1 was sieved using a 500 μm sieve and the sieved materials were blended for 2 minutes. Three samples (900-2000 mg each) were taken from the top, middle and bottom of the crystalline form 1 preparation container to carry out the content uniformity test during the preparation.

4) Capsule Filling

The average weight of the No. 0 Swedish Orange Opaque Coni-Snap Capsule was determined. Weight limits of acceptable capsule fill were calculated. Two Profill manual capsule fillers were prepared for filling. The amount of preparation required for 100 capsules per plate was 51.0 g (2% excess per plate). The preparation required for each filling tray (51.0±0.1 g) was weighed and filled into the capsule evenly. The Profill was tapped to fill all of the preparations into the capsules completely and evenly, and then adjusted to seal the capsules. The capsule cap was placed back over the capsule body filled with the preparation and pressed to secure the closure. The step can be repeated, if necessary, to ensure that all capsule caps are placed over the capsule body. The capsules were visually inspected and all capsules with physical defects (i.e., the capsule cap was broken) were removed. A weight check was performed on each capsule. The above steps were repeated until all available preparations were filled into the capsule. All acceptable capsules were dusted.

Effect Example 13: Preparation of Tablets

1) The formulation is shown in the following table:

TABLE 24

| Component | 100 mg Intensity tablet (kg/batch) | 50 mg Intensity tablet (kg/batch) |
|---|---|---|
| Batch (number of tablets) | 65,000 pills | 40,000 pills |
| Crystalline form 1 | 6.5754[1] | 2.0232[1] |
| Mannitol, USP | 13.0000 | 9.0112 |
| Microcrystalline cellulose | 13.0000 | 9.0112 |
| Sodium bicarbonate powder, USP | 11.7000 | 7.2000 |
| Anhydrous citric, BP, Ph Eur, USP | 4.4590 | 2.7440 |
| Croscarmellose Sodium, NF | 4.7450 | 2.9200 |
| Sodium lauryl sulfate, NF | 3.2500 | 2.0000 |
| Crospovidone, USP | 2.8600 | 1.7600 |
| Fumed silica | 1.8525 | 1.1400 |
| Sodium stearyl fumarate, NF | 0.3088 | 0.1900 |
| Purified water [2] | QS (sufficient quantity) | QS |
| Total amount (core) | 61.7507 | 37.9996 |
| Opadry II Orange | 1.8525 | 1.1400 |
| Total amount (coated tablets) | 63.6032 | 39.1396 |

[1] The unit content of the active pharmaceutical ingredient (API) crystalline form 1 has been adjusted for impurities and moisture content.
[2] Removed during processing The manufacturing process of the tablet is as follows:

1) API Grinding/Sieving

Crystalline form 1 was ground and sieved twice using a Comil sieve equipped with a 459 μm screen.

2) Excipient Grinding/Sieving

All excipients were mixed in a V-type blender for 5 minutes, sieved through a Comil screen, and removed agglomeration once through a 1 mm screen.

3) Blending

The ground and sieved material was transferred to a V-type blender and blended under dry conditions for 45 minutes.

4) Tableting

The blended final product was pressed into an oval (100 mg) or round (50 mg) core on a high-speed rotary tablet press. The weight, thickness and hardness of the tablet during the process were detected, followed by dusting, polishing and metal detection.

5) Coating

The core was coated with a film in a rotary disc coater and dried. Unqualified tablets were separated and removed. The tablets that meet the requirements were visually inspected for defects and could be tested for quality.

The loose pieces were placed in a container lined with a double polyethylene bag and a desiccant and stored until the packaging process.

6) Final Packaging

The tablets were packaged in high density polyethylene (HDPE) bottles that were sealed using an inductively sealed polypropylene lid.

The product is stored at a controlled room temperature until the labeling process.

7) The products were labelled in the labeling and logistics center.

The exemplary embodiments of the present invention have been described above. However, the technical solution of the present invention is not limited thereto. Those skilled in the art will appreciate that any modifications, equivalent substitutions, improvements, etc., which are within the spirit and scope of the invention, are intended to be included within the scope of the invention.

We claim:

1. Crystalline form 1 of the compound of formula I:

formula I

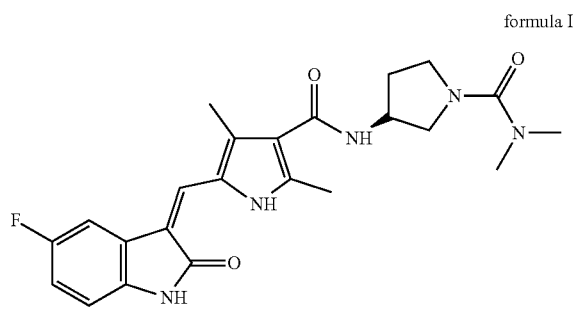

having an X-ray powder diffraction pattern comprising peaks at diffraction angle 2θ of 4.3±0.2°, 8.6±0.2°, and 12.9±0.2°.

2. The crystalline form 1 of claim 1, wherein the X-ray powder diffraction pattern of the crystalline form 1 further comprises a peak at diffraction angle 2θ of 7.6±0.2°.

3. The crystalline form 1 of claim 2, wherein the X-ray powder diffraction pattern of the crystalline form 1 further comprises peaks at diffraction angle 2θ of 6.7±0.2° and 18.3±0.2°.

4. The crystalline form 1 of claim 1, having a differential scanning calorimetry (DSC) pattern showing an exothermic peak at 150-170° C., a melting point at about 260° C., and/or a thermogravimetric analysis (TGA) pattern showing a weight loss of about 2.6% before 170° C. and a decomposition temperature of about 320° C.

5. A pharmaceutical composition, comprising a therapeutically effective amount of the crystalline form 1 according to claim 1, and at least one pharmaceutically acceptable adjuvant.

6. Crystalline form 1 of the compound of formula I:

formula I having an X-ray powder diffraction pattern comprising at least 3 peaks at diffraction angle 2θ selected from 4.3±0.2°, 6.7±0.2°, 7.6±0.2°, 8.6±0.2°, 9.0±0.2°, 12.4±0.2°, 12.9±0.2°, 14.3±0.2°, 17.2±0.2°, and 18.3±0.2°.

7. The crystalline form 1 of claim 6, having at least one of a differential scanning calorimetry (DSC) pattern showing an exothermic peak at 150-170° C., a melting point at about 260° C., and a thermogravimetric analysis (TGA) pattern showing a weight loss of about 2.6% before 170° C. and a decomposition temperature of about 320° C.

8. A pharmaceutical composition, comprising a therapeutically effective amount of the crystalline form 1 according to claim 6, and at least one pharmaceutically acceptable adjuvant.

9. Crystalline form 3 of the compound of formula I:

formula I having an X-ray powder diffraction pattern comprising peaks at diffraction angle 2θ of 7.8±0.2° and 9.3±0.2°.

10. The crystalline form 3 of claim 9, having at least one of a differential scanning calorimetry (DSC) pattern substantially as shown in FIG. 15, a melting point at about 261° C., and a thermogravimetric analysis (TGA) pattern showing a weight loss of about 0.2% before 200° C.

11. The crystalline form 3 of claim 9, wherein the X-ray power diffraction pattern of the crystalline form 3 further comprises peaks at diffraction angle 2θ 13.7±0.2 and 16.0±0.2°.

12. The crystalline form 3 of claim 11, wherein the X-ray power diffraction pattern of the crystalline form 3 further comprises peaks at diffraction angle 2θ of 3.9±0.2° and 18.2±0.2°.

13. A composition comprising a mixture of the crystalline form 3 of claim 9 and at least one other crystalline form selected from crystalline form 2, crystalline form 6, and crystalline form 7, wherein,
the crystalline form 1 has an X-ray powder diffraction pattern comprising peaks at diffraction angle 2θ of 4.3±0.2°, 8.6±0.2°, and 12.9±0.2°, the crystalline form 2 has an X-ray powder diffraction pattern comprising peaks at diffraction angle 2θ of 8.8±0.2°, 10.1±0.2°, 23.8±0.2°, and 26.7±0.2°, the crystalline form 5 has an X-ray powder diffraction pattern comprising peaks at diffraction angle 2θ of 8.7±0.2°, 17.0±0.2°, and 17.4±0.2°, the crystalline form 6 has an X-ray powder diffraction pattern comprising peaks at diffraction angle 2θ of 7.9±0.2°, 9.1±0.2°, and 17.7±0.2°, and the crystalline form 7 has an X-ray powder diffraction pattern comprising peaks at diffraction angle 2θ of 9.5±0.2°, 10.6±0.2°, and 16.0±0.2°.

14. The composition of claim 13, wherein the composition comprises a mixture of the crystalline form 3 and crystalline form 7.

15. A pharmaceutical composition, comprising a therapeutically effective amount of the crystalline form 3 according to claim 9, and at least one pharmaceutically acceptable adjuvant.

16. Crystalline form 5 of the compound of formula I:

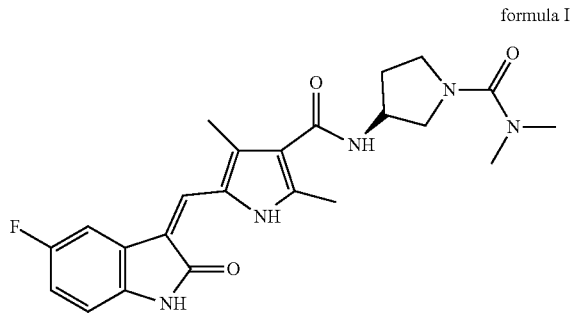

formula I having an X-ray powder diffraction pattern comprising peaks at diffraction angle 2θ of 8.7±0.2°, 9.4±0.2°, and 18.1±0.2°.

17. The crystalline form 5 of claim 16, wherein the X-ray power diffraction pattern of the crystalline form 5 further comprises peaks at diffraction angle 2θ of 4.1 ±0.2° and 17.0±0.2°.

18. The crystalline form 5 of claim 16, having at least one of a differential scanning calorimetry (DSC) pattern substantially as shown in FIG. 20, a melting point at about 258° C., and a thermogravimetric analysis (TGA) pattern showing a weight loss of about 1.2% before 200° C.

19. A pharmaceutical composition, comprising a therapeutically effective amount of the crystalline form 5 according to claim 16, and at least one pharmaceutically acceptable adjuvant.

20. Crystalline form 6 of the compound of formula I:

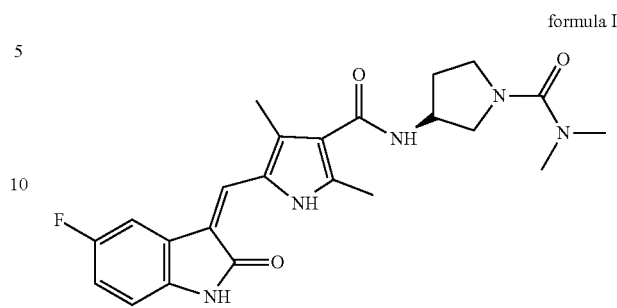

formula I having an X-ray powder diffraction pattern comprising peaks at diffraction angle 2θ of 7.9±0.2°, 9.1±0.2°, and 17.7±0.2°.

21. The crystalline form 6 of claim 20, having at least one of a differential scanning calorimetry (DSC) pattern substantially as shown in FIG. 25, and a thermogravimetric analysis (TGA) pattern showing a weight loss of about 0.7% before 200° C.

22. The crystalline form 6 of claim 20, wherein the X-ray power diffraction pattern of the crystalline form 6 further comprises peaks at diffraction angle 2θ of 3.9±0.2°, 9.6±0.2°, and 13.2±0.2°.

23. A pharmaceutical composition, comprising a therapeutically effective amount of the crystalline form 6 according to claim 20, and at least one pharmaceutically acceptable adjuvant.

24. Crystalline form 7 of the compound of formula I:

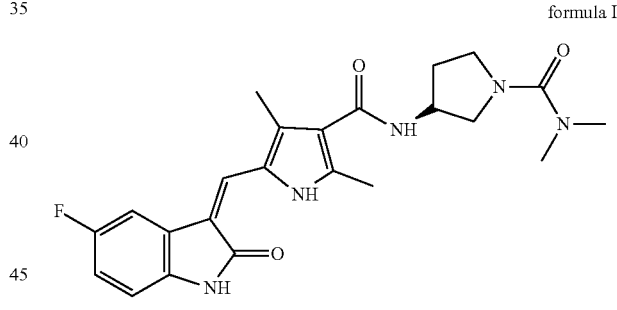

formula I having an X-ray powder diffraction pattern comprising peaks at diffraction angle 2θ of 9.5±0.2°, 10.6±0.2°, and 16.0±0.2°.

25. The crystalline form 7 of claim 24, having at least one of a differential scanning calorimetry (DSC) pattern substantially as shown in FIG. 30, and a thermogravimetric analysis (TGA) pattern showing a weight loss of about 0.5% before 200° C.

26. The crystalline form 7 of claim 24, wherein the X-ray power diffraction pattern of the crystalline form 7 further comprises peaks at diffraction angle 2θ of 4.8±0.2° and 25.1±0.2.

27. The crystalline form 7 of claim 24, wherein the X-ray power diffraction pattern of the crystalline form 7 further comprises peaks at diffraction angle 2θ of 13.8±0.2°, 14.3±0.2° and 18.2±0.2.

28. A pharmaceutical composition, comprising a therapeutically effective amount of the crystalline form 7 according to claim 24, and at least one pharmaceutically acceptable adjuvant.

29. A composition comprising a mixture of the crystalline form 7 of claim 24 and at least one other crystalline form selected from crystalline form 2 and crystalline form 6.

30. A pharmaceutical composition, comprising a therapeutically effective amount of the composition according to claim 29, and at least one pharmaceutically acceptable adjuvant.

31. A composition comprising a mixture of the crystalline form 7 of claim 24 and at least one other crystalline form selected from crystalline form 1, crystalline form 2, crystalline form 5 and crystalline form 6, wherein, the crystalline form 1 has an X-ray powder diffraction pattern comprising peaks at diffraction angle 2θ of 4.3±0.2°, 8.6±0.2°, and 12.9±0.2°, the crystalline form 2 has an X-ray powder diffraction pattern comprising peaks at diffraction angle 2θ of 8.8±0.2°, 10.1±0.2°, 23.8±0.2°, and 26.7±0.2°, the crystalline form 5 has an X-ray powder diffraction pattern comprising peaks at diffraction angle 2θ of 8.7±0.2°, 17.0±0.2°, and 17.4±0.2°, and the crystalline form 6 has an X-ray powder diffraction pattern comprising peaks at diffraction angle 2θ of 7.9±0.2°, 9.1±0.2°, and 17.7±0.2°.

32. A composition comprising a mixture of crystalline form 1 and at least one other crystalline form selected from crystalline form 2, crystalline form 3, crystalline form 5, crystalline form 6, and crystalline form 7 of the compound of formula I,

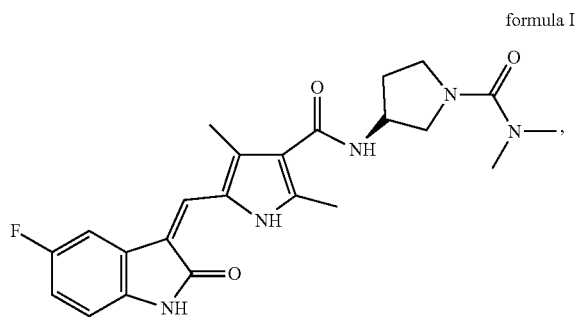

formula I wherein, the crystalline form 1 has an X-ray powder diffraction pattern comprising peaks at diffraction angle 2θ of 4.3±0.2°, 8.6±0.2°, and 12.9±0.2°, the crystalline form 2 has an X-ray powder diffraction pattern comprising peaks at diffraction angle 2θ of 8.8±0.2°, 10.1±0.2°, 23.8±0.2°, and 26.7±0.2°, the crystalline form 3 has an X-ray powder diffraction pattern comprising a peak at diffraction angle 2θ of 3.9±0.2° and 7.8±0.2°, the crystalline form 5 has an X-ray powder diffraction pattern comprising peaks at diffraction angle 2θ of 8.7±0.2°, 17.0±0.2°, and 17.4±0.2°, the crystalline form 6 has an X-ray powder diffraction pattern comprising peaks at diffraction angle 2θ of 7.9±0.2°, 9.1±0.2°, and 17.7±0.2°, and the crystalline form 7 has an X-ray powder diffraction pattern comprising peaks at diffraction angle 2θ of 9.5±0.2°, 10.6±0.2°, and 16.0±0.2°.

33. The composition of claim 32, wherein the composition has an X-ray powder diffraction pattern comprising peaks at diffraction angle 2θ of 4.3±0.2°, 8.6±0.2°, and 12.9±0.2°, and further comprises at least one additional peak at diffraction angle 2θ selected from 4.1±0.2°, 7.8±0.2°, 7.9±0.2°, 8.7±0.2°, 8.8±0.2°, 9.1±0.2°, 9.5±0.2°, 10.1±0.2°, 10.6±0.2°, 16.0±0.2°, 17.0±0.2°, 17.4±0.2°, 17.7±0.2°, 23.8±0.2°, and 26.7±0.2°.

34. A pharmaceutical composition, comprising a therapeutically effective amount of the composition according to claim 32, and at least one pharmaceutically acceptable adjuvant.

35. A composition comprising a mixture of crystalline form 1 and at least one other crystalline form selected from crystalline form 2, crystalline form 3, crystalline form 5, crystalline form 6, and crystalline form 7 of the compound of formula I,

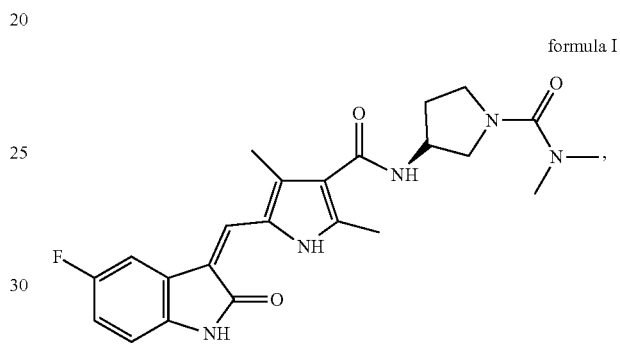

formula I wherein, the crystalline form 1 has an X-ray powder diffraction pattern comprising at least 3 peaks at diffraction angle 2θ selected from 4.3±0.2°, 6.7±0.2°, 7.6±0.2°, 8.6±0.2°, 9.0±0.2°, 12.4±0.2°, 12.9±0.2°, 14.3±0.2°, 17.2±0.2°, and 18.3±0.2°, the crystalline form 2 has an X-ray powder diffraction pattern comprising peaks at diffraction angle 2θ of 8.8±0.2°, 10.1±0.2°, 23.8±0.2°, and 26.7±0.2°, the crystalline form 3 has an X-ray powder diffraction pattern comprising a peak at diffraction angle 2θ of 3.9±0.2° and 7.8±0.2°, the crystalline form 5 has an X-ray powder diffraction pattern comprising peaks at diffraction angle 2θ of 8.7±0.2°, 17.0±0.2°, and 17.4±0.2°, the crystalline form 6 has an X-ray powder diffraction pattern comprising peaks at diffraction angle 2θ of 7.9±0.2°, 9.1±0.2°, and 17.7±0.2°, and the crystalline form 7 has an X-ray powder diffraction pattern comprising peaks at diffraction angle 2θ of 9.5±0.2°, 10.6±0.2°, and 16.0±0.2°.

36. The composition of claim 35, wherein the X-ray powder diffraction pattern of the composition further comprises at least one additional peak at diffraction angle 2θ selected from 4.1±0.2°, 4.3±0.2°, 7.8±0.2°, 7.9±0.2°, 8.7±0.2°, 8.8±0.2°, 9.1±0.2°, 9.5±0.2°, 10.1±0.2°, 10.6±0.2°, 16.0±0.2°, 17.0±0.2°, 17.4±0.2°, 17.7±0.2°, 23.8±0.2°, and 26.7±0.2°.

37. A composition comprising a mixture of crystalline form 3 and crystalline form 7 of the compound of formula I:

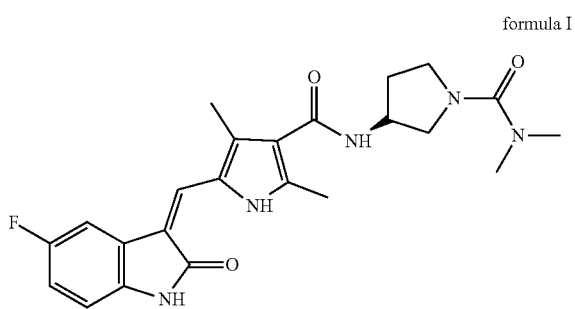

formula I wherein the composition has an X-ray powder diffraction pattern comprising peaks at diffraction angle 2θ of 3.9±0.2°, 7.8±0.2, 9.5±0.2°, 10.6±0.2°, and 16.0±0.2°.

38. A pharmaceutical composition, comprising a therapeutically effective amount of the composition according to claim 37, and at least one pharmaceutically acceptable adjuvant.

39. A composition comprising a mixture of crystalline form 5 and at least one other crystalline form of the compound of formula I selected from crystalline form 1, crystalline form 2, crystalline form 3, crystalline form 6, and crystalline form 7,

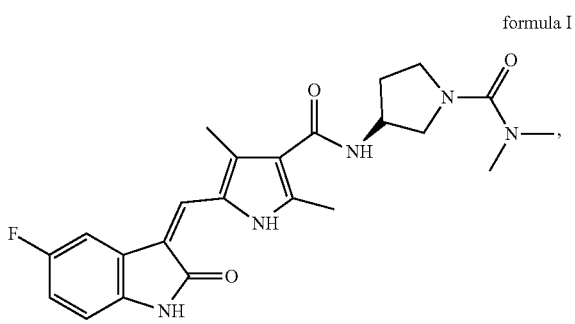

formula I wherein,
the crystalline form 5 has an X-ray powder diffraction pattern comprising peaks at diffraction angle 2θ of 8.7±0.2°, 9.4±0.2°, and 18.1±0.2°,
the crystalline form 1 has an X-ray powder diffraction pattern comprising peaks at diffraction angle 2θ of 4.3±0.2°, 8.6±0.2°, and 12.9±0.2°,
the crystalline form 2 has an X-ray powder diffraction pattern comprising peaks at diffraction angle 2θ of 8.8±0.2°, 10.1±0.2°, 23.8±0.2°, and 26.7±0.2°,
the crystalline form 3 has an X-ray powder diffraction pattern comprising a peak at diffraction angle 2θ of 3.9±0.2° and 7.8±0.2°,
the crystalline form 6 has an X-ray powder diffraction pattern comprising peaks at diffraction angle 2θ of 7.9±0.2°, 9.1±0.2°, and 17.7±0.2°, and
the crystalline form 7 has an X-ray powder diffraction pattern comprising peaks at diffraction angle 2θ of 9.5±0.2°, 10.6±0.2°, and 16.0±0.2°.

40. The composition of claim 39, wherein the composition has an X-ray powder diffraction pattern comprising peaks at diffraction angle 2θ of 9.4±0.2°, 10.5±0.2°, and 18.1±0.2°, and further comprises at least one additional peak at diffraction angle 2θ selected from 4.3±0.2°, 7.8±0.2°, 7.9±0.2°, 8.6±0.2°, 8.8±0.2°, 9.1±0.2°, 9.5±0.2°, 10.1±0.2°, 10.6±0.2°, 12.9±0.2°, 16.0±0.2°, 17.7±0.2°, 23.8±0.2°, and 26.7±0.2°.

41. A pharmaceutical composition, comprising a therapeutically effective amount of the composition according to claim 40, and at least one pharmaceutically acceptable adjuvant.

42. A pharmaceutical composition, comprising a therapeutically effective amount of the composition according to claim 39, and at least one pharmaceutically acceptable adjuvant.

43. A composition of the compound of formula I:

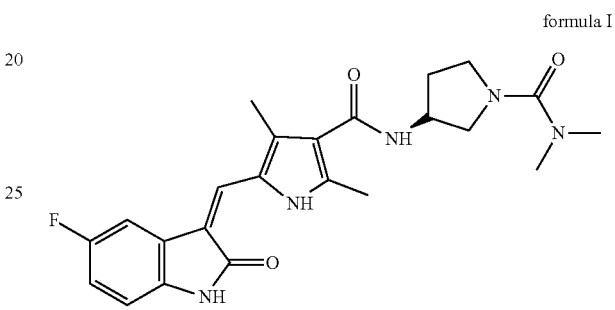

formula I comprising the crystalline form 7 according to claim 24 and at least one crystalline form of compound of formula I selected from crystalline form 1, crystalline form 2, crystalline form 3, crystalline form 5, and crystalline form 6,
wherein,
the crystalline form 1 has an X-ray powder diffraction pattern comprising peaks at diffraction angle 2θ of 4.3±0.2°, 8.6±0.2°, and 12.9±0.2°,
the crystalline form 2 has an X-ray powder diffraction pattern comprising peaks at diffraction angle 2θ of 8.8±0.2°, 10.1±0.2°, 23.8±0.2°, and 26.7±0.2°,
the crystalline form 3 has an X-ray powder diffraction pattern comprising a peak at diffraction angle 2θ of 3.92±0.2° and 7.8±0.2°,
the crystalline form 5 has an X-ray powder diffraction pattern comprising peaks at diffraction angle 2θ of 8.7±0.2°, 17.0±0.2°, and 17.4±0.2°, and
the crystalline form 6 has an X-ray powder diffraction pattern comprising peaks at diffraction angle 2θ of 7.9±0.2°, 9.1±0.2°, and 17.7±0.2°.

44. The composition of claim 43, wherein the X-ray power diffraction pattern of the crystalline form 7 further comprises peaks at diffraction angle 2θ of 4.8±0.2° and 25.1±0.2.

45. A pharmaceutical composition, comprising a therapeutically effective amount of the crystalline form 7 according to claim 43, and at least one pharmaceutically acceptable adjuvant.

* * * * *